US012735459B2

(12) United States Patent
Frederick et al.

(10) Patent No.: US 12,735,459 B2
(45) Date of Patent: Sep. 15, 2026

(54) MODIFIED ADENO-ASSOCIATED VIRAL CAPSID PROTEINS FOR OCULAR GENE THERAPY AND METHODS OF USE THEREOF

(71) Applicant: GENZYME CORPORATION, Cambridge, MA (US)

(72) Inventors: Amy Frederick, Cambridge, MA (US); Xiaoying Jin, Cambridge, MA (US); Lin Liu, Cambridge, MA (US); Catherine O'Riordan, Cambridge, MA (US); Jennifer Sullivan, Cambridge, MA (US)

(73) Assignee: GENZYME CORPORATION, Cambridge, MA (US)

( * ) Notice: Subject to any disclaimer, the term of this patent is extended or adjusted under 35 U.S.C. 154(b) by 1169 days.

(21) Appl. No.: 17/162,356

(22) Filed: Jan. 29, 2021

(65) Prior Publication Data

US 2021/0261625 A1 Aug. 26, 2021

Related U.S. Application Data

(60) Provisional application No. 62/967,416, filed on Jan. 29, 2020.

(51) Int. Cl.

| | |
|---|---|
| ***C07K 14/015*** | (2006.01) |
| ***A61K 48/00*** | (2006.01) |
| ***A61P 27/02*** | (2006.01) |
| ***C07K 14/005*** | (2006.01) |
| ***C12N 15/86*** | (2006.01) |

(52) U.S. Cl.

CPC ........ *C07K 14/015* (2013.01); *A61K 48/0025* (2013.01); *A61K 48/0041* (2013.01); *A61K 48/0075* (2013.01); *A61P 27/02* (2018.01); *C07K 14/005* (2013.01); *C12N 15/86* (2013.01); *A61K 48/00* (2013.01); *C12N 2750/14121* (2013.01); *C12N 2750/14122* (2013.01); *C12N 2750/14143* (2013.01); *C12N 2750/14145* (2013.01)

(58) Field of Classification Search

CPC .................. C07K 14/005; C12N 15/86; C12N 2750/14122; C12N 2750/14123; C12N 2750/14143; A61K 48/00; A61K 48/0025; A61K 48/0041; A61K 48/0075; A61P 27/02

USPC ...... 424/93.2, 233.1, 199.1; 435/456, 320.1; 536/23.72; 530/826

See application file for complete search history.

(56) References Cited

U.S. PATENT DOCUMENTS

| | | | | |
|---|---|---|---|---|
| 6,225,291 | B1 | 5/2001 | Lewin et al. | |
| 6,566,118 | B1 | 5/2003 | Atkinson et al. | |
| 6,723,551 | B2 | 4/2004 | Kotin et al. | |
| 6,989,264 | B2 | 1/2006 | Atkinson et al. | |
| 6,995,006 | B2 | 2/2006 | Atkinson et al. | |
| 8,137,948 | B2 | 3/2012 | Qu et al. | |
| 8,445,267 | B2 | 5/2013 | Zhong et al. | |
| 2014/0335054 | A1 | 11/2014 | Gao et al. | |
| 2018/0023094 | A1* | 1/2018 | Gao ......................... | C12N 7/00 800/13 |
| 2021/0230229 | A1* | 7/2021 | Church ................ | C07K 14/005 |

FOREIGN PATENT DOCUMENTS

| | | | | |
|---|---|---|---|---|
| JP | 2017-509632 | A | 4/2017 | |
| JP | 2017-518271 | A | 7/2017 | |
| JP | 2017-532966 | A | 11/2017 | |
| WO | WO 1998/010088 | A1 | 3/1998 | |
| WO | WO 2009/105690 | A2 | 8/2009 | |
| WO | WO 2010/148143 | A1 | 12/2010 | |
| WO | WO-2012109570 | A1 * | 8/2012 | .............. A61P 21/00 |
| WO | WO 2015/121501 | A1 | 8/2015 | |
| WO | WO 2015/143418 | A2 | 9/2015 | |
| WO | WO 2015/168666 | A2 | 11/2015 | |
| WO | WO 2016/065001 | A1 | 4/2016 | |
| WO | WO 2018/035059 | A1 | 2/2018 | |
| WO | WO-2018035213 | A1 * | 2/2018 | ......... A61K 31/7088 |
| WO | WO 2019/221992 | A1 | 11/2019 | |

OTHER PUBLICATIONS

Stagg SM, Yoshioka C, Davulcu O, Chapman MS. Cryo-electron Microscopy of Adeno-associated Virus. Chem Rev. Sep. 14, 2022;122(17):14018-14054. Epub May 16, 2022. (Year: 2022).*

Tseng YS, Gurda BL, Chipman P, McKenna R, Afione S, Chiorini JA, Muzyczka N, Olson NH, Baker TS, Kleinschmidt J, Agbandje-McKenna M. J Virol. Feb. 2015;89(3):1794-808. (Year: 2015).*

Alberts B, Johnson A, Lewis J, et al. Molecular Biology of the Cell. 4th edition. New York: Garland Science; 2002. The Shape and Structure of Proteins. Available from: https://www.ncbi.nlm.nih.gov/books/NBK26830/ (Year: 2002).*

Jin X, Liu L, Nass S, O'Riordan C, Pastor E, Zhang XK. Direct Liquid Chromatography/Mass Spectrometry Analysis for Complete Characterization of Recombinant Adeno-Associated Virus Capsid Proteins. Hum Gene Ther Methods. Oct. 2017;28(5):255-267. Epub Jun. 16, 2017. (Year: 2017).*

Srivastava 2016, Current Opinion in Virology, 21, 75-80. (Year: 2016).*

(Continued)

*Primary Examiner* — Anne Marie S Wehbe
*Assistant Examiner* — Katie L Pennington
(74) *Attorney, Agent, or Firm* — LATHROP GPM LLP; James H. Velema, Esq.

(57) ABSTRACT

Provided herein are modified adeno-associated viral (AAV) capsid proteins, compositions (e.g., rAAV) comprising the capsid proteins, and nucleic acids encoding the capsid proteins. The AAV capsids provided herein confer retinal cell tropism and/or corneal cell tropism, and mediate improved transduction efficiency in clinically relevant ocular cell types such as photoreceptors and/or corneal endothelial cells. Also provided are nucleic acids encoding the capsid proteins, and AAV particles comprising the capsid proteins.

28 Claims, 15 Drawing Sheets

Specification includes a Sequence Listing.

(56) References Cited

OTHER PUBLICATIONS

Frederick et al., "Engineered Capsids for Efficient Gene Delivery to the Retina and Cornea", Human Gene Therapy, Jul. 1, 2020, 31(13-14): 756-774.
International Search Report and Written Opinion for PCT International Application No. PCT/US2021/015695, mailed Jun. 4, 2021.
Kay et al., Targeting Photoreceptors via Intravitreal Delivery Using Novel, Capsid-Mutated AAV Vectors, PLOS One, Feb. 16, 2013, 8(4): e6207.
Bogner, et al., "Capsid Mutated Adeno-Associated Virus Delivered to the Anterior Chamber Results in Efficient Transduction of Trabecular Meshwork in Mouse and Rat", PloS One, vol. 10, No. 6, e0128759, pp. 1-16, Jun. 8, 2015.
Boshart, et al., "A Very Strong Enhancer Is Located Upstream of an Immediate Early Gene of Human Cytomegalovirus", Cell, vol. 41, No. 2, pp. 521-530, Jun. 1, 1985.
Carvalho, et al., "Synthetic Adeno-Associated Viral Vector Efficiently Targets Mouse and Nonhuman Primate Retina In Vivo", Human Gene Therapy, vol. 29, No. 7, pp. 771-784, Jul. 1, 2018.
Choudhury, et al., "In Vivo Selection Yields Aav-b1 Capsid for Central Nervous System and Muscle Gene Therapy", Molecular Therapy, vol. 24, Issue 7, pp. 1247-1257, Jul. 2016.
Clark, et al., "Highly Purified Recombinant Adeno-associated Virus Vectors Are Biologically Active and Free of Detectable Helper and Wild-type Viruse", Human Gene Therapy, vol. 10, No. 6, pp. 1031-1039, 1999.
Conway, et al., "Recombinant Adeno-associated Virus Type 2 Replication and Packaging Is Entirely Supported by a Herpes Simplex Virus Type 1 Amplicon Expressing Rep and Cap", Journal of Virology, vol. 71, No. 11, pp. 8780-8789, 1997.
Dalkara, et al., "In Vivo-Directed Evolution of a New Adeno-associated Virus for Therapeutic Outer Retinal Gene Delivery From the Vitreous", Science Translational Medicine, vol. 5, Issue 189, pp. 1-12, Jun. 12, 2013.
Fagan, et al., "Intravitreal Injections: a Review of the Evidence for Best Practice", Clinical & Experimental Ophthalmology, vol. 41, pp. 500-507, 2013.
Fisher, et al., "Transduction With Recombinant Adeno-Associated Virus for Gene Therapy Is Limited by Leading-Strand Synthesis", Journal of virology, vol. 70, No. 1, pp. 520-532, 1996.
Gao, et al., "Novel Adeno-associated Viruses From Rhesus Monkeys as Vectors for Human Gene Therapy", Proceedings of the National Academy of Sciences, vol. 99, No. 18, pp. 11854-11859, Sep. 3, 2002.
Girod, et al., "The VP1 Capsid Protein of Adeno-associated Virus Type 2 Is Carrying a Phospholipase A2 Domain Required for Virus Infectivity", Journal of General Virology, vol. 83, No. 5, pp. 973-978, 2002.
Gossen, et al., "Tight Control of Gene Expression in Mammalian Cells by Tetracycline-responsive Promoters", Proceedings of the National Academy of Sciences, vol. 89, No. 12, pp. 5547-5551, Jun. 1992.
Gossen, et al., "Transcriptional Activation by Tetracyclines in Mammalian Cells", Science, vol. 268, No. 5218, pp. 1766-1769, 1995.
Guo, et al., "Evaluation of Promoter Strength for Hepatic Gene Expression in Vivo Following Adenovirus-mediated Gene", Gene Therapy, vol. 3, pp. 802-810, 1996.
Harvey, et al., "Inducible Control of Gene Expression: Prospects for Gene Therapy", Current Opinion in Chemical Biology, vol. 2, Issue 4, pp. 512-518, 1998.
Jin, et al., "Direct Liquid Chromatography/mass Spectrometry Analysis for Complete Characterization of Recombinant Adeno-associated Virus Capsid Proteins", Human Gene Therapy Methods, vol. 28, No. 5, pp. 255-267, 2017.
Kim, et al., "Use of the Human Elongation Factor 1α Promoter as a Versatile and Efficient Expression System", Gene, vol. 91, No. 2, pp. 217-223, 1990.
Magari, et al., "Pharmacologic Control of a Humanized Gene Therapy System Implanted Into Nude Mice", The Journal of Clinical Investigation, vol. 100, No. 11, pp. 2865-2872, 1997.
Martin, et al., "Generation and Characterization of Adeno-associated Virus Producer Cell Lines for Research and Preclinical Vector Production", Human Gene Therapy Methods, vol. 24, No. 4, pp. 253-269, 2013.
Mclaughlin, et al., "Adeno-associated virus general transduction vectors: analysis of proviral structures", Journal of Virology, vol. 62, pp. 1963-1973, 1989.
Mcpherson, et al., "Structural Proteins of Adenovirus-associated Virus: Subspecies and Their Relatedness", Journal of Virology, vol. 46, No. 2, pp. 523-529, 1983.
Miyazaki, et al., "Expression Vector System Based on the Chicken β-Actin Promoter Directs Efficient Production of Interleukin-5", Gene, vol. 79, Issue 2, pp. 269-277, Jul. 15, 1989.
Nass, et al., "Universal Method for the Purification of Recombinant AAV Vectors of Differing Serotypes", Molecular Therapy—Methods & Clinical Development, vol. 9, pp. 33-46, 2017.
Niwa, et al., "Efficient Selection for High-Expression Transfectants with a Novel Eukaryotic Vector", Gene, vol. 108, No. 2, pp. 193-199, Dec. 15, 1991.
No, et al., "Ecdysone-inducible Gene Expression in Mammalian Cells and Transgenic Mice", Proceedings of the National Academy of Sciences, vol. 93, No. 8, pp. 3346-3351, Apr. 1996.
Peyman, et al., "Intravitreal Injection of Therapeutic Agents", Retina, vol. 29, No. 7, pp. 875-912, 2009.
Remington, et al., Remington's Pharmaceutical Sciences, 15th Edition, pp. 1035-1038.
Remington, et al., Remington's Pharmaceutical Sciences, 15th Edition, pp. 1570-1580.
Sullivan, et al., "Rationally Designed AAV2 and AAVrh8R Capsids Provide Improved Transduction in the Retina and Brain", Gene Therapy, vol. 25, No. 3, pp. 205-219, May 22, 2018.
Veldwijk, et al., "Development and Optimization of a Real-time Quantitative PCR-based Method for the Titration of AAV-2 Vector Stocks", Molecular Therapy, vol. 6, No. 2, pp. 272-278, 2002.
Wang, et al., "Ligand-inducible and Liver-specific Target Gene Expression in Transgenic Mice", Nature Biotechnology, vol. 15, pp. 239-243, 1997.
Wang, et al., "Positive and Negative Regulation of Gene Expression in Eukaryotic Cells With an Inducible Transcriptional Regulator", Gene Therapy, vol. 4, No. 5, pp. 432-441, 1997.
Xiao, et al., "Gene Transfer by Adeno-associated Virus Vectors Into the Central Nervous System", Experimental Neurology, vol. 144, Issue 1, pp. 113-124, Mar. 1997.
Xiao, et al., "Production of High-titer Recombinant Adeno-associated Virus Vectors in the Absence of Helper Adenovirus", Journal of Virology, vol. 72, No. 3, pp. 2224-2232, 1998.
Feldman et al., "Identification of a Linear Heparin Binding Domain for Human Respiratory Syncytial Virus Attachment Glycoprotein G", Journal of Virology, Aug. 1, 1999, 73(8): 6610-6617.
Kay et al., "Targeting Photoreceptors via Intravitreal Delivery Using Novel, Capsid-Mutated AAV Vectors", PLOS ONE, Apr. 26, 2013, 8(4): e62097.
NIH—National Library of Medicine, "capsid protein [adeno-associated virus 5]", NCBI Reference Sequence: YP_068409.1, dated Aug. 13, 2018.
Opie et al., "Identification of Amino Acid Residues in the Capsid Proteins of Adeno-Associated Virus Type 2 That Contribute to Heparan Sulfate Proteoglycan Binding", Journal of Virology, Jun. 15, 2003, 77(12): 6995-7006.
Ree et al., "Spotlight on protein N-terminal acetylation", Exp Mol Med, Jul. 27, 2018, 50(7): 1-13.
Shi et al., "Insertional mutagenesis at positions 520 and 584 of adeno-associated virus type 2 (AAV2) capsid gene and generation of AAV2 vectors with eliminated heparin-binding ability and introduced novel tropism", Human Gene Therapy, Mar. 2006, 17(3): 353-361.

* cited by examiner

Fig. 2B

AAV2 HBKO

Two weeks

Four weeks

AAV5
ONL
INL
RGL
GFP/Rhodopsin

AAV2 HBKO
ONL
INL
RGL
GFP/Rhodopsin

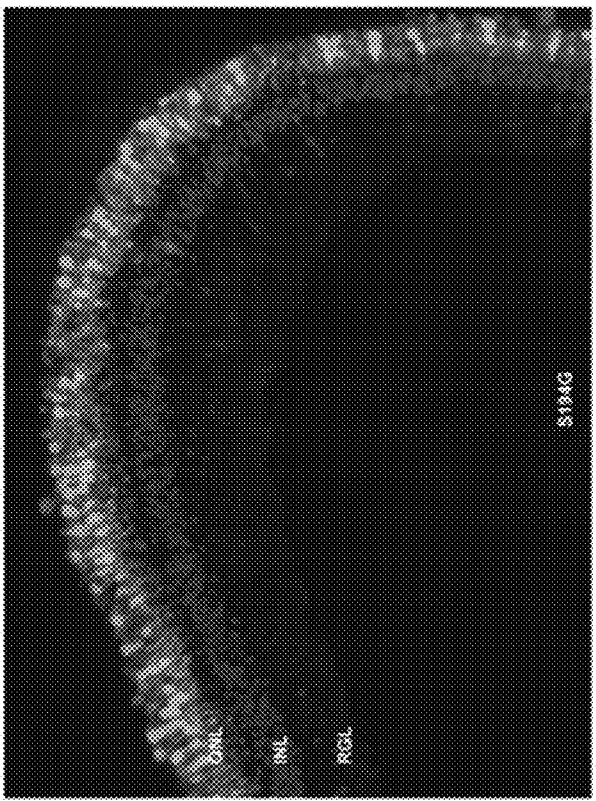
Fig. 10A
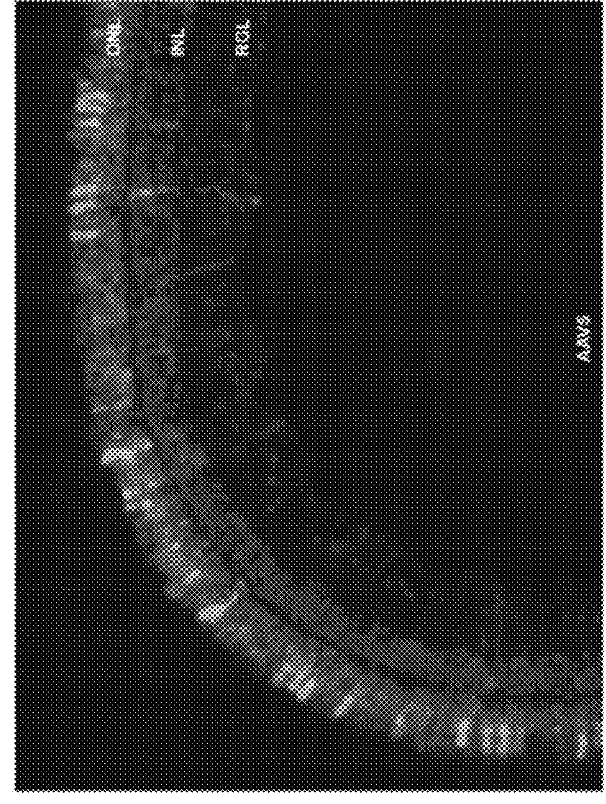

MODIFIED ADENO-ASSOCIATED VIRAL CAPSID PROTEINS FOR OCULAR GENE THERAPY AND METHODS OF USE THEREOF

CROSS-REFERENCE TO RELATED APPLICATIONS

This application claims the benefit of U.S. Provisional Application No. 62/967,416, filed Jan. 29, 2020, the disclosure of which is hereby incorporated by reference in its entirety.

SEQUENCE LISTING

This application contains a sequence listing which has been submitted electronically in ASCII format and is hereby incorporated by reference in its entirety (said ASCII copy, created on Jan. 29, 2021, is named "714497_SA9-285_ST25.txt" and is 47,504 bytes in size).

BACKGROUND

Gene therapy provides the promise of curative treatment of human diseases using genetic methods, which can include either introducing a healthy copy of a gene (e.g., a mutated gene), or correcting a gene to restore its biological function. Adeno-associated viral (AAV) vectors derived from non-pathogenic and non-enveloped replication-defective parvovirus represent an ideal vehicle for human gene delivery. One advantage to the AAV vector system is the availability of multiple naturally occurring serotypes that provide selective tropisms for various target cells.

While gene therapy is being pursued as a strategy for treating a range of genetic diseases, ocular disorders are particularly attractive indications for gene therapy. The genetic nature and mechanisms responsible for various ocular diseases have been identified. Post-mitotic cells of the eye, for example, retinal cells and corneal endothelial cells, allow for sustained gene expression without the need for transgenic integration. Coupled with well-defined anatomical features, the eye provides a directly visible and accessible tissue that provides advantages for local delivery. Further, the blood-ocular barrier gives rise to immune privilege and limits immune responses against gene therapy products delivered into the eye. Numerous on-going clinical and preclinical studies of ocular gene therapy underscore the utility of AAV vectors as an effective tool to correct various ocular conditions.

One disadvantage to the use of naturally occurring AAV serotypes, in the context of posterior retinal gene therapy, is that their delivery requires an invasive sub retinal surgery. Thus, to address the need for a less invasive delivery route, there is a need in the art to develop AAV vectors that can transduce outer retina (i.e., photoreceptors/Retinal Pigment Epithelium (RPE)) following intravitreal injection. Moreover, there is a need in the art to develop a less invasive surgical procedure than intracameral delivery or corneal puncture for the delivery of genes to the anterior chamber of the eye, specifically corneal endothelial cells.

SUMMARY

Provided herein are modified adeno-associated viral (AAV) capsid proteins, compositions (e.g., rAAV) comprising the capsid proteins, and nucleic acids encoding the capsid proteins. The AAV capsids provided herein confer retinal cell tropism and/or corneal cell tropism, and mediate improved transduction efficiency in clinically relevant ocular cell types such as photoreceptors and/or corneal endothelial cells. rAAV comprising the AAV capsid proteins provided herein are useful for non-invasive ocular delivery routes, such as intravitreal administration, and it is believed that they will be well tolerated when administered to human subjects. As such, the provided compositions are particularly useful for gene therapy applications (e.g., ocular gene therapy).

Accordingly, in certain aspects, a modified adeno-associated virus (AAV) capsid protein comprising an amino acid substitution at one or more positions corresponding to amino acids S194, G474, N564, and/or N573, wherein numbering of the positions is based on VP1 numbering of AAV5, is provided.

In certain exemplary embodiments, numbering of the positions is based on the amino acid sequence of the wild-type AAV5 VP1 as set forth in SEQ ID NO:1.

In certain exemplary embodiments, the modified capsid protein is a modified capsid protein of an AAV serotype selected from the group consisting of AAV1, AAV2, AAV4, AAV5, AAV6, AAV7, AAV8, AAV9, AAVB1, AAVAnc80, AAV7m8, AAVrh10, AAV2 (Y444F), AAV2 (Y444+500+730), AAV2 (Y252+272+444+500+700+704+730F), AAV8 (Y733F), and any variant thereof. In certain exemplary embodiments, the modified capsid protein is a modified capsid protein of AAV5.

In certain exemplary embodiments, the modified capsid protein comprises an amino acid sequence having at least 80%, at least 85%, at least 90%, at least 91%, at least 92%, at least 93%, at least 94%, at least 95%, at least 96%, at least 97%, at least 98%, at least 99% sequence identity with the amino acid sequence set forth in SEQ ID NO:1. In certain exemplary embodiments, the modified capsid protein comprises an amino acid sequence having at least 95% sequence identity with the amino acid sequence set forth in SEQ ID NO:1. In certain exemplary embodiments, the modified capsid protein comprises an amino acid sequence having at least 99% sequence identity with the amino acid sequence set forth in SEQ ID NO:1.

In certain exemplary embodiments, the amino acid in the capsid protein corresponding to amino acid 194 is G. In certain exemplary embodiments, the modified capsid protein comprises an amino acid sequence having at least 80%, at least 85%, at least 90%, at least 91%, at least 92%, at least 93%, at least 94%, at least 95%, at least 96%, at least 97%, at least 98%, at least 99% sequence identity with the amino acid sequence set forth in SEQ ID NO:3, wherein the amino acid in the capsid protein corresponding to amino acid 194 of SEQ ID NO:3 is G.

In certain exemplary embodiments, the amino acid in the capsid protein corresponding to amino acid 474 is R. In certain exemplary embodiments, the modified capsid protein comprises an amino acid sequence having at least 80%, at least 85%, at least 90%, at least 91%, at least 92%, at least 93%, at least 94%, at least 95%, at least 96%, at least 97%, at least 98%, at least 99% sequence identity with the amino acid sequence set forth in SEQ ID NO:5, wherein the amino acid in the capsid protein corresponding to amino acid 474 of SEQ ID NO:5 is R.

In certain exemplary embodiments, the amino acid in the capsid protein corresponding to amino acid 564 is R. In certain exemplary embodiments, the modified capsid protein comprises an amino acid sequence having at least 80%, at least 85%, at least 90%, at least 91%, at least 92%, at least 93%, at least 94%, at least 95%, at least 96%, at least 97%, at least 98%, at least 99% sequence identity with the amino acid sequence set forth in SEQ ID NO:7, wherein the amino acid in the capsid protein corresponding to amino acid 564 of SEQ ID NO:7 is R.

In certain exemplary embodiments, the amino acid in the capsid protein corresponding to amino acid 573 is R. In certain exemplary embodiments, the modified capsid protein comprises an amino acid sequence having at least 80%, at least 85%, at least 90%, at least 91%, at least 92%, at least 93%, at least 94%, at least 95%, at least 96%, at least 97%, at least 98%, at least 99% sequence identity with the amino acid sequence set forth in SEQ ID NO:9, wherein the amino acid in the capsid protein corresponding to amino acid 573 of SEQ ID NO:9 is R.

In certain aspects, a modified adeno-associated virus (AAV) capsid protein comprising: a G at the position corresponding to amino acid 194; an R at the position corresponding to amino acid 474; an R at the position corresponding to amino acid 564; and/or an R at the position corresponding to amino acid 573, wherein numbering of the position is based on VP1 numbering of AAV5, is provided.

In certain aspects, a modified adeno-associated virus (AAV) capsid protein comprising a G at the position corresponding to amino acid 194, wherein numbering of the position is based on VP1 numbering of AAV5, is provided.

In certain aspects, a modified adeno-associated virus (AAV) capsid protein comprising an R at the position corresponding to amino acid 474, wherein numbering of the position is based on VP1 numbering of AAV5, is provided.

In certain aspects, a modified adeno-associated virus (AAV) capsid protein comprising an R at the position corresponding to amino acid 564, wherein numbering of the position is based on VP1 numbering of AAV5, is provided.

In certain aspects, a modified adeno-associated virus (AAV) capsid protein comprising an R at the position corresponding to amino acid 573, wherein numbering of the position is based on VP1 numbering of AAV5, is provided.

In certain aspects, a modified adeno-associated virus (AAV) capsid protein comprising the amino acid sequence set forth in SEQ ID NOs: 3, 5, 7, or 9, is provided.

In certain aspects, an isolated nucleic acid encoding the capsid protein described herein, is provided.

In certain aspects, an isolated nucleic acid comprising the nucleotide sequence set forth in SEQ ID NOs: 4, 6, 8, or 10, is provided.

In certain aspects, a vector comprising the nucleic acid described herein, is provided.

In certain exemplary embodiments, the vector is a plasmid or a helper viral vector. In certain exemplary embodiments, the helper viral vector is a retrovirus vector, a herpes virus vector, a baculovirus vector, or an adenovirus vector. In certain exemplary embodiments, the vector is an expression vector.

In certain aspects, a recombinant cell comprising the nucleic acid described herein, or the vector described herein, is provided.

In certain aspects, a method of producing an AAV capsid protein, the method comprising culturing the recombinant cell described herein under conditions whereby the nucleic acid is expressed and the capsid protein is produced, is provided.

In certain aspects, a recombinant adeno-associated viral (rAAV) particle comprising: (a) an rAAV capsid comprising a modified capsid protein, wherein the modified capsid protein comprises an amino acid substitution at one or more positions corresponding to amino acids 194, 474, 564, and/or 573, wherein numbering of the positions is based on VP1 numbering of AAV5; and (b) an rAAV vector comprising a heterologous nucleic acid, is provided.

In certain exemplary embodiments, numbering of the positions is based on the amino acid sequence of the wild-type AAV5 VP1 as set forth in SEQ ID NO:1.

In certain exemplary embodiments, the modified capsid protein is a modified capsid protein of an AAV serotype selected from the group consisting of AAV1, AAV2, AAV4, AAV5, AAV6, AAV7, AAV8, AAV9, AAVB1, AAVAnc80, AAV7m8, AAVrh10, AAV2 (Y444F), AAV2 (Y444+500+730), AAV2 (Y252+272+444+500+700+704+730F), AAV8 (Y733F), and any variant thereof. In certain exemplary embodiments, the modified capsid protein is a modified capsid protein of AAV5.

In certain exemplary embodiments, the modified capsid protein comprises an amino acid sequence having at least 80%, at least 85%, at least 90%, at least 91%, at least 92%, at least 93%, at least 94%, at least 95%, at least 96%, at least 97%, at least 98%, at least 99% sequence identity with the amino acid sequence set forth in SEQ ID NO:1. In certain exemplary embodiments, the modified capsid protein comprises an amino acid sequence having at least 95% sequence identity with the amino acid sequence set forth in SEQ ID NO:1. In certain exemplary embodiments, the modified capsid protein comprises an amino acid sequence having at least 99% sequence identity with the amino acid sequence set forth in SEQ ID NO:1.

In certain exemplary embodiments, the amino acid in the capsid protein corresponding to amino acid 194 is G. In certain exemplary embodiments, the modified capsid protein comprises an amino acid sequence having at least 80%, at least 85%, at least 90%, at least 91%, at least 92%, at least 93%, at least 94%, at least 95%, at least 96%, at least 97%, at least 98%, at least 99% sequence identity with the amino acid sequence set forth in SEQ ID NO:3, wherein the amino acid in the capsid protein corresponding to amino acid 194 of SEQ ID NO:3 is G.

In certain exemplary embodiments, the amino acid in the capsid protein corresponding to amino acid 474 is R. In certain exemplary embodiments, the modified capsid protein comprises an amino acid sequence having at least 80%, at least 85%, at least 90%, at least 91%, at least 92%, at least 93%, at least 94%, at least 95%, at least 96%, at least 97%, at least 98%, at least 99% sequence identity with the amino acid sequence set forth in SEQ ID NO:5, wherein the amino acid in the capsid protein corresponding to amino acid 474 of SEQ ID NO:5 is R.

In certain exemplary embodiments, the amino acid in the capsid protein corresponding to amino acid 564 is R. In certain exemplary embodiments, the modified capsid protein comprises an amino acid sequence having at least 80%, at least 85%, at least 90%, at least 91%, at least 92%, at least 93%, at least 94%, at least 95%, at least 96%, at least 97%, at least 98%, at least 99% sequence identity with the amino acid sequence set forth in SEQ ID NO:7, wherein the amino acid in the capsid protein corresponding to amino acid 564 of SEQ ID NO:7 is R.

In certain exemplary embodiments, the amino acid in the capsid protein corresponding to amino acid 573 is R. In certain exemplary embodiments, the modified capsid protein comprises an amino acid sequence having at least 80%, at least 85%, at least 90%, at least 91%, at least 92%, at least 93%, at least 94%, at least 95%, at least 96%, at least 97%, at least 98%, at least 99% sequence identity with the amino acid sequence set forth in SEQ ID NO:9, wherein the amino acid in the capsid protein corresponding to amino acid 573 of SEQ ID NO:9 is R.

In certain aspects, a recombinant adeno-associated viral (rAAV) particle comprising: (a) an rAAV capsid comprising a modified capsid protein, wherein the modified capsid protein comprises: a G at the position corresponding to amino acid 194, an R at the position corresponding to amino acid 474, an R at the position corresponding to amino acid 564, and/or an R at the position corresponding to amino acid 573, wherein numbering of the position is based on VP1 numbering of AAV5; and (b) an rAAV vector comprising a heterologous nucleic acid, is provided.

In certain aspects, a recombinant adeno-associated viral (rAAV) particle comprising: (a) an rAAV capsid comprising a G at the position corresponding to amino acid 194, wherein numbering of the position is based on VP1 numbering of AAV5; and (b) an rAAV vector comprising a heterologous nucleic acid, is provided.

In certain aspects, a recombinant adeno-associated viral (rAAV) particle comprising: (a) an rAAV capsid comprising an R at the position corresponding to amino acid 474, wherein numbering of the position is based on VP1 numbering of AAV5; and (b) an rAAV vector comprising a heterologous nucleic acid, is provided.

In certain aspects, a recombinant adeno-associated viral (rAAV) particle comprising: (a) an rAAV capsid comprising an R at the position corresponding to amino acid 564, wherein numbering of the position is based on VP1 numbering of AAV5; and (b) an rAAV vector comprising a heterologous nucleic acid, is provided.

In certain aspects, a recombinant adeno-associated viral (rAAV) particle comprising: (a) an rAAV capsid comprising an R at the position corresponding to amino acid 573, wherein numbering of the position is based on VP1 numbering of AAV5; and (b) an rAAV vector comprising a heterologous nucleic acid, is provided.

In certain exemplary embodiments, the heterologous nucleic acid encodes a therapeutic polypeptide or therapeutic nucleic acid. In certain exemplary embodiments, the heterologous nucleic acid encodes a polypeptide selected from the group consisting of an antioxidant, an enzyme, a neurotrophic factor, an anti-apoptotic factor, an anti-angiogenic factor, and an anti-inflammatory factor. In certain exemplary embodiments, the heterologous nucleic acid encodes a therapeutic nucleic acid. In certain exemplary embodiments, the therapeutic nucleic acid is an siRNA, an shRNA, an RNAi, an miRNA, an antisense RNA, a ribozyme or a DNAzyme.

In certain exemplary embodiments, the heterologous nucleic acid is operably linked to a constitutive promoter. In certain exemplary embodiments, the heterologous nucleic acid is operably linked to a promoter suitable for expression of the therapeutic polypeptide or therapeutic nucleic acid in an ocular tissue. In certain exemplary embodiments, the ocular tissue is a retina, and the promoter is suitable for expression of the therapeutic polypeptide or therapeutic nucleic acid in a retinal cell selected from the group consisting of a photoreceptor cell, a retinal pigmented epithelial cell, a bipolar cell, a horizontal cell, an amacrine cell, a muller cell, a ganglion cell, and any combination thereof. In certain exemplary embodiments, the ocular tissue is a cornea, and the promoter is suitable for expression of the therapeutic polypeptide or therapeutic nucleic acid in a corneal cell selected from the group consisting of an epithelial cell, a keratocyte, an endothelial cell, and any combination thereof.

In certain exemplary embodiments, the AAV vector further comprises inverted terminal repeats (ITRs).

In certain exemplary embodiments, the rAAV vector is a self-complementary rAAV vector (scAAV). In certain exemplary embodiments, the scAAV comprises a first nucleic acid encoding the heterologous nucleic acid, and a second nucleic acid encoding a complement of the first nucleic acid, wherein the first nucleic acid can form intrastrand base pairs with the second nucleic acid along most or all of its length. In certain exemplary embodiments, the first nucleic acid and the second nucleic acid are linked by a mutated AAV ITR, wherein the mutated AAV ITR comprises a deletion of the D region and comprises a mutation of the terminal resolution sequence.

In certain aspects, a pharmaceutical composition comprising a rAAV particle described herein, is provided.

In certain aspects, a method for delivering a heterologous nucleic acid to an ocular tissue of a subject in need thereof, comprising administering a recombinant adeno-associated virus (rAAV) particle to the subject, wherein the rAAV particle comprises: (a) an rAAV capsid comprising a modified capsid protein, wherein the modified capsid protein comprises an amino acid substitution at one or more positions corresponding to amino acids 194, 474, 564, and/or 573, wherein numbering of the positions is based on VP1 numbering of AAV5; and (b) an rAAV vector comprising a heterologous nucleic acid, is provided.

In certain aspects, a method for delivering a heterologous nucleic acid to the retina of a subject in need thereof, comprising administering a recombinant adeno-associated virus (rAAV) particle to the subject, wherein the rAAV particle comprises: (a) an rAAV capsid comprising a modified capsid protein, wherein the modified capsid protein comprises an amino acid substitution at a position corresponding to amino acid 194, wherein numbering of the positions is based on VP1 numbering of AAV5; and (b) an rAAV vector comprising a heterologous nucleic acid, is provided.

In certain aspects, a method for delivering a heterologous nucleic acid to the cornea of a subject in need thereof, comprising administering a recombinant adeno-associated virus (rAAV) particle to the subject, wherein the rAAV particle comprises: (a) an rAAV capsid comprising a modified capsid protein, wherein the modified capsid protein comprises an amino acid substitution at one or more positions corresponding to amino acids 474, 564, and/or 573, wherein numbering of the positions is based on VP1 numbering of AAV5; and (b) an rAAV vector comprising a heterologous nucleic acid, is provided.

In certain aspects, a method for improving rAAV transduction of cells in an ocular tissue of a subject in need thereof, the method comprising administering a recombinant adeno-associated virus (rAAV) particle to the subject, wherein the rAAV particle comprises: (a) an rAAV capsid comprising a modified capsid protein, wherein the modified capsid protein comprises an amino acid substitution at one or more positions corresponding to amino acids 194, 474, 564, and/or 573, wherein numbering of the positions is based on VP1 numbering of AAV5; and (b) an rAAV vector comprising a heterologous nucleic acid, is provided.

In certain aspects, a method for improving rAAV transduction of cells in the retina of a subject in need thereof, the method comprising administering a recombinant adeno-associated virus (rAAV) particle to the subject, wherein the rAAV particle comprises: (a) an rAAV capsid comprising a modified capsid protein, wherein the modified capsid protein comprises an amino acid substitution at a position corresponding to amino acid 194, wherein numbering of the positions is based on VP1 numbering of AAV5; and (b) an rAAV vector comprising a heterologous nucleic acid, is provided.

In certain aspects, a method for improving rAAV transduction of cells in the cornea of a subject in need thereof, the method comprising administering a recombinant adeno-associated virus (rAAV) particle to the subject, wherein the rAAV particle comprises: (a) an rAAV capsid comprising a modified capsid protein, wherein the modified capsid protein comprises an amino acid substitution at one or more positions corresponding to amino acids 474, 564, and/or 573, wherein numbering of the positions is based on VP1 numbering of AAV5; and (b) an rAAV vector comprising a heterologous nucleic acid, is provided.

In certain aspects, a method for improving expression of a heterologous nucleic acid in an ocular tissue of a subject in need thereof, the method comprising administering a recombinant adeno-associated virus (rAAV) particle to the subject, wherein the rAAV particle comprises: (a) an rAAV capsid comprising a modified capsid protein, wherein the modified capsid protein comprises an amino acid substitution at one or more positions corresponding to amino acids 194, 474, 564, and/or 573, wherein numbering of the positions is based on VP1 numbering of AAV5; and (b) an rAAV vector comprising a heterologous nucleic acid, is provided.

In certain aspects, a method for improving expression of a heterologous nucleic acid in the retina of a subject in need thereof, the method comprising administering a recombinant adeno-associated virus (rAAV) particle to the subject, wherein the rAAV particle comprises: (a) an rAAV capsid comprising a modified capsid protein, wherein the modified capsid protein comprises an amino acid substitution at a position corresponding to amino acid 194, wherein numbering of the positions is based on VP1 numbering of AAV5; and (b) an rAAV vector comprising a heterologous nucleic acid, is provided.

In certain aspects, a method for improving expression of a heterologous nucleic acid in the cornea of a subject in need thereof, the method comprising administering a recombinant adeno-associated virus (rAAV) particle to the subject, wherein the rAAV particle comprises: (a) an rAAV capsid comprising a modified capsid protein, wherein the modified capsid protein comprises an amino acid substitution at one or more positions corresponding to amino acids 474, 564, and/or 573, wherein numbering of the positions is based on VP1 numbering of AAV5; and (b) an rAAV vector comprising a heterologous nucleic acid, is provided.

In certain aspects, a method to treat a condition or a disorder of the eye in a subject in need thereof, the method comprising administering an effective amount of a composition comprising an rAAV particle to the subject, wherein the rAAV particle comprises: (a) an rAAV capsid comprising a modified capsid protein, wherein the modified capsid protein comprises an amino acid substitution at one or more positions corresponding to amino acids 194, 474, 564, and/or 573, wherein numbering of the positions is based on VP1 numbering of AAV5; and (b) an rAAV vector comprising a heterologous nucleic acid, is provided.

In certain exemplary embodiments, the composition is formulated for intravitreal administration.

In certain exemplary embodiments, the heterologous nucleic acid is expressed at an increased level of expression, as compared to the level of expression of a heterologous nucleic acid of an rAAV particle comprising a wild-type rAAV capsid.

In certain exemplary embodiments, the administering comprises intravitreal administration.

BRIEF DESCRIPTION OF THE DRAWINGS

The foregoing and other features and advantages of the present invention will be more fully understood from the following detailed description of illustrative embodiments taken in conjunction with the accompanying drawings.

FIG. 1A shows a schematic representation of sections collected for GFP expression. The blue lines represent the areas on the sections that were analyzed for native GFP expression (before, through and after fovea). Only the section that passed through the fovea and the bleb were analyzed. FIG. 1B shows an image of photoreceptor layer at the border of the subretinal bleb transduced with AAV5 hOPS-eGFP. Note the non-transduced cells on the left compared to the transduced cells on the right. ONL: Outer Nuclear Layer, OPL: outer plexiform layer.

FIG. 2A-FIG. 2B depict AAV mediated GFP expression in NHP eyes by fundus auto fluorescence (FAF). FAF showing the GFP fluorescence in the bleb area (circled) treated with AAV5 hOPS-eGFP (FIG. 2A) or AAV2-HBKO-hOPS-eGFP (FIG. 2B). An increase in GFP expression was observed at 4 weeks following AAV treatment (FIG. 2A and FIG. 2B). AAV2-HBKO-eGFP vector spread beyond the margins of the subretinal bleb, whereas the AAV5 vector stayed within the margins of the subretinal bleb (FIG. 2A and FIG. 2B).

FIG. 4A shows that wildtype mice were injected subretinally with similar doses of AAV5, AAV5G474R, AAV5N564R and AAV5N573R. Cryosections were analyzed for AAV mediated native GFP expression under fluorescence microscope. Subretinal injections showed similar transduction efficiency between AAV5 and AAV5 arginine variants. FIG. 4B shows transduction efficiency of AAV5 and AAV5 arginine variants in the mouse cornea. AAVs were delivered by intravitreal injections and analyzed 4 weeks of post transduction. Histological sections showed the intense GFP expression in corneal endothelial cells following transduction of AAV5 arginine variants. Barely detectable GFP was observed from AAV5 transduction. ONL—outer nuclear layer, INL—inner nuclear layer, RGL—retinal ganglion cell layer.

FIG. 5 shows SDS-PAGE gel analysis of $1\times10^{10}$ AAV5 acetylation capsid mutant vector genomes, followed by SYPRO Red staining; lanes 1-6 represent AAV5 S2G, S2P, S194G, S194P, S2G/S194G (co-purified with empty particles), S2P/S194P; VP1, VP2, and VP3 AAV capsid proteins are labeled. Lane 5 shows co-purification of empty AAV particles.

FIG. 6A shows comparison of photoreceptor transduction efficiency between AAV5 and AAV5 acetylation variants (AAV5S2G, AAV5S194G, AAV5S2G/S194G, AAV5S2P, AAV5S194P, and AAV5S2P/S194P). Wild type mice were injected with the same copies of AAV5 and AAV5 acetylation variants and eyes were collected 4 weeks after injection and processed for cryosectioning. Fluorescence microscopy analysis showed strong eGFP expression in the ONL of AAV5S194G injected retinas as compared to its parental AAV5 and other variants. ONL: outer nuclear layer, INL: inner nuclear layer, RGL: retinal ganglion cell layer. FIG. 6B shows quantification of GFP by ELISA of retinas from C57BL/6 mice 4 weeks following subretinal injection of AAV5 and AAV5 acetylation variants vectors encoding for EGFP. FIG. 6C shows qPCR analysis of AAV genome copies in transduced retinas following subretinal injections and expressed as viral genomes/ug protein.

FIG. 7A shows representative fluorescent images of retinal cryosections at 4 weeks of post-injection showing transduction comparison (native GFP expression shown in green) in eyes injected with AAV5, AAV5 S194G, AAV5 S194P at different doses (low $1\times10^8$, medium $5\times10^8$ and high $1\times10^9$). Nuclei were stained with DAPI (blue). ONL: outer nuclear layer, INL: inner nuclear layer, RGL: retinal ganglion cell layer. FIG. 7B shows quantification of GFP by ELISA of retinas from C57BL/6 mice 4 weeks following subretinal injection of AAV5 and AAV5 deacetylation variants vectors encoding for EGFP. FIG. 7C shows qPCR analysis of AAV genome copies in transduced retinas following subretinal injections and expressed as viral genomes/ug protein.

FIG. 8A shows protein sequence motifs located within the VP1 N terminus of AAV2. A35 is the N terminal amino acid for tVP1. $^{57}$NG$^{58}$ is a canonical deamidation motif located within the PLA2 domain. FIG. 8B shows SDS-PAGE analysis of $1\times10^{10}$ AAV2 vector generated by either triple transfection production method (TTx) or producer cell Line production method (PCL). FIG. 8C shows SDS-PAGE gel analysis of $1\times10^{10}$ AAV2 deamidation capsid mutant vector genomes, followed by SYPRO Red staining.

FIG. 9A shows quantification of GFP by ELISA of retinas from wildtype mice 4 weeks following intravitreal injection of AAV2 and AAV2 deamination variants encoding for EGFP. FIG. 9B shows qPCR analysis of AAV genome copies in transduced retinas following intravitreal injections and expressed as viral genomes/ug protein. FIG. 9C shows fluorescence analysis showing native GFP Expression Patterns in wildtype mice after intravitreal injection of AAV2 and AAV2 deamination mutants. ONL: outer nuclear layer, INL: inner nuclear layer, RGL: retinal ganglion cell layer.

FIG. 10A-10B depict comparison of native GFP fluorescence following ex vivo administration of AAV5 and AAV5 acetylation variants in NHP retinal tissue. FIG. 10A shows neural retinal tissue obtained from postmortem NHP eyes. Biopsy punches were made and were cultured on membranes in 6-well plates and transduced with different AAV variants encoding GFP. The tissues were harvested after 6 days of post transduction and fixed and imaged for native GFP expression. The potency of AAV serotypes was compared by analyzing transduction of cell types in each of the ONL, INL, and RGL. FIG. 10B shows that AAV5 variant AAV5S194G showed higher potency in transduction of photoreceptors than native AAV5. The GFP expression was predominantly observed in ONL with AAV5 S194G while GFP expression was observed in all layers with AAV5 (a and b). ONL: outer nuclear layer, INL: inner nuclear layer, RGL: retinal ganglion cell layer.

DETAILED DESCRIPTION

Figure 1A:
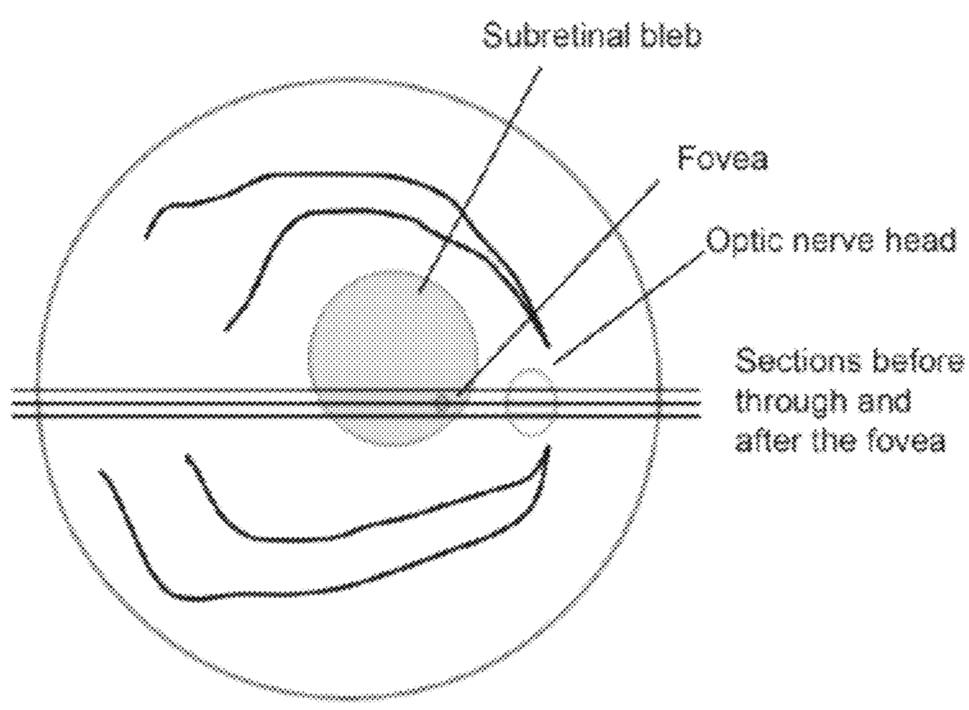
FIG. 1A-FIG. 1B depict AAV2-HBKO mediated GFP Expression in NHP retina following 6 Weeks of post-subretinal injection.

Provided herein are modified AAV capsid proteins conferring improved transduction efficiencies in ocular tissues. Also provided are compositions (e.g., rAAV) comprising the AAV capsid proteins, and nucleic acids encoding the AAV capsid proteins. Also provided are methods of using the compositions described herein for delivering a heterologous nucleic acid into ocular tissues, and methods of improving transduction into ocular tissues, and methods of improving expression of a heterologous nucleic acid in ocular tissues. Also provided herein are methods of treating ocular disorders and conditions.

Generally, nomenclature used in connection with cell and tissue culture, molecular biology, biophysics, immunology, microbiology, genetics, and protein and nucleic acid chemistry described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein is well-known and commonly used in the art. Standard techniques are used for chemical syntheses, chemical analyses, pharmaceutical preparation, formulation, and delivery, and treatment of patients.

The techniques and procedures described or referenced herein are generally well understood and commonly employed using conventional methodology by those skilled in the art, such as, for example, the widely utilized methodologies described in Molecular Cloning: A Laboratory Manual (Sambrook et al., 4th ed., Cold Spring Harbor Laboratory Press, Cold Spring Harbor, N.Y., 2012); Current Protocols in Molecular Biology (F. M. Ausubel, et al. eds., 2003); the series Methods in Enzymology (Academic Press, Inc.); PCR 2: A Practical Approach (M. J. MacPherson, B. D. Hames and G. R. Taylor eds., 1995); Antibodies, A Laboratory Manual (Harlow and Lane, eds., 1988); Culture of Animal Cells: A Manual of Basic Technique and Specialized Applications (R. I. Freshney, 6$^{th}$ ed., J. Wiley and Sons, 2010); Oligonucleotide Synthesis (M. J. Gait, ed., 1984); Methods in Molecular Biology, Humana Press; Cell Biology: A Laboratory Notebook (J. E. Cellis, ed., Academic Press, 1998); Introduction to Cell and Tissue Culture (J. P. Mather and P. E. Roberts, Plenum Press, 1998); Cell and Tissue Culture: Laboratory Procedures (A. Doyle, J. B.

Griffiths, and D. G. Newell, eds., J. Wiley and Sons, 1993-8); Handbook of Experimental Immunology (D. M. Weir and C. C. Blackwell, eds., 1996); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Ausubel et al., eds., J. Wiley and Sons, 2002); Immunobiology (C. A. Janeway et al., 2004); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane, Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J.B. Lippincott Company, 2011).

Unless otherwise defined herein, scientific and technical terms used herein have the meanings that are commonly understood by those of ordinary skill in the art. In the event of any latent ambiguity, definitions provided herein take precedence over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the invention may be more readily understood, certain terms are first defined.

As used herein, the term "vector" refers to any vehicle for the cloning of and/or transfer of a nucleic acid into a host cell. A vector can be a replicon to which another nucleic acid segment can be attached so as to bring about the replication of the attached segment. A "replicon" refers to any genetic element (e.g., plasmid, phage, cosmid, chromosome, virus) that functions as an autonomous unit of replication in vivo, i.e., capable of replication under its own control. The term "vector" includes both viral and nonviral vehicles for introducing the nucleic acid into a cell in vitro, ex vivo or in vivo. A large number of vectors are known and used in the art including, for example, plasmids, modified eukaryotic viruses, or modified bacterial viruses. Insertion of a polynucleotide into a suitable vector can be accomplished by ligating the appropriate polynucleotide fragments into a chosen vector that has complementary cohesive termini.

As used herein, the term "polynucleotide" or "nucleic acid" refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate (P—$NH_2$) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

As used herein, the term "recombinant viral vector" refers to a recombinant polynucleotide vector comprising one or more heterologous sequences (i.e., nucleic acid sequence not of viral origin). In the case of recombinant AAV vectors, the recombinant nucleic acid is flanked by at least one inverted terminal repeat sequence (ITR). In some embodiments, the recombinant nucleic acid is flanked by two ITRs.

As used herein, the term a "recombinant AAV vector (rAAV vector)" refers to a polynucleotide vector comprising one or more heterologous sequences (i.e., nucleic acid sequence not of AAV origin) that are flanked by at least one AAV inverted terminal repeat sequence (ITR). Such rAAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). When a rAAV vector is incorporated into a larger polynucleotide (e.g., in a chromosome or in another vector such as a plasmid used for cloning or transfection), then the rAAV vector may be referred to as a "pro-vector" which can be "rescued" by replication and encapsidation in the presence of AAV packaging functions and suitable helper functions. A rAAV vector can be in any of a number of forms, including, but not limited to, plasmids, linear artificial chromosomes, complexed with lipids, encapsulated within liposomes, and encapsidated in a viral particle, e.g., an AAV particle. A rAAV vector can be packaged into an AAV virus capsid to generate a "recombinant adeno-associated viral particle (rAAV particle)".

As used herein, the term an "rAAV virus" or "rAAV viral particle" refers to a viral particle composed of at least one AAV capsid protein and an encapsidated rAAV vector genome.

As used herein, the term "heterologous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector is a heterologous nucleotide sequence with respect to the vector.

As used herein, the term "transgene" refers to a polynucleotide that is introduced into a cell and is capable of being transcribed into RNA and optionally, translated and/or expressed under appropriate conditions. In aspects, it confers a desired property to a cell into which it was introduced, or otherwise leads to a desired therapeutic or diagnostic outcome. In another aspect, it may be transcribed into a molecule that mediates RNA interference, such as miRNA, siRNA, or shRNA.

As used herein, the terms "genome particles (gp)," "genome equivalents," or "genome copies" as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) Hum. Gene Ther., 10:1031-1039; Veldwijk et al. (2002) Mol. Ther., 6:272-278.

As used herein, the term "vector genome (vg)" may refer to one or more polynucleotides comprising a set of the polynucleotide sequences of a vector, e.g., a viral vector. A vector genome may be encapsidated in a viral particle. Depending on the particular viral vector, a vector genome may comprise single-stranded DNA, double-stranded DNA, or single-stranded RNA, or double-stranded RNA. A vector genome may include endogenous sequences associated with a particular viral vector and/or any heterologous sequences inserted into a particular viral vector through recombinant techniques. For example, a recombinant AAV vector genome may include at least one ITR sequence flanking a promoter, a stuffer, a sequence of interest (e.g., an RNAi), and a polyadenylation sequence. A complete vector genome may include a complete set of the polynucleotide sequences of a vector. In some embodiments, the nucleic acid titer of a viral vector may be measured in terms of vg/mL. Methods suitable for measuring this titer are known in the art (e.g., quantitative PCR).

As used herein, the terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in Mclaughlin et al. (1988) J. Virol., 62:1963-1973.

As used herein, the term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) Exp. Neurobiol., 144:113-124; or in Fisher et al. (1996) J. Virol, 70:520-532 (LFU assay).

As used herein, the term "inverted terminal repeat" or "ITR" sequence, a term well understood in the art, refers to relatively short sequences found at the termini of viral genomes which are in opposite orientation.

As used herein, the term "AAV inverted terminal repeat (ITR)" sequence, a term well-understood in the art, refers to an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity (designated A, A', B, B', C, C and D regions), allowing intrastrand base-pairing to occur within this portion of the ITR.

As used herein, the term "terminal resolution sequence" or "trs" refers to a sequence in the D region of the AAV ITR that is cleaved by AAV rep proteins during viral DNA replication. A mutant terminal resolution sequence is refractory to cleavage by AAV rep proteins.

As used herein, the term "helper virus" for AAV refers to a virus that allows AAV (which is a defective parvovirus) to be replicated and packaged by a host cell. A number of such helper viruses have been identified, including adenoviruses, herpesviruses and poxviruses such as vaccinia. The adenoviruses encompass a number of different subgroups, although Adenovirus type 5 of subgroup C (Ad5) is most commonly used. Numerous adenoviruses of human, non-human mammalian and avian origin are known and are available from depositories such as the ATCC. Viruses of the herpes family, which are also available from depositories such as ATCC, include, for example, herpes simplex viruses (HSV), Epstein-Barr viruses (EBV), cytomegaloviruses (CMV) and pseudorabies viruses (PRV).

As used herein, the term "percent (%) sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various ways that are within the skill in the art, for instance, using publicly available computer software programs, for example, those described in Current Protocols in Molecular Biology (Ausubel et al., eds., 1987), Supp. 30, section 7.7.18, Table 7.7.1, and including BLAST, BLAST-2, ALIGN or Megalign (DNASTAR) software. An example of an alignment program is ALIGN Plus (Scientific and Educational Software, Pennsylvania). Those skilled in the art can determine appropriate parameters for measuring alignment, including any algorithms needed to achieve maximal alignment over the full length of the sequences being compared. For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z, where W is the number of nucleotides scored as identical matches by the sequence alignment program in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

As used herein, the term "isolated" molecule (e.g., nucleic acid or protein) or cell means it has been identified and separated and/or recovered from a component of its natural environment.

As used herein, the term "effective amount" is an amount sufficient to effect beneficial or desired results, including clinical results (e.g., amelioration of symptoms, achievement of clinical endpoints, and the like). An effective amount can be administered in one or more administrations. In terms of a disease state, an effective amount is an amount sufficient to ameliorate, stabilize, or delay development of a disease.

As used herein, the term "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, the term "treatment" refers to an approach for obtaining beneficial or desired clinical results. For purposes of this invention, beneficial or desired clinical results include, but are not limited to, alleviation of symptoms, diminishment of extent of disease, stabilized (e.g., not worsening) state of disease, preventing spread (e.g., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment. The term "treat" is the verb form of "treatment".

As used herein, the term "prophylactic treatment" refers to treatment, wherein an individual is known or suspected to have or be at risk for having a disorder but has displayed no symptoms or minimal symptoms of the disorder. An individual undergoing prophylactic treatment may be treated prior to onset of symptoms.

As used herein, a "therapeutic" agent (e.g., a therapeutic polypeptide, nucleic acid, or transgene) is one that provides a beneficial or desired clinical result, such as the exemplary clinical results described above. As such, a therapeutic agent may be used in a treatment as described above.

As used herein, the term "central retina" refers to the outer macula and/or inner macula and/or the fovea. The term "central retina cell types" as used herein refers to cell types of the central retina, such as, for example, Retinal Pigment Epithelium (RPE) and photoreceptor cells.

As used herein, the term "macula" refers to a region of the central retina in primates that contains a higher relative concentration of photoreceptor cells, specifically rods and cones, compared to the peripheral retina. The term "outer macula" as used herein may also be referred to as the "peripheral macula". The term "inner macula" as used herein may also be referred to as the "central macula".

As used herein, the term "fovea" refers to a small region in the central retina of primates of approximately equal to or less than 0.5 mm in diameter that contains a higher relative concentration of photoreceptor cells, specifically cones, when compared to the peripheral retina and the macula.

As used herein, the term "subretinal space" as refers to the location in the retina between the photoreceptor cells and the retinal pigment epithelium cells. The subretinal space may be a potential space, such as prior to any subretinal injection of fluid. The subretinal space may also contain a fluid that is injected into the potential space. In this case, the fluid is "in contact with the subretinal space." Cells that are "in contact with the subretinal space" include the cells that border the subretinal space, such as RPE and photoreceptor cells.

As used herein, the term "bleb" refers to a fluid space within the subretinal space of an eye. A bleb of the invention may be created by a single injection of fluid into a single space, by multiple injections of one or more fluids into the same space, or by multiple injections into multiple spaces, which when repositioned create a total fluid space useful for achieving a therapeutic effect over the desired portion of the subretinal space.

As used herein, the term "cornea" refers to the transparent front part of the eye that covers the iris, pupil, and anterior chamber.

Modified AAV Capsid Proteins

Gene therapy protocols for disorders of the eye require the localized delivery of the vector to the cells in the eye (e.g., cells of the retina). The cells that will be the treatment target in these diseases may include, inter alia, one or more cells of the eye (e.g., photoreceptors, corneal endothelial cells, etc.). The methods described herein are based, at least in part, on the discovery of specific modifications to AAV capsid proteins (e.g., AAV capsid proteins comprising one or more amino acid substitutions at one or more positions) allow for widespread vector distribution among ocular cells. As such, these capsids may be particularly advantageous for delivering a heterologous nucleic acid to the eye of an individual, improving rAAV transduction of cells following delivery of a rAAV particle to the eye of an individual, improving expression of a heterologous nucleic acid following delivery of rAAV particles to the eye of an individual, and/or treating a disorder of the eye of an individual using rAAV particles.

The AAV capsid (e.g., AAV1, AAV2, AAV4, AAV5, AAV6, AAV7, AAV8, AAV9, etc.) is composed of the three structural proteins VP1, VP2 and VP3, which are expressed from the same open reading frame in an approximate stoichiometry of 1:1:10, with an alternative start codon for VP2 and VP3. The capsid proteins share most of their amino acid sequence; VP1 and VP2 differ from VP3 by a shared N-terminal extension of approximately 65 amino acids, depending on the serotype, with VP1 containing an additional ~135 unique amino acids (McPherson & Rose. J Virol (1983) 46:523-529). VP1 is required for viral infectivity, in part due to the presence of a highly conserved, N terminal phospholipase A2 (sPLA2) homology domain, (amino acid 52-97), that is buried within the capsid interior but becomes externalized through pores found at the 5-fold symmetry axis following a conformational change in the acidic endosomal compartment. While VP2 is dispensable for capsid assembly and infectivity of the virus, any deletion or mutation in VP1 that results in loss of the phospholipase A2 (PLA2) catalytic domain and its activity, results in a significantly reduced AAV infectivity (Girod et al. Journal of General Virology (2002), 83:973-9).

In addition, it has been postulated that other signals affecting infectivity might be located on the VP1-unique region of AAV-2, which has been reported for several autonomous parvovirus capsid proteins. A direct liquid chromatography/mass spectrometry (LC/MS) intact protein analysis to characterize viral capsid proteins has been developed. Using this method, the complete characterization of the constituent viral capsid proteins of several AAV vectors, including their sequences and post-translational modifications (PTMs) can be determined. The N termini of all VPs of six serotypes analyzed (AAV1, 2, 5, 7, 9 & rh10), was confirmed to start at one residue after the predicted N termini based on DNA sequences, with one exception the VP3 of AAV7. Additionally, the VP1 and VP3 of AAV serotypes 1, 2, 5, 7, 9 & rh10, were shown to contain an N terminal acetylation. Although N terminal acetylation of proteins is a widely known phenomenon, the biological significance of N-terminal acetylation of viral capsid proteins is not well understood. See, PCT publication no. WO2018/035059, the disclosure of which is herein incorporated by reference in its entirety.

In one aspect, provided herein are modified AAV capsid proteins comprising substitutions that confer improved transduction in retinal cells. For example, substitutions that preserve VP1 N terminal acetylation and reduce VP3 N terminal acetylation result in a significant improvement in retinal transduction compared to a parental AAV capsid protein. Accordingly, without being bound to any theory, it is believed that such substitutions (e.g., that preserve VP1 N terminal acetylation and reduce VP3 N terminal acetylation) will confer significant improvement in retinal transduction of AAV capsid proteins compared to the parental AAV capsid protein In certain embodiments, substitutions in an AAV5 capsid protein that preserve VP1 N terminal acetylation and reduce VP3 N terminal acetylation result in a significant improvement in retinal transduction compared to a parental AAV5 capsid protein. In certain embodiments, the modified AAV5 capsid protein comprises an amino acid substitution at position S194 according to VP1 numbering. In certain embodiments, provided herein is a modified AAV5 capsid protein comprising a glycine (G) substituting the serine(S) at amino acid position 194 (S194G) according to VP1 numbering. It is readily appreciated by those of skill in the art that such a substitution can be transferred to a capsid protein of any AAV serotype, and the conferred transduction qualities would be expected to transfer to capsid proteins of other AAV serotypes. The skilled artisan will be able to identify corresponding amino acid positions in other AAV serotypes using methods known in the art, e.g., by sequence alignment.

Modifications to, e.g., AAV receptor binding, surface charge, and capsid protein post-translational modifications can confer novel tropism and transduction of certain cell types. For example, improved transduction performance of the AAV2HBKO variant in the context of the mouse retina and CNS has been shown. See, Sullivan et al. (2018) Gen. Ther. 25:205-219. The AAV2HBKO variant has key surface arginines mutated in regions of the capsid that facilitate the binding of AAV2 to its cognate receptor, heparin sulfate proteoglycan. This heparin binding knock out variant demonstrated novel transduction patterns in the mouse CNS and retina. See, PCT publication no. WO2015/168666, the disclosure of which is hereby incorporated herein by reference in its entirety. Thus, the AAV2HBKO variant revealed the importance of arginines, and by extension capsid surface charge, on transduction activity in the retina.

In one aspect, provided herein are modified AAV capsid proteins comprising substitutions that confer novel tropism and improved transduction activity in corneal endothelial cells. For example, it was shown that the addition of arginine (R) residues impacted the tropism and transduction activity of AAV5, which has relatively few surface arginines compared to AAV2. Accordingly, without being bound to any theory, it is believed that introduction of arginines at key surface residues will confer significant improvement in corneal endothelial cell transduction of AAV capsid proteins compared to the parental AAV capsid protein In certain embodiments, substitutions in an AAV5 capsid protein that introduce arginines at key surface residues result in a significant improvement in corneal endothelial cell transduction compared to a parental AAV5 capsid protein. In certain embodiments, the modified AAV5 capsid protein comprises an amino acid substitution at positions G474, N564, and/or N573 according to VP1 numbering. In certain embodiments, provided herein is a modified AAV5 capsid protein comprising an arginine (R) substituting the glycine (G) at amino acid position 474 (G474R) according to VP1 numbering. In certain embodiments, provided herein is a modified AAV5 capsid protein comprising an arginine (R) substituting the asparagine (N) at amino acid position 564 (N564R) according to VP1 numbering. In certain embodiments, provided herein is a modified AAV5 capsid protein comprising an arginine (R) substituting the asparagine (N) at amino acid position 573 (N573R) according to VP1 numbering. It is readily appreciated by those of skill in the art that such a substitution can be transferred to a capsid protein of any AAV serotype, and the conferred transduction qualities would be expected to transfer to capsid proteins of other AAV serotypes. The skilled artisan will be able to identify corresponding amino acid positions in other AAV serotypes using methods known in the art, e.g., by sequence alignment.

Accordingly, in one aspect, provided herein is a polypeptide (e.g., an AAV capsid protein) comprising an amino acid substitution at one or more positions corresponding to amino acids S194, G474, N564, and/or N573, wherein numbering of the positions is based on VP1 numbering of AAV5. In certain embodiments, numbering of the positions is based on the amino acid sequence of the wild-type AAV5 VP1 as set forth in SEQ ID NO:1. As such, in certain embodiments, provided herein is a polypeptide (e.g., an AAV capsid protein) comprising an amino acid substitution at one or more positions corresponding to amino acids S194, G474, N564, and/or N573, wherein numbering of the positions is based on the amino acid sequence of the wild-type AAV5 VP1 as set forth in SEQ ID NO:1. In certain embodiments, provided herein is a modified capsid protein comprising an amino acid substitution at one or more positions corresponding to amino acids S194, G474, N564, and/or N573, wherein numbering of the positions is based on VP1 numbering of AAV5. In certain embodiments, numbering of the positions is based on the amino acid sequence of the wild-type AAV5 VP1 as set forth in SEQ ID NO:1. As such, in certain embodiments, provided herein is a modified capsid protein comprising an amino acid substitution at one or more positions corresponding to amino acids S194, G474, N564, and/or N573, wherein numbering of the positions is based on the amino acid sequence of the wild-type AAV5 VP1 as set forth in SEQ ID NO:1.

In certain embodiments, the modified capsid protein comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity with the amino acid sequence set forth in SEQ ID NO:1. In certain embodiments, the modified capsid protein comprises an amino acid sequence having at least 95% sequence identity with the amino acid sequence set forth in SEQ ID NO:1. In certain embodiments, the modified capsid protein comprises an amino acid sequence having at least 99% sequence identity with the amino acid sequence set forth in SEQ ID NO:1.

In certain embodiments, provided herein is a modified capsid protein comprising an amino acid substitution at the position corresponding to amino acid S194, wherein numbering of the position is based on the amino acid sequence of the wild-type AAV5 VP1 as set forth in SEQ ID NO:1. In certain embodiments, the amino acid in the modified capsid protein corresponding to amino acid 194 is G. In certain embodiments, the modified capsid protein comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity with the amino acid sequence set forth in SEQ ID NO:3, wherein the amino acid in the capsid protein corresponding to amino acid 194 of SEQ ID NO:3 is G. In certain embodiments, the modified capsid protein comprises the amino acid sequence set forth in SEQ ID NO:3. In certain embodiments, the amino acid sequence of the modified capsid protein consists of the amino acid sequence set forth in SEQ ID NO:3.

In certain embodiments, provided herein is a modified capsid protein comprising an amino acid substitution at the position corresponding to amino acid G474, wherein numbering of the position is based on the amino acid sequence of the wild-type AAV5 VP1 as set forth in SEQ ID NO:1. In certain embodiments, the amino acid in the modified capsid protein corresponding to amino acid 474 is R. In certain embodiments, the modified capsid protein comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity with the amino acid sequence set forth in SEQ ID NO:5, wherein the amino acid in the capsid protein corresponding to amino acid 474 of SEQ ID NO:5 is R. In certain embodiments, the modified capsid protein comprises the amino acid sequence set forth in SEQ ID NO:5. In certain embodiments, the amino acid sequence of the modified capsid protein consists of the amino acid sequence set forth in SEQ ID NO:5.

In certain embodiments, provided herein is a modified capsid protein comprising an amino acid substitution at the position corresponding to amino acid N564, wherein numbering of the position is based on the amino acid sequence of the wild-type AAV5 VP1 as set forth in SEQ ID NO:1. In certain embodiments, the amino acid in the modified capsid protein corresponding to amino acid 564 is R. In certain embodiments, the modified capsid protein comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity with the amino acid sequence set forth in SEQ ID NO:7, wherein the amino acid in the capsid protein corresponding to amino acid 564 of SEQ ID NO:7 is R. In certain embodiments, the modified capsid protein comprises the amino acid sequence set forth in SEQ ID NO:7. In certain embodiments, the amino acid sequence of the modified capsid protein consists of the amino acid sequence set forth in SEQ ID NO:7.

In certain embodiments, provided herein is a modified capsid protein comprising an amino acid substitution at the position corresponding to amino acid N573, wherein numbering of the position is based on the amino acid sequence of the wild-type AAV5 VP1 as set forth in SEQ ID NO:1. In certain embodiments, the amino acid in the modified capsid protein corresponding to amino acid 573 is R. In certain embodiments, the modified capsid protein comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity with the amino acid sequence set forth in SEQ ID NO:9, wherein the amino acid in the capsid protein corresponding to amino acid 573 of SEQ ID NO:9 is R. In certain embodiments, the modified capsid protein comprises the amino acid sequence set forth in SEQ ID NO:9. In certain embodiments, the amino acid sequence of the modified capsid protein consists of the amino acid sequence set forth in SEQ ID NO:9.

Accordingly, in certain embodiments, provided herein is a modified adeno-associated virus (AAV) capsid protein comprising a G at the position corresponding to amino acid 194; an R at the position corresponding to amino acid 474; an R at the position corresponding to amino acid 564; and/or an R at the position corresponding to amino acid 573, wherein numbering of the position is based on VP1 numbering of AAV5 (e.g., based on VP1 number of the amino acid sequence set forth in SEQ ID NO:1). In certain embodiments, the modified capsid protein comprises a G at the position corresponding to amino acid 194, wherein numbering of the position is based on VP1 numbering of AAV5 (e.g., based on VP1 number of the amino acid sequence set forth in SEQ ID NO:1). In certain embodiments, the modified capsid protein comprises a R at the position corresponding to amino acid 474, wherein numbering of the position is based on VP1 numbering of AAV5 (e.g., based on VP1 number of the amino acid sequence set forth in SEQ ID NO:1). In certain embodiments, the modified capsid protein comprises a R at the position corresponding to amino acid 564, wherein numbering of the position is based on VP1 numbering of AAV5 (e.g., based on VP1 number of the amino acid sequence set forth in SEQ ID NO:1). In certain embodiments, the modified capsid protein comprises a R at the position corresponding to amino acid 573, wherein numbering of the position is based on VP1 numbering of AAV5 (e.g., based on VP1 number of the amino acid sequence set forth in SEQ ID NO:1).

In certain embodiments, provided herein is a polypeptide (e.g., a modified adeno-associated virus capsid protein) comprising the amino acid sequence set forth in SEQ ID NO: 3. In certain embodiments, provided herein is a polypeptide (e.g., a modified adeno-associated virus capsid protein) consisting of the amino acid sequence set forth in SEQ ID NO: 3. In certain embodiments, provided herein is a polypeptide (e.g., a modified adeno-associated virus capsid protein) comprising the amino acid sequence set forth in SEQ ID NO: 5. In certain embodiments, provided herein is a polypeptide (e.g., a modified adeno-associated virus capsid protein) consisting of the amino acid sequence set forth in SEQ ID NO: 5. In certain embodiments, provided herein is a polypeptide (e.g., a modified adeno-associated virus capsid protein) comprising the amino acid sequence set forth in SEQ ID NO: 7. In certain embodiments, provided herein is a polypeptide (e.g., a modified adeno-associated virus capsid protein) consisting of the amino acid sequence set forth in SEQ ID NO: 7. In certain embodiments, provided herein is a polypeptide (e.g., a modified adeno-associated virus capsid protein) comprising the amino acid sequence set forth in SEQ ID NO: 9. In certain embodiments, provided herein is a polypeptide (e.g., a modified adeno-associated virus capsid protein) consisting of the amino acid sequence set forth in SEQ ID NO: 9.

TABLE 1

| AAV Capsid Protein Sequences | | |
|---|---|---|
| AAV5 | AA | MSFVDHPPDWLEEVGEGLREFLGLEAGPPKPKPNQQHQDQARGLVLPGYNYLGPGN<br>GLDRGEPVNRADEVAREHDISYNEQLEAGDNPYLKYNHADAEFQEKLADDTSFGGNLG<br>KAVFQAKKRVLEPFGLVEEGAKTAPTGKRIDDHFPKRKKARTEEDSKPSTSSDAEAGPS<br>GSQQLQIPAQPASSLGADTMSAGGGGPLGDNNQGADGVGNASGDWHCDSTWMGDR<br>VVTKSTRTWVLPSYNNHQYREIKSGSVDGSNANAYFGYSTPWGYFDFNRFHSHWSPR<br>DWQRLINNYWGFRPRSLRVKIFNIQVKEVTVQDSTTTIANNLTSTVQVFTDDDYQLPYV<br>VGNGTEGCLPAFPPQVFTLPQYGYATLNRDNTENPTERSSFFCLEYFPSKMLRTGNNF<br>EFTYNFEEVPFHSSFAPSQNLFKLANPLVDQYLYRFVSTNNTGGVQFNKNLAGRYANT<br>YKNWFPGPMGRTQGWNLGSGVNRASVSAFATTNRMELEGASYQVPPQPNGMTNNL<br>QGSNTYALENTMIFNSQPANPGTTATYLEGNMLITSESETQPVNRVAYNVGGQMATNN<br>QSSTTAPATGTYNLQEIVPGSVWMERDVYLQGPIWAKIPETGAHFHPSPAMGGFGLKH<br>PPPMMLIKNTPVPGNITSFSDVPVSSFITQYSTGQVTVEMEWELKKENSKRWNPEIQYT<br>NNYNDPQFVDFAPDSTGEYRTTRPIGTRYLTRPL (SEQ ID NO: 1) |
| | NA | ATGTCTTTTGTTGATCACCCTCCAGATTGGTTGGAAGAAGTTGGTGAAGGTCTTCGC<br>GAGTTTTTGGGCCTTGAAGCGGGCCCACCGAAACCAAAACCCAATCAGCAGCATCA<br>AGATCAAGCCCGTGGTCTTGTGCTGCCTGGTTATAACTATCTCGGACCCGGAAACG<br>GTCTCGATCGAGGAGAGCCTGTCAACAGGGCAGACGAGGTCGCGCGAGAGCACG<br>ACATCTCGTACAACGAGCAGCTTGAGGCGGGAGACAACCCCTACCTCAAGTACAAC<br>CACGCGGACGCCGAGTTTCAGGAGAAGCTCGCCGACGACACATCCTTCGGGGGAA<br>ACCTCGGAAAGGCAGTCTTTCAGGCCAAGAAAAGGGTTCTCGAACCTTTTGGCCTG<br>GTTGAAGAGGGTGCTAAGACGGCCCCTACCGGAAAGCGGATAGACGACCACTTTC<br>CAAAAAGAAAGAAGGCTCGGACCGAAGAGGACTCCAAGCCTTCCACCTCGTCAGAC<br>GCCGAAGCTGGACCCAGCGGATCCCAGCAGCTGCAAATCCCAGCCCAACCAGCCT<br>CAAGTTTGGGAGCTGATACAATGTCTGCGGGAGGTGGCGGCCCATTGGGCGACAA<br>TAACCAAGGTGCCGATGGAGTGGGCAATGCCTCGGGAGATTGGCATTGCGATTCC<br>ACGTGGATGGGGGACAGAGTCGTCACCAAGTCCACCCGAACCTGGGTGCTGCCCA<br>GCTACAACAACCACCAGTACCGAGAGATCAAAAGCGGCTCCGTCGACGGAAGCAA<br>CGCCAACGCCTACTTTGGATACAGCACCCCCTGGGGGTACTTTGACTTTAACCGCT<br>TCCACAGCCACTGGAGCCCCCGAGACTGGCAAAGACTCATCAACAACTACTGGGG<br>CTTCAGACCCCGGTCCCTCAGAGTCAAAATCTTCAACATTCAAGTCAAAGAGGTCAC<br>GGTGCAGGACTCCACCACCACCATCGCCAACAACCTCACCTCCACCGTCCAAGTGT<br>TTACGGACGACGACTACCAGCTGCCCTACGTCGTCGGCAACGGGACCGAGGGATG<br>CCTGCCGGCCTTCCCTCCGCAGGTCTTTACGCTGCCGCAGTACGGTTACGCGACG<br>CTGAACCGCGACAACACAGAAAATCCCACCGAGAGGAGCAGCTTCTTCTGCCTAGA<br>GTACTTTCCCAGCAAGATGCTGAGAACGGGCAACAACTTTGAGTTTACCTACAACTT<br>TGAGGAGGTGCCCTTCCACTCCAGCTTCGCTCCCAGTCAGAACCTGTTCAAGCTGG<br>CCAACCCGCTGGTGGACCAGTACTTGTACCGCTTCGTGAGCACAAATAACACTGGC<br>GGAGTCCAGTTCAACAAGAACCTGGCCGGGAGATACGCCAACACCTACAAAAACTG<br>GTTCCCGGGGCCCATGGGCCGAACCCAGGGCTGGAACCTGGGCTCCGGGGTCAA<br>CCGCGCCAGTGTCAGCGCCTTCGCCACGACCAATAGGATGGAGCTCGAGGGCGC<br>GAGTTACCAGGTGCCCCCGCAGCCGAACGGCATGACCAACAACCTCCAGGGCAGC<br>AACACCTATGCCCTGGAGAACACTATGATCTTCAACAGCCAGCCGGCGAACCCGGG<br>CACCACCGCCACGTACCTCGAGGGCAACATGCTCATCACCAGCGAGAGCGAGACG<br>CAGCCGGTGAACCGCGTGGCGTACAACGTCGGCGGGCAGATGGCCACCAACAAC<br>CAGAGCTCCACCACTGCCCCCGCGACCGGCACGTACAACCTCCAGGAAATCGTGC<br>CCGGCAGCGTGTGGATGGAGAGGGACGTGTACCTCCAAGGACCCATCTGGGCCAA<br>GATCCCAGAGACGGGGGCGCACTTTCACCCCTCTCCGGCCATGGGCGGATTCGGA<br>CTCAAACACCCACCGCCCATGATGCTCATCAAGAACACGCCTGTGCCCGGAAATAT<br>CACCAGCTTCTCGGACGTGCCCGTCAGCAGCTTCATCACCCAGTACAGCACCGGG<br>CAGGTCACCGTGGAGATGGAGTGGGAGCTCAAGAAGGAAAACTCCAAGAGGTGGA<br>ACCCAGAGATCCAGTACACAAACAACTACAACGACCCCCAGTTTGTGGACTTTGCC<br>CCGGACAGCACCGGGGAATACAGAACCACCAGACCTATCGGAACCCGATACCTTA<br>CCCGACCCCTT (SEQ ID NO: 2) |
| AAV5-<br>S194G | AA | MSFVDHPPDWLEEVGEGLREFLGLEAGPPKPKPNQQHQDQARGLVLPGYNYLGPGN<br>GLDRGEPVNRADEVAREHDISYNEQLEAGDNPYLKYNHADAEFQEKLADDTSFGGNLG<br>KAVFQAKKRVLEPFGLVEEGAKTAPTGKRIDDHFPKRKKARTEEDSKPSTSSDAEAGPS<br>GSQQLQIPAQPASSLGADTMGAGGGGPLGDNNQGADGVGNASGDWHCDSTWMGDR<br>VVTKSTRTWVLPSYNNHQYREIKSGSVDGSNANAYFGYSTPWGYFDFNRFHSHWSPR<br>DWQRLINNYWGFRPRSLRVKIFNIQVKEVTVQDSTTTIANNLTSTVQVFTDDDYQLPYV<br>VGNGTEGCLPAFPPQVFTLPQYGYATLNRDNTENPTERSSFFCLEYFPSKMLRTGNNF<br>EFTYNFEEVPFHSSFAPSQNLFKLANPLVDQYLYRFVSTNNTGGVQFNKNLAGRYANT<br>YKNWFPGPMGRTQGWNLGSGVNRASVSAFATTNRMELEGASYQVPPQPNGMTNNL<br>QGSNTYALENTMIFNSQPANPGTTATYLEGNMLITSESETQPVNRVAYNVGGQMATNN<br>QSSTTAPATGTYNLQEIVPGSVWMERDVYLQGPIWAKIPETGAHFHPSPAMGGFGLKH<br>PPPMMLIKNTPVPGNITSFSDVPVSSFITQYSTGQVTVEMEWELKKENSKRWNPEIQYT<br>NNYNDPQFVDFAPDSTGEYRTTRPIGTRYLTRPL (SEQ ID NO: 3) |
| | NA | ATGTCTTTTGTTGATCACCCTCCAGATTGGTTGGAAGAAGTTGGTGAAGGTCTTCGC<br>GAGTTTTTGGGCCTTGAAGCGGGCCCACCGAAACCAAAACCCAATCAGCAGCATCA<br>AGATCAAGCCCGTGGTCTTGTGCTGCCTGGTTATAACTATCTCGGACCCGGAAACG<br>GTCTCGATCGAGGAGAGCCTGTCAACAGGGCAGACGAGGTCGCGCGAGAGCACG<br>ACATCTCGTACAACGAGCAGCTTGAGGCGGGAGACAACCCCTACCTCAAGTACAAC<br>CACGCGGACGCCGAGTTTCAGGAGAAGCTCGCCGACGACACATCCTTCGGGGGAA<br>ACCTCGGAAAGGCAGTCTTTCAGGCCAAGAAAAGGGTTCTCGAACCTTTTGGCCTG<br>GTTGAAGAGGGTGCTAAGACGGCCCCTACCGGAAAGCGGATAGACGACCACTTTC<br>CAAAAAGAAAGAAGGCTCGGACCGAAGAGGACTCCAAGCCTTCCACCTCGTCAGAC<br>GCCGAAGCTGGACCCAGCGGATCCCAGCAGCTGCAAATCCCAGCCCAACCAGCCT<br>CAAGTTTGGGAGCTGATACAATGGGTGCGGGAGGTGGCGGCCCATTGGGCGACAA |

TABLE 1-continued

| AAV Capsid Protein Sequences | | |
|---|---|---|
| | | TAACCAAGGTGCCGATGGAGTGGGCAATGCCTCGGGAGATTGGCATTGCGATTCC<br>ACGTGGATGGGGGACAGAGTCGTCACCAAGTCCACCCGAACCTGGGTGCTGCCCA<br>GCTACAACAACCACCAGTACCGAGAGATCAAAAGCGGCTCCGTCGACGGAAGCAA<br>CGCCAACGCCTACTTTGGATACAGCACCCCCTGGGGGTACTTTGACTTTAACCGCT<br>TCCACAGCCACTGGAGCCCCCGAGACTGGCAAAGACTCATCAACAACTACTGGGG<br>CTTCAGACCCCGGTCCCTCAGAGTCAAAATCTTCAACATTCAAGTCAAAGAGGTCAC<br>GGTGCAGGACTCCACCACCACCATCGCCAACAACCTCACCTCCACCGTCCAAGTGT<br>TTACGGACGACGACTACCAGCTGCCCTACGTCGTCGGCAACGGGACCGAGGGATG<br>CCTGCCGGCCTTCCCTCCGCAGGTCTTTACGCTGCCGCAGTACGGTTACGCGACG<br>CTGAACCGCGACAACACAGAAAATCCCACCGAGAGGAGCAGCTTCTTCTGCCTAGA<br>GTACTTTCCCAGCAAGATGCTGAGAACGGGCAACAACTTTGAGTTTACCTACAACTT<br>TGAGGAGGTGCCCTTCCACTCCAGCTTCGCTCCCAGTCAGAACCTGTTCAAGCTGG<br>CCAACCCGCTGGTGGACCAGTACTTGTACCGCTTCGTGAGCACAAATAACACTGGC<br>GGAGTCCAGTTCAACAAGAACCTGGCCGGGAGATACGCCAACACCTACAAAAACTG<br>GTTCCCGGGGCCCATGGGCCGAACCCAGGGCTGGAACCTGGGCTCCGGGGTCAA<br>CCGCGCCAGTGTCAGCGCCTTCGCCACGACCAATAGGATGGAGCTCGAGGGCGC<br>GAGTTACCAGGTGCCCCCGCAGCCGAACGGCATGACCAACAACCTCCAGGGCAGC<br>AACACCTATGCCCTGGAGAACACTATGATCTTCAACAGCCAGCCGGCGAACCCGGG<br>CACCACCGCCACGTACCTCGAGGGCAACATGCTCATCACCAGCGAGAGCGAGACG<br>CAGCCGGTGAACCGCGTGGCGTACAACGTCGGCGGGCAGATGGCCACCAACAAC<br>CAGAGCTCCACCACTGCCCCCGCGACCGGCACGTACAACCTCCAGGAAATCGTGC<br>CCGGCAGCGTGTGGATGGAGAGGGACGTGTACCTCCAAGGACCCATCTGGGCCAA<br>GATCCCAGAGACGGGGGCGCACTTTCACCCCTCTCCGGCCATGGGCGGATTCGGA<br>CTCAAACACCCACCGCCCATGATGCTCATCAAGAACACGCCTGTGCCCGGAAATAT<br>CACCAGCTTCTCGGACGTGCCCGTCAGCAGCTTCATCACCCAGTACAGCACCGGG<br>CAGGTCACCGTGGAGATGGAGTGGGAGCTCAAGAAGGAAAACTCCAAGAGGTGGA<br>ACCCAGAGATCCAGTACACAAACAACTACAACGACCCCCAGTTTGTGGACTTTGCC<br>CCGGACAGCACCGGGGAATACAGAACCACCAGACCTATCGGAACCCGATACCTTA<br>CCCGACCCCTT (SEQ ID NO: 4) |
| AAV5-<br>G474R | AA | MSFVDHPPDWLEEVGEGLREFLGLEAGPPKPKPNQQHQDQARGLVLPGYNYLGPGN<br>GLDRGEPVNRADEVAREHDISYNEQLEAGDNPYLKYNHADAEFQEKLADDTSFGGNLG<br>KAVFQAKKRVLEPFGLVEEGAKTAPTGKRIDDHFPKRKKARTEEDSKPSTSSDAEAGPS<br>GSQQLQIPAQPASSLGADTMSAGGGGPLGDNNQGADGVGNASGDWHCDSTWMGDR<br>VVTKSTRTWVLPSYNNHQYREIKSGSVDGSNANAYFGYSTPWGYFDFNRFHSHWSPR<br>DWQRLINNYWGFRPRSLRVKIFNIQVKEVTVQDSTTTIANNLTSTVQVFTDDDYQLPYV<br>VGNGTEGCLPAFPPQVFTLPQYGYATLNRDNTENPTERSSFFCLEYFPSKMLRTGNNF<br>EFTYNFEEVPFHSSFAPSQNLFKLANPLVDQYLYRFVSTNNTGGVQFNKNLAGRYANT<br>YKNWFPGPMGRTQRWNLGSGVNRASVSAFATTNRMELEGASYQVPPQPNGMTNNL<br>QGSNTYALENTMIFNSQPANPGTTATYLEGNMLITSESETQPVNRVAYNVGGQMATNN<br>QSSTTAPATGTYNLQEIVPGSVWMERDVYLQGPIWAKIPETGAHFHPSPAMGGFGLKH<br>PPPMMLIKNTPVPGNITSFSDVPVSSFITQYSTGQVTVEMEWELKKENSKRWNPEIQYT<br>NNYNDPQFVDFAPDSTGEYRTTRPIGTRYLTRPL (SEQ ID NO: 5) |
| | NA | ATGTCTTTTGTTGATCACCCTCCAGATTGGTTGGAAGAAGTTGGTGAAGGTCTTCGC<br>GAGTTTTTGGGCCTTGAAGCGGGCCCACCGAAACCAAAACCCAATCAGCAGCATCA<br>AGATCAAGCCCGTGGTCTTGTGCTGCCTGGTTATAACTATCTCGGACCCGGAAACG<br>GTCTCGATCGAGGAGAGCCTGTCAACAGGGCAGACGAGGTCGCGCGAGAGCACG<br>ACATCTCGTACAACGAGCAGCTTGAGGCGGGAGACAACCCCTACCTCAAGTACAAC<br>CACGCGGACGCCGAGTTTCAGGAGAAGCTCGCCGACGACACATCCTTCGGGGGAA<br>ACCTCGGAAAGGCAGTCTTTCAGGCCAAGAAAAGGGTTCTCGAACCTTTTGGCCTG<br>GTTGAAGAGGGTGCTAAGACGGCCCCTACCGGAAAGCGGATAGACGACCACTTTC<br>CAAAAAGAAAGAAGGCTCGGACCGAAGAGGACTCCAAGCCTTCCACCTCGTCAGAC<br>GCCGAAGCTGGACCCAGCGGATCCCAGCAGCTGCAAATCCCAGCCCAACCAGCCT<br>CAAGTTTGGGAGCTGATACAATGTCTGCGGGAGGTGGCGGCCCATTGGGCGACAA<br>TAACCAAGGTGCCGATGGAGTGGGCAATGCCTCGGGAGATTGGCATTGCGATTCC<br>ACGTGGATGGGGGACAGAGTCGTCACCAAGTCCACCCGAACCTGGGTGCTGCCCA<br>GCTACAACAACCACCAGTACCGAGAGATCAAAAGCGGCTCCGTCGACGGAAGCAA<br>CGCCAACGCCTACTTTGGATACAGCACCCCCTGGGGGTACTTTGACTTTAACCGCT<br>TCCACAGCCACTGGAGCCCCCGAGACTGGCAAAGACTCATCAACAACTACTGGGG<br>CTTCAGACCCCGGTCCCTCAGAGTCAAAATCTTCAACATTCAAGTCAAAGAGGTCAC<br>GGTGCAGGACTCCACCACCACCATCGCCAACAACCTCACCTCCACCGTCCAAGTGT<br>TTACGGACGACGACTACCAGCTGCCCTACGTCGTCGGCAACGGGACCGAGGGATG<br>CCTGCCGGCCTTCCCTCCGCAGGTCTTTACGCTGCCGCAGTACGGTTACGCGACG<br>CTGAACCGCGACAACACAGAAAATCCCACCGAGAGGAGCAGCTTCTTCTGCCTAGA<br>GTACTTTCCCAGCAAGATGCTGAGAACGGGCAACAACTTTGAGTTTACCTACAACTT<br>TGAGGAGGTGCCCTTCCACTCCAGCTTCGCTCCCAGTCAGAACCTGTTCAAGCTGG<br>CCAACCCGCTGGTGGACCAGTACTTGTACCGCTTCGTGAGCACAAATAACACTGGC<br>GGAGTCCAGTTCAACAAGAACCTGGCCGGGAGATACGCCAACACCTACAAAAACTG<br>GTTCCCGGGGCCCATGGGCCGAACCCAGCGCTGGAACCTGGGCTCCGGGGTCAA<br>CCGCGCCAGTGTCAGCGCCTTCGCCACGACCAATAGGATGGAGCTCGAGGGCGC<br>GAGTTACCAGGTGCCCCCGCAGCCGAACGGCATGACCAACAACCTCCAGGGCAGC<br>AACACCTATGCCCTGGAGAACACTATGATCTTCAACAGCCAGCCGGCGAACCCGGG<br>CACCACCGCCACGTACCTCGAGGGCAACATGCTCATCACCAGCGAGAGCGAGACG<br>CAGCCGGTGAACCGCGTGGCGTACAACGTCGGGGGGCAGATGGCCACCAACAAC<br>CAGAGCTCCACCACTGCCCCCGCGACCGGCACGTACAACCTCCAGGAAATCGTGC<br>CCGGCAGCGTGTGGATGGAGAGGGACGTGTACCTCCAAGGACCCATCTGGGCCAA<br>GATCCCAGAGACGGGGGCGCACTTTCACCCCTCTCCGGCCATGGGCGGATTCGGA<br>CTCAAACACCCACCGCCCATGATGCTCATCAAGAACACGCCTGTGCCCGGAAATAT |

TABLE 1-continued

| | | AAV Capsid Protein Sequences |
|---|---|---|
| | | CACCAGCTTCTCGGACGTGCCCGTCAGCAGCTTCATCACCCAGTACAGCACCGGG<br>CAGGTCACCGTGGAGATGGAGTGGGAGCTCAAGAAGGAAAACTCCAAGAGGTGGA<br>ACCCAGAGATCCAGTACACAAACAACTACAACGACCCCCAGTTTGTGGACTTTGCC<br>CCGGACAGCACCGGGGAATACAGAACCACCAGACCTATCGGAACCCGATACCTTA<br>CCCGACCCCTT (SEQ ID NO: 6) |
| AAV5-N564R | AA | MSFVDHPPDWLEEVGEGLREFLGLEAGPPKPKPNQQHQDQARGLVLPGYNYLGPGN<br>GLDRGEPVNRADEVAREHDISYNEQLEAGDNPYLKYNHADAEFQEKLADDTSFGGNLG<br>KAVFQAKKRVLEPFGLVEEGAKTAPTGKRIDDHFPKRKKARTEEDSKPSTSSDAEAGPS<br>GSQQLQIPAQPASSLGADTMSAGGGGPLGDNNQGADGVGNASGDWHCDSTWMGDR<br>VVTKSTRTWVLPSYNNHQYREIKSGSVDGSNANAYFGYSTPWGYFDFNRFHSHWSPR<br>DWQRLINNYWGFRPRSLRVKIFNIQVKEVTVQDSTTTIANNLTSTVQVFTDDDYQLPYV<br>VGNGTEGCLPAFPPQVFTLPQYGYATLNRDNTENPTERSSFFCLEYFPSKMLRTGNNF<br>EFTYNFEEVPFHSSFAPSQNLFKLANPLVDQYLYRFVSTNNTGGVQFNKNLAGRYANT<br>YKNWFPGPMGRTQGWNLGSGVNRASVSAFATTNRMELEGASYQVPPQPNGMTNNL<br>QGSNTYALENTMIFNSQPANPGTTATYLEGNMLITSESETQPVNRVAYRVGGQMATNN<br>QSSTTAPATGTYNLQEIVPGSVWMERDVYLQGPIWAKIPETGAHFHPSPAMGGFGLKH<br>PPPMMLIKNTPVPGNITSFSDVPVSSFITQYSTGQVTVEMEWELKKENSKRWNPEIQYT<br>NNYNDPQFVDFAPDSTGEYRTTRPIGTRYLTRPL (SEQ ID NO: 7) |
| | NA | ATGTCTTTTGTTGATCACCCTCCAGATTGGTTGGAAGAAGTTGGTGAAGGTCTTCGC<br>GAGTTTTTGGGCCTTGAAGCGGGCCCACCGAAACCAAAACCCAATCAGCAGCATCA<br>AGATCAAGCCCGTGGTCTTGTGCTGCCTGGTTATAACTATCTCGGACCCGGAAACG<br>GTCTCGATCGAGGAGAGCCTGTCAACAGGGCAGACGAGGTCGCGCGAGAGCACG<br>ACATCTCGTACAACGAGCAGCTTGAGGCGGGAGACAACCCCTACCTCAAGTACAAC<br>CACGCGGACGCCGAGTTTCAGGAGAAGCTCGCCGACGACACATCCTTCGGGGGAA<br>ACCTCGGAAAGGCAGTCTTTCAGGCCAAGAAAAGGGTTCTCGAACCTTTTGGCCTG<br>GTTGAAGAGGGTGCTAAGACGGCCCCTACCGGAAAGCGGATAGACGACCACTTTC<br>CAAAAAGAAAGAAGGCTCGGACCGAAGAGGACTCCAAGCCTTCCACCTCGTCAGAC<br>GCCGAAGCTGGACCCAGCGGATCCCAGCAGCTGCAAATCCCAGCCCAACCAGCCT<br>CAAGTTTGGGAGCTGATACAATGTCTGCGGGAGGTGGCGGCCCATTGGGCGACAA<br>TAACCAAGGTGCCGATGGAGTGGGCAATGCCTCGGGAGATTGGCATTGCGATTCC<br>ACGTGGATGGGGGACAGAGTCGTCACCAAGTCCACCCGAACCTGGGTGCTGCCCA<br>GCTACAACAACCACCAGTACCGAGAGATCAAAAGCGGCTCCGTCGACGGAAGCAA<br>CGCCAACGCCTACTTTGGATACAGCACCCCCTGGGGGTACTTTGACTTTAACCGCT<br>TCCACAGCCACTGGAGCCCCCGAGACTGGCAAAGACTCATCAACAACTACTGGGG<br>CTTCAGACCCCGGTCCCTCAGAGTCAAAATCTTCAACATTCAAGTCAAAGAGGTCAC<br>GGTGCAGGACTCCACCACCACCATCGCCAACAACCTCACCTCCACCGTCCAAGTGT<br>TTACGGACGACGACTACCAGCTGCCCTACGTCGTCGGCAACGGGACCGAGGGATG<br>CCTGCCGGCCTTCCCTCCGCAGGTCTTTACGCTGCCGCAGTACGGTTACGCGACG<br>CTGAACCGCGACAACACAGAAAATCCCACCGAGAGGAGCAGCTTCTTCTGCCTAGA<br>GTACTTTCCCAGCAAGATGCTGAGAACGGGCAACAACTTTGAGTTTACCTACAACTT<br>TGAGGAGGTGCCCTTCCACTCCAGCTTCGCTCCCAGTCAGAACCTGTTCAAGCTGG<br>CCAACCCGCTGGTGGACCAGTACTTGTACCGCTTCGTGAGCACAAATAACACTGGC<br>GGAGTCCAGTTCAACAAGAACCTGGCCGGGAGATACGCCAACACCTACAAAAACTG<br>GTTCCCGGGGCCCATGGGCCGAACCCAGGGCTGGAACCTGGGCTCCGGGGTCAA<br>CCGCGCCAGTGTCAGCGCCTTCGCCACGACCAATAGGATGGAGCTCGAGGGCGC<br>GAGTTACCAGGTGCCCCCGCAGCCGAACGGCATGACCAACAACCTCCAGGGCAGC<br>AACACCTATGCCCTGGAGAACACTATGATCTTCAACAGCCAGCCGGCGAACCCGGG<br>CACCACCGCCACGTACCTCGAGGGCAACATGCTCATCACCAGCGAGAGCGAGACG<br>CAGCCGGTGAACCGCGTGGCGTACCGCGTCGGCGGGCAGATGGCCACCAACAAC<br>CAGAGCTCCACCACTGCCCCCGCGACCGGCACGTACAACCTCCAGGAAATCGTGC<br>CCGGCAGCGTGTGGATGGAGAGGGACGTGTACCTCCAAGGACCCATCTGGGCCAA<br>GATCCCAGAGACGGGGGCGCACTTTCACCCCTCTCCGGCCATGGGGGATTCGGA<br>CTCAAACACCCACCGCCCATGATGCTCATCAAGAACACGCCTGTGCCCGGAAATAT<br>CACCAGCTTCTCGGACGTGCCCGTCAGCAGCTTCATCACCCAGTACAGCACCGGG<br>CAGGTCACCGTGGAGATGGAGTGGGAGCTCAAGAAGGAAAACTCCAAGAGGTGGA<br>ACCCAGAGATCCAGTACACAAACAACTACAACGACCCCCAGTTTGTGGACTTTGCC<br>CCGGACAGCACCGGGGAATACAGAACCACCAGACCTATCGGAACCCGATACCTTA<br>CCCGACCCCTT (SEQ ID NO: 8) |
| AAV5-N573R | AA | MSFVDHPPDWLEEVGEGLREFLGLEAGPPKPKPNQQHQDQARGLVLPGYNYLGPGN<br>GLDRGEPVNRADEVAREHDISYNEQLEAGDNPYLKYNHADAEFQEKLADDTSFGGNLG<br>KAVFQAKKRVLEPFGLVEEGAKTAPTGKRIDDHFPKRKKARTEEDSKPSTSSDAEAGPS<br>GSQQLQIPAQPASSLGADTMSAGGGGPLGDNNQGADGVGNASGDWHCDSTWMGDR<br>VVTKSTRTWVLPSYNNHQYREIKSGSVDGSNANAYFGYSTPWGYFDFNRFHSHWSPR<br>DWQRLINNYWGFRPRSLRVKIFNIQVKEVTVQDSTTTIANNLTSTVQVFTDDDYQLPYV<br>VGNGTEGCLPAFPPQVFTLPQYGYATLNRDNTENPTERSSFFCLEYFPSKMLRTGNNF<br>EFTYNFEEVPFHSSFAPSQNLFKLANPLVDQYLYRFVSTNNTGGVQFNKNLAGRYANT<br>YKNWFPGPMGRTQGWNLGSGVNRASVSAFATTNRMELEGASYQVPPQPNGMTNNL<br>QGSNTYALENTMIFNSQPANPGTTATYLEGNMLITSESETQPVNRVAYNVGGQMATNR<br>QSSTTAPATGTYNLQEIVPGSVWMERDVYLQGPIWAKIPETGAHFHPSPAMGGFGLKH<br>PPPMMLIKNTPVPGNITSFSDVPVSSFITQYSTGQVTVEMEWELKKENSKRWNPEIQYT<br>NNYNDPQFVDFAPDSTGEYRTTRPIGTRYLTRPL (SEQ ID NO: 9) |
| | NA | ATGTCTTTTGTTGATCACCCTCCAGATTGGTTGGAAGAAGTTGGTGAAGGTCTTCGC<br>GAGTTTTTGGGCCTTGAAGCGGGCCCACCGAAACCAAAACCCAATCAGCAGCATCA<br>AGATCAAGCCCGTGGTCTTGTGCTGCCTGGTTATAACTATCTCGGACCCGGAAACG<br>GTCTCGATCGAGGAGAGCCTGTCAACAGGGCAGACGAGGTCGCGCGAGAGCACG<br>ACATCTCGTACAACGAGCAGCTTGAGGCGGGAGACAACCCCTACCTCAAGTACAAC |

TABLE 1-continued

| AAV Capsid Protein Sequences |
| --- |
| CACGCGGACGCCGAGTTTCAGGAGAAGCTCGCCGACGACACATCCTTCGGGGGAA<br>ACCTCGGAAAGGCAGTCTTTCAGGCCAAGAAAAGGGTTCTCGAACCTTTTGGCCTG<br>GTTGAAGAGGGTGCTAAGACGGCCCCTACCGGAAAGCGGATAGACGACCACTTTC<br>CAAAAAGAAAGAAGGCTCGGACCGAAGAGGACTCCAAGCCTTCCACCTCGTCAGAC<br>GCCGAAGCTGGACCCAGCGGATCCCAGCAGCTGCAAATCCCAGCCCAACCAGCCT<br>CAAGTTTGGGAGCTGATACAATGTCTGCGGGAGGTGGCGGCCCATTGGGCGACAA<br>TAACCAAGGTGCCGATGGAGTGGGCAATGCCTCGGGAGATTGGCATTGCGATTCC<br>ACGTGGATGGGGGACAGAGTCGTCACCAAGTCCACCCGAACCTGGGTGCTGCCCA<br>GCTACAACAACCACCAGTACCGAGAGATCAAAAGCGGCTCCGTCGACGGAAGCAA<br>CGCCAACGCCTACTTTGGATACAGCACCCCCTGGGGGTACTTTGACTTTAACCGCT<br>TCCACAGCCACTGGAGCCCCCGAGACTGGCAAAGACTCATCAACAACTACTGGGG<br>CTTCAGACCCCGGTCCCTCAGAGTCAAAATCTTCAACATTCAAGTCAAAGAGGTCAC<br>GGTGCAGGACTCCACCACCACCATCGCCAACAACCTCACCTCCACCGTCCAAGTGT<br>TTACGGACGACGACTACCAGCTGCCCTACGTCGTCGGCAACGGGACCGAGGGATG<br>CCTGCCGGCCTTCCCTCCGCAGGTCTTTACGCTGCCGCAGTACGGTTACGCGACG<br>CTGAACCGCGACAACACAGAAAATCCCACCGAGAGGAGCAGCTTCTTCTGCCTAGA<br>GTACTTTCCCAGCAAGATGCTGAGAACGGGCAACAACTTTGAGTTTACCTACAACTT<br>TGAGGAGGTGCCCTTCCACTCCAGCTTCGCTCCCAGTCAGAACCTGTTCAAGCTGG<br>CCAACCCGCTGGTGGACCAGTACTTGTACCGCTTCGTGAGCACAAATAACACTGGC<br>GGAGTCCAGTTCAACAAGAACCTGGCCGGGAGATACGCCAACACCTACAAAAACTG<br>GTTCCCGGGGCCCATGGGCCGAACCCAGGGCTGGAACCTGGGCTCCGGGGTCAA<br>CCGCGCCAGTGTCAGCGCCTTCGCCACGACCAATAGGATGGAGCTCGAGGGCGC<br>GAGTTACCAGGTGCCCCCGCAGCCGAACGGCATGACCAACAACCTCCAGGGCAGC<br>AACACCTATGCCCTGGAGAACACTATGATCTTCAACAGCCAGCCGGCGAACCCGGG<br>CACCACCGCCACGTACCTCGAGGGCAACATGCTCATCACCAGCGAGAGCGAGACG<br>CAGCCGGTGAACCGCGTGGCGTACAACGTCGGCGGGCAGATGGCCACCAACAGA<br>CAGAGCTCCACCACTGCCCCCGCGACCGGCACGTACAACCTCCAGGAAATCGTGC<br>CCGGCAGCGTGTGGATGGAGAGGGACGTGTACCTCCAAGGACCCATCTGGGCCAA<br>GATCCCAGAGACGGGGGCGCACTTTCACCCCTCTCCGGCCATGGGCGGATTCGGA<br>CTCAAACACCCACCGCCCATGATGCTCATCAAGAACACGCCTGTGCCCGGAAATAT<br>CACCAGCTTCTCGGACGTGCCCGTCAGCAGCTTCATCACCCAGTACAGCACCGGG<br>CAGGTCACCGTGGAGATGGAGTGGGAGCTCAAGAAGGAAAACTCCAAGAGGTGGA<br>ACCCAGAGATCCAGTACACAAACAACTACAACGACCCCCAGTTTGTGGACTTTGCC<br>CCGGACAGCACCGGGGAATACAGAACCACCAGACCTATCGGAACCCGATACCTTA<br>CCCGACCCCTT (SEQ ID NO: 10) |

In Table 1, AA refers to the amino acid sequence and NA refers to the nucleic acid sequence of the AAV capsid protein as indicated.

In certain embodiments, the modified capsid protein provided herein is a modified capsid protein of an AAV serotype selected from the group consisting of AAV1, AAV2, AAV4, AAV5, AAV6, AAV7, AAV8, AAV9, AAVB1, AAVAnc80, AAV7m8, AAVrh10, AAV2 (Y444F), AAV2 (Y444+500+730), AAV2 (Y252+272+444+500+700+704+730F), AAV8 (Y733F), and any variant thereof. The capsid protein of any AAV serotype may be modified according to the substitutions described herein. The skilled artisan will readily be able to identify any other AAV serotype suitable for introducing the amino acid substitutions described herein (e.g., substitutions at S194, G474, N564, and/or N573, wherein numbering of the positions is based on VP1 numbering of AAV5). In certain embodiments, the modified capsid protein is a modified capsid protein of AAV5. In certain embodiments, the modified capsid protein is a modified capsid protein of AAV1. In certain embodiments, the modified capsid protein is a modified capsid protein of AAV2. In certain embodiments, the modified capsid protein is a modified capsid protein of AAV4. In certain embodiments, the modified capsid protein is a modified capsid protein of AAV6. In certain embodiments, the modified capsid protein is a modified capsid protein of AAV7. In certain embodiments, the modified capsid protein is a modified capsid protein of AAV8. In certain embodiments, the modified capsid protein is a modified capsid protein of AAV9. In certain embodiments, the modified capsid protein is a modified capsid protein of AAVB1. See, Choudhury et al. (2016) Mol. Ther., 24(7): 1247-1257, the disclosure of which is incorporated herein by reference in its entirety. In certain embodiments, the modified capsid protein is a modified capsid protein of AAVAnc80, including Anc80L65, Anc80L27, and Anc80L121. See, Carvalho et al. (2018) Human Gene Therapy, 29 (7): 771-784, the disclosure of which is incorporated herein by reference in its entirety. In certain embodiments, the modified capsid protein is a modified capsid protein of AAV7m8. See, Dalkara et al. (2013) Sci. Transl. Med., 5 (189): 189ra76, the disclosure of which is incorporated herein by reference in its entirety. In certain embodiments, the modified capsid protein is a modified capsid protein of AAVrh10. See, Gao et al. (2002) Proc. Natl. Acad. Sci. USA, 99 (18): 11854-11859, the disclosure of which is incorporated herein by reference in its entirety. In certain embodiments, the modified capsid protein is a modified capsid protein of AAV2 (Y444F), e.g., a modified capsid protein of AAV2 comprising a phenylalanine (F) at position 444. In certain embodiments, the modified capsid protein is a modified capsid protein of AAV2 (Y444+500+730), e.g., a modified capsid protein of AAV2 comprising a phenylalanine (F) at positions 444, 500, and 730. In certain embodiments, the modified capsid protein is a modified capsid protein of AAV2 (Y252+272+444+500+700+704+730F), e.g., a modified capsid protein of AAV2 comprising a phenylalanine (F) at positions 252, 272, 444, 500, 700, 704 and 730. In certain embodiments, the modified capsid protein is a modified capsid protein of AAV8 (Y733F). See, Bogner et al. (2015) PLOS One, 10(6): e0128759 (1-16), and U.S. Pat. No. 8,445,267, the disclosures of which are incorporated herein by reference in their entirety. In certain embodiments, the modified capsid protein is a modified capsid protein of a variant of any of the AAV serotypes described herein.

Nucleic Acids, Vectors, and Methods of Production

Provided herein are nucleic acids (e.g., isolated nucleic acids) encoding a polypeptide (e.g., an AAV capsid protein) as described herein.

Accordingly, in one aspect, provided herein is a nucleic acid comprising a nucleotide sequence that encodes a polypeptide (e.g., an AAV capsid protein) comprising an amino acid substitution at one or more positions corresponding to amino acids S194, G474, N564, and/or N573, wherein numbering of the positions is based on VP1 numbering of AAV5. In certain embodiments, numbering of the positions is based on the amino acid sequence of the wild-type AAV5 VP1 as set forth in SEQ ID NO:1. As such, in certain embodiments, provided herein is a nucleic acid comprising a nucleotide sequence that encodes a polypeptide (e.g., an AAV capsid protein) comprising an amino acid substitution at one or more positions corresponding to amino acids S194, G474, N564, and/or N573, wherein numbering of the positions is based on the amino acid sequence of the wild-type AAV5 VP1 as set forth in SEQ ID NO: 1.

In certain embodiments, the nucleic acid comprises a nucleotide sequence that encodes for a modified capsid protein comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity with the amino acid sequence set forth in SEQ ID NO:1. In certain embodiments, the nucleic acid comprises a nucleotide sequence that encodes for a modified capsid protein comprising an amino acid sequence having at least 95% sequence identity with the amino acid sequence set forth in SEQ ID NO:1. In certain embodiments, the nucleic acid comprises a nucleotide sequence that encodes for a modified capsid protein comprising an amino acid sequence having at least 99% sequence identity with the amino acid sequence set forth in SEQ ID NO: 1. In certain embodiments, the modified capsid protein comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity with the amino acid sequence set forth in SEQ ID NO:1, is encoded by a nucleic acid comprising a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity with the nucleotide sequence set forth in SEQ ID NO:2.

In certain embodiments, provided herein is a nucleic acid comprising a nucleotide sequence that encodes for a modified capsid protein comprising an amino acid substitution at the position corresponding to amino acid S194, wherein numbering of the position is based on the amino acid sequence of the wild-type AAV5 VP1 as set forth in SEQ ID NO: 1. In certain embodiments, the amino acid in the modified capsid protein corresponding to amino acid 194 is G. In certain embodiments, the nucleic acid comprises a nucleotide sequence that encodes for a modified capsid protein comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity with the amino acid sequence set forth in SEQ ID NO:3, wherein the amino acid in the capsid protein corresponding to amino acid 194 of SEQ ID NO:3 is G. In certain embodiments, the nucleic acid comprises a nucleotide sequence that encodes for a modified capsid protein comprising the amino acid sequence set forth in SEQ ID NO:3. In certain embodiments, the nucleic acid comprises a nucleotide sequence that encodes for a modified capsid protein, wherein the amino acid sequence of the modified capsid protein consists of the amino acid sequence set forth in SEQ ID NO:3. In certain embodiments, the modified capsid protein comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity with the amino acid sequence set forth in SEQ ID NO:3, wherein the amino acid in the capsid protein corresponding to amino acid 194 of SEQ ID NO:3 is G, is encoded by a nucleic acid comprising a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity with the nucleotide sequence set forth in SEQ ID NO: 4. In certain embodiments, provided herein is an isolated nucleic acid comprising the nucleotide sequence set forth in SEQ ID NO:4. In certain embodiments, provided herein is an isolated nucleic acid consisting of the nucleotide sequence set forth in SEQ ID NO:4.

In certain embodiments, provided herein is a nucleic acid comprising a nucleotide sequence that encodes for a modified capsid protein comprising an amino acid substitution at the position corresponding to amino acid G474, wherein numbering of the position is based on the amino acid sequence of the wild-type AAV5 VP1 as set forth in SEQ ID NO: 1. In certain embodiments, the amino acid in the modified capsid protein corresponding to amino acid 474 is R. In certain embodiments, the nucleic acid comprises a nucleotide sequence that encodes for a modified capsid protein comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity with the amino acid sequence set forth in SEQ ID NO:5, wherein the amino acid in the capsid protein corresponding to amino acid 474 of SEQ ID NO:5 is R. In certain embodiments, the nucleic acid comprises a nucleotide sequence that encodes for a modified capsid protein comprising the amino acid sequence set forth in SEQ ID NO:5. In certain embodiments, the nucleic acid comprises a nucleotide sequence that encodes for a modified capsid protein, wherein the amino acid sequence of the modified capsid protein consists of the amino acid sequence set forth in SEQ ID NO:5. In certain embodiments, the modified capsid protein comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity with the amino acid sequence set forth in SEQ ID NO:5, wherein the amino acid in the capsid protein corresponding to amino acid 474 of SEQ ID NO:5 is R, is encoded by a nucleic acid comprising a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity with the nucleotide sequence set forth in SEQ ID NO: 6. In certain embodiments, provided herein is an isolated nucleic acid comprising the nucleotide sequence set forth in SEQ ID NO:6. In certain embodiments, provided herein is an isolated nucleic acid consisting of the nucleotide sequence set forth in SEQ ID NO:6.

In certain embodiments, provided herein is a nucleic acid comprising a nucleotide sequence that encodes for a modified capsid protein comprising an amino acid substitution at the position corresponding to amino acid N564, wherein numbering of the position is based on the amino acid sequence of the wild-type AAV5 VP1 as set forth in SEQ ID NO: 1. In certain embodiments, the amino acid in the modified capsid protein corresponding to amino acid 564 is R. In certain embodiments, the nucleic acid comprises a nucleotide sequence that encodes for a modified capsid protein comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity with the amino acid sequence set forth in SEQ ID NO:7, wherein the amino acid in the capsid protein corresponding to amino acid 564 of SEQ ID NO:7 is R. In certain embodiments, the nucleic acid comprises a nucleotide sequence that encodes for a modified capsid protein comprising the amino acid sequence set forth in SEQ ID NO:7. In certain embodiments, the nucleic acid comprises a nucleotide sequence that encodes for a modified capsid protein, wherein the amino acid sequence of the modified capsid protein consists of the amino acid sequence set forth in SEQ ID NO:7. In certain embodiments, the modified capsid protein comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity with the amino acid sequence set forth in SEQ ID NO:7, wherein the amino acid in the capsid protein corresponding to amino acid 564 of SEQ ID NO:7 is R, is encoded by a nucleic acid comprising a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity with the nucleotide sequence set forth in SEQ ID NO: 8. In certain embodiments, provided herein is an isolated nucleic acid comprising the nucleotide sequence set forth in SEQ ID NO:8. In certain embodiments, provided herein is an isolated nucleic acid consisting of the nucleotide sequence set forth in SEQ ID NO:8.

In certain embodiments, provided herein is a nucleic acid comprising a nucleotide sequence that encodes for a modified capsid protein comprising an amino acid substitution at the position corresponding to amino acid N573, wherein numbering of the position is based on the amino acid sequence of the wild-type AAV5 VP1 as set forth in SEQ ID NO: 1. In certain embodiments, the amino acid in the modified capsid protein corresponding to amino acid 573 is R. In certain embodiments, the nucleic acid comprises a nucleotide sequence that encodes for a modified capsid protein comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity with the amino acid sequence set forth in SEQ ID NO:9, wherein the amino acid in the capsid protein corresponding to amino acid 573 of SEQ ID NO:9 is R. In certain embodiments, the nucleic acid comprises a nucleotide sequence that encodes for a modified capsid protein comprising the amino acid sequence set forth in SEQ ID NO:9. In certain embodiments, the nucleic acid comprises a nucleotide sequence that encodes for a modified capsid protein, wherein the amino acid sequence of the modified capsid protein consists of the amino acid sequence set forth in SEQ ID NO:9. In certain embodiments, the modified capsid protein comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity with the amino acid sequence set forth in SEQ ID NO:9, wherein the amino acid in the capsid protein corresponding to amino acid 573 of SEQ ID NO:9 is R, is encoded by a nucleic acid comprising a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity with the nucleotide sequence set forth in SEQ ID NO: 10. In certain embodiments, provided herein is an isolated nucleic acid comprising the nucleotide sequence set forth in SEQ ID NO:10. In certain embodiments, provided herein is an isolated nucleic acid consisting of the nucleotide sequence set forth in SEQ ID NO:10.

In certain embodiments, the nucleic acid may be optimized, e.g., using codon optimization, replacement and/or removal of certain elements, to improve, e.g. expression of the capsid protein. Various methods to optimize nucleic acid sequences are known in the art by those of ordinary skill in the art. For example, certain nucleotides in the nucleic acid can be mutated without altering the amino acid sequence encoded by the nucleic acid sequence, utilizing the degeneracy of the genetic code. For example, a nucleic acid can be optimized by using an alternative codon for an identical amino acid. In certain embodiments, optimization methods can increase expression of the encoded capsid protein relative to the expression of the capsid encoded by nucleic acid sequences that have not been optimized.

Numerous methods are known in the art for production of rAAV vectors, including transfection, stable cell line production, and infectious hybrid virus production systems which include adenovirus-AAV hybrids, herpesvirus-AAV hybrids (Conway, J E et al., (1997). Virology 71 (11): 8780-8789) and baculovirus-AAV hybrids. rAAV production cultures for the production of rAAV virus particles all require; 1) suitable host cells, including, for example, human-derived cell lines such as HeLa, A549, or 293 cells, or insect-derived cell lines such as SF-9, in the case of baculovirus production systems; 2) suitable helper virus function, provided by wild-type or mutant adenovirus (such as temperature sensitive adenovirus), herpes virus, baculovirus, or a plasmid construct providing helper functions (e.g., a helper viral vector selected from the group consisting of a retrovirus vector, a herpes virus vector, a baculovirus vector, or an adenovirus vector expression vector, wherein the vector is an expression vector); 3) AAV rep and cap genes and gene products; 4) a transgene (such as a therapeutic transgene) flanked by at least one AAV ITR sequences; and 5) suitable media and media components to support rAAV production. Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), custom formulations such as those described in U.S. Pat. No. 6,566,118, and Sf-900 II SFM media as described in U.S. Pat. No. 6,723,551, each of which is incorporated herein by reference in its entirety, particularly with respect to custom media formulations for use in production of recombinant AAV vectors.

The rAAV particles can be produced using methods known in the art. See, e.g., U.S. Pat. Nos. 6,566,118; 6,989,264; and 6,995,006. In practicing the invention, host cells for producing rAAV particles include mammalian cells, insect cells, plant cells, microorganisms and yeast. Host cells can also be packaging cells in which the AAV rep and cap genes are stably maintained in the host cell or producer cells in which the AAV vector genome is stably maintained. Exemplary packaging and producer cells are derived from 293, A549 or HeLa cells. AAV vectors are purified and formulated using standard techniques known in the art.

In some embodiments, rAAV particles may be produced by a triple transfection method, such as the exemplary triple transfection method provided infra. Briefly, a plasmid containing a rep gene and a capsid gene, along with a helper adenoviral plasmid, may be transfected (e.g., using the calcium phosphate method) into a cell line (e.g., HEK-293 cells), and virus may be collected and optionally purified.

In some embodiments, rAAV particles may be produced by a producer cell line method, such as the exemplary producer cell line method provided infra (see also (referenced in Martin et al., (2013) Human Gene Therapy Methods 24:253-269). Briefly, a cell line (e.g., a HeLa cell line) may be stably transfected with a plasmid containing a rep gene, a capsid gene, and a promoter-transgene sequence. Cell lines may be screened to select a lead clone for rAAV production, which may then be expanded to a production bioreactor and infected with an adenovirus (e.g., a wild-type adenovirus) as helper to initiate rAAV production. Virus may subsequently be harvested, adenovirus may be inactivated (e.g., by heat) and/or removed, and the rAAV particles may be purified.

Suitable rAAV production culture media of the present invention may be supplemented with serum or serum-derived recombinant proteins at a level of 0.5-20 (v/v or w/v). Alternatively, as is known in the art, rAAV vectors may be produced in serum-free conditions which may also be referred to as media with no animal-derived products. One of ordinary skill in the art may appreciate that commercial or custom media designed to support production of rAAV vectors may also be supplemented with one or more cell culture components know in the art, including without limitation glucose, vitamins, amino acids, and or growth factors, in order to increase the titer of rAAV in production cultures.

rAAV production cultures can be grown under a variety of conditions (over a wide temperature range, for varying lengths of time, and the like) suitable to the particular host cell being utilized. As is known in the art, rAAV production cultures include attachment-dependent cultures which can be cultured in suitable attachment-dependent vessels such as, for example, roller bottles, hollow fiber filters, microcarriers, and packed-bed or fluidized-bed bioreactors. rAAV vector production cultures may also include suspension-adapted host cells such as HeLa, 293, and SF-9 cells which can be cultured in a variety of ways including, for example, spinner flasks, stirred tank bioreactors, and disposable systems such as the Wave bag system.

rAAV vector particles as described herein may be harvested from rAAV production cultures by lysis of the host cells of the production culture or by harvest of the spent media from the production culture, provided the cells are cultured under conditions known in the art to cause release of rAAV particles into the media from intact cells, as described more fully in U.S. Pat. No. 6,566,118). In certain embodiments, rAAV vector particles as described herein are produced by a method comprising culturing the recombinant host cell under conditions whereby the nucleic acid is expressed and the capsid protein is produced. Suitable methods of lysing cells are also known in the art and include for example multiple freeze/thaw cycles, sonication, microfluidization, and treatment with chemicals, such as detergents and/or proteases.

In a further embodiment, the rAAV particles are purified. The term "purified" as used herein includes a preparation of rAAV particles devoid of at least some of the other components that may also be present where the rAAV particles naturally occur or are initially prepared from. Thus, for example, isolated rAAV particles may be prepared using a purification technique to enrich it from a source mixture, such as a culture lysate or production culture supernatant. Enrichment can be measured in a variety of ways, such as, for example, by the proportion of DNase-resistant particles (DRPs) or genome copies (gc) present in a solution, or by infectivity, or it can be measured in relation to a second, potentially interfering substance present in the source mixture, such as contaminants, including production culture contaminants or in-process contaminants, including helper virus, media components, and the like.

In some embodiments, the rAAV production culture harvest is clarified to remove host cell debris. In some embodiments, the production culture harvest is clarified by filtration through a series of depth filters including, for example, a grade DOHC Millipore® Millistak+® HC Pod Filter, a grade A1HC Millipore® Millistak+® HC Pod Filter, and a 0.2μιη Filter Opticap® XL 10 Millipore Express® SHC Hydrophilic Membrane filter. Clarification can also be achieved by a variety of other standard techniques known in the art, such as, centrifugation or filtration through any cellulose acetate filter of 0.2μιη or greater pore size known in the art.

In some embodiments, the rAAV production culture harvest is further treated with Benzonase® to digest any high molecular weight DNA present in the production culture. In some embodiments, the Benzonase® digestion is performed under standard conditions known in the art including, for example, a final concentration of 1-2.5 units/ml of Benzonase® at a temperature ranging from ambient to 37° C. for a period of 30 minutes to several hours.

rAAV particles may be isolated or purified using one or more of the following purification steps: equilibrium centrifugation; flow-through anionic exchange filtration; tangential flow filtration (TFF) for concentrating the rAAV particles; rAAV capture by apatite chromatography; heat inactivation of helper virus; rAAV capture by hydrophobic interaction chromatography; buffer exchange by size exclusion chromatography (SEC); nanofiltration; and rAAV capture by anionic exchange chromatography, cationic exchange chromatography, or affinity chromatography.

These steps may be used alone, in various combinations, or in different orders. In some embodiments, the method comprises all the steps in the order as described below. Methods to purify rAAV particles are found, for example, in Xiao et al., (1998) Journal of Virology 72:2224-2232; U.S. Pat. Nos. 6,989,264 and 8,137,948; and WO 2010/148143.

In some embodiments, the pharmaceutical compositions comprising a rAAV described herein and a pharmaceutically acceptable carrier is suitable for administration to human. Such carriers are well known in the art (see, e.g., Remington's Pharmaceutical Sciences, 15th Edition, pp. 1035-1038 and 1570-1580). In some embodiments, the pharmaceutical compositions comprising a rAAV described herein and a pharmaceutically acceptable carrier is suitable for ocular injection. Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. The pharmaceutical composition may further comprise additional ingredients, for example preservatives, buffers, tonicity agents, antioxidants and stabilizers, nonionic wetting or clarifying agents, viscosity-increasing agents, and the like. The pharmaceutical compositions described herein can be packaged in single unit dosages or in multidosage forms. The compositions are generally formulated as sterile and substantially isotonic solution.

AAV Compositions and Methods of Use

In one aspect, provided herein is an rAAV particle comprising an rAAV capsid comprising a polypeptide (e.g., a modified capsid protein) described herein, and an rAAV vector comprising a heterologous nucleic acid.

The rAAV may comprise a heterologous nucleic acid encoding a polypeptide (e.g., a therapeutic or diagnostic polypeptide) and/or a therapeutic nucleic acid. A heterologous nucleic acid which encodes therapeutic or diagnostic polypeptides and/or therapeutic nucleic acid can be generated using methods known in the art, using standard synthesis and recombinant methods. In some embodiments, the heterologous nucleic acid encodes a therapeutic polypeptide. In some embodiments, the heterologous nucleic acid encodes a diagnostic polypeptide. Non-limiting examples of nucleic acid encoding therapeutic polypeptides include: nucleic acids for replacement of a missing or mutated gene known to cause retinal disease, for example Prph2, RPE65, MERTK, RPGR, RP2, RPGRIP, CNGA3, CNGB3, and GNAT2. Other non-limiting examples of nucleic acids encoding therapeutic polypeptides include those encoding neurotrophic factors (such as GDNF, CNTF, FGF2, PEDF, EPO), anti-apoptotic genes (such as BCL2, BCL-X, NFKB), anti-angiogenic factors (such as Endostatin, Angiostatin, sFlt), and anti-inflammatory factors (such as IL10, ILI-ra, TGFfi, IL4). Other therapeutic polypeptides for ocular disorders include but are not limited to Myo7a, ABCA4, REP1, GUCY2D, PDE6C, RSI, RPGRIP, Lpcatl, AIPL1, RDH12, CHM. In some embodiments, the encoded polypeptide is the human variant of the polypeptide.

The heterologous nucleic acids may encode polypeptides that are intracellular proteins, anchored in the cell membrane, remain within the cell, or are secreted by the cell transduced with the vectors as described herein. For polypeptides secreted by the cell that receives the vector; the polypeptide can be soluble (i.e., not attached to the cell). For example, soluble polypeptides are devoid of a transmembrane region and are secreted from the cell. Techniques to identify and remove nucleic acid sequences which encode transmembrane domains are known in the art.

Also provided herein are vectors comprising a heterologous nucleic acid which encodes a RNA (e.g., RNAi, ribozymes, miRNA, siRNA, antisense RNA) that when transcribed from the nucleic acids of the vector can treat an ocular disorder by interfering with translation or transcription of an abnormal or excess protein associated with a disease state of the invention. For example, the heterologous nucleic acid described herein may encode for an RNA which treats a disease by highly specific elimination or reduction of mRNA encoding the abnormal and/or excess proteins. Therapeutic RNA sequences include RNAi, small inhibitory RNA (siRNA), micro RNA (miRNA), and/or ribozymes (such as hammerhead and hairpin ribozymes) that can treat diseases by highly specific elimination or reduction of mRNA encoding the abnormal and/or excess proteins, such as those occurring in various forms of inherited retinal degeneration. Non-limiting examples of ocular disorders which may be treated by therapeutic RNA sequences include, for example, autosomal dominant retinitis pigmentosa (ADRP) and diabetic retinopathy. Examples of therapeutic RNA sequences and nucleic acids encoding these sequences which may be used in the invention include those described in, for example, U.S. Pat. No. 6,225,291, the disclosure of which is herein incorporated by reference in its entirety. In some embodiments, the therapeutic RNA sequence is miR-708. In some embodiments, the miR-708 is used in combination with a nucleic acid encoding a wild-type rhodopsin, either as part of the same rAAV vector or as part of a second rAAV vector. In some embodiments, the nucleic acid encoding the wild-type rhodopsin lacks the miR-708 target sequence located in 3' untranslated region of the rhodopsin gene. rAAV vectors encoding miR-708 and/or rhodopsin are provided by U.S. Provisional Patent Application Ser. No. 61/969,027, incorporated herein by reference in its entirety.

The heterologous nucleic acid may encode polypeptides that are intracellular proteins, anchored in the cell membrane, remain within the cell, or are secreted by the cell transduced with the vectors as described herein. For polypeptides secreted by the cell that receives the vector; the polypeptide can be soluble (i.e., not attached to the cell). For example, soluble polypeptides are devoid of a transmembrane region and are secreted from the cell. Techniques to identify and remove nucleic acid sequences which encode transmembrane domains are known in the art.

In some embodiments, the heterologous nucleic acid is operably linked to a promoter. Exemplary promoters include, but are not limited to, the cytomegalovirus (CMV) immediate early promoter, the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken beta-actin/Rabbit β-globin promoter (CAG promoter; Niwa et al, Gene, 1991, 108(2): 193-9) and the elongation factor 1-alpha promoter (EFI-alpha) promoter (Kim et al, Gene, 1990, 91(2):217-23 and Guo et al, Gene Ther., 1996, 3(9):802-10). In some embodiments, the promoter comprises a human β-glucuronidase promoter or a cytomegalovirus enhancer linked to a chicken β-actin (CBA) promoter. The promoter can be a constitutive, inducible or repressible promoter. In some embodiments, provided herein is a recombinant vector comprising nucleic acid encoding a heterologous transgene of the present disclosure operably linked to a CBA promoter. Exemplary promoters and descriptions may be found, e.g., in U.S. PG Pub. 20140335054.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the 13-actin promoter, the phosphoglycerol kinase (PGK) promoter, and the EFIa promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In certain embodiments, the heterologous nucleic acid is operably linked to a promoter suitable for expression in an ocular tissue. In certain embodiments, the heterologous nucleic acid is operably linked to a promoter suitable for expression in a retina. In certain embodiments, the heterologous nucleic acid is operably linked to a promoter suitable for expression in a retinal cell selected from the group consisting of a photoreceptor cell, a retinal pigmented epithelial cell, a bipolar cell, a horizontal cell, an amacrine cell, a muller cell, a ganglion cell, and any combination thereof. In certain embodiments, the heterologous nucleic acid is operably linked to a promoter suitable for expression in a cornea. In certain embodiments, the heterologous nucleic acid is operably linked to a promoter suitable for expression in a corneal cell selected from the group consisting of an epithelial cell, a keratocyte, an endothelial cell, and any combination thereof. Other retinal and corneal cell types are known in the art and a skilled artisan would be able to determine the promoter suitable for expression in those cell types.

Provided herein are methods of using the rAAV compositions described herein. In certain embodiments, provided is a method for delivering a heterologous nucleic acid to an ocular tissue of a subject, comprising administering an rAAV particle to the subject. In certain embodiments, the rAAV particle comprises: an rAAV capsid comprising a modified capsid protein, wherein the modified capsid protein comprises an amino acid substitution at one or more positions corresponding to amino acids 194, 474, 564, and/or 573, wherein numbering of the positions is based on VP1 numbering of AAV5; and an rAAV vector comprising a heterologous nucleic acid. In certain embodiments, the method is for delivering a heterologous nucleic acid to the retina of a subject. In such embodiments, the rAAV particle comprises: an rAAV capsid comprising a modified capsid protein, wherein the modified capsid protein comprises an amino acid substitution at a position corresponding to amino acid 194, wherein numbering of the positions is based on VP1 numbering of AAV5; and an rAAV vector comprising a heterologous nucleic acid. In certain embodiments, the method is for delivering a heterologous nucleic acid to the cornea of a subject. In such embodiments, the rAAV particle comprises: an rAAV capsid comprising a modified capsid protein, wherein the modified capsid protein comprises an amino acid substitution at one or more positions corresponding to amino acids 474, 564, and/or 573, wherein numbering of the positions is based on VP1 numbering of AAV5; and an rAAV vector comprising a heterologous nucleic acid.

In certain embodiments, provided is a method for improving rAAV transduction of cells in an ocular tissue of a subject, comprising administering an rAAV particle to the subject. In certain embodiments, the rAAV particle comprises: an rAAV capsid comprising a modified capsid protein, wherein the modified capsid protein comprises an amino acid substitution at one or more positions corresponding to amino acids 194, 474, 564, and/or 573, wherein numbering of the positions is based on VP1 numbering of AAV5; and an rAAV vector comprising a heterologous nucleic acid. In certain embodiments, the method is for improving rAAV transduction of cells in the retina of a subject. In such embodiments, the rAAV particle comprises: an rAAV capsid comprising a modified capsid protein, wherein the modified capsid protein comprises an amino acid substitution at a position corresponding to amino acid 194, wherein numbering of the positions is based on VP1 numbering of AAV5; and an rAAV vector comprising a heterologous nucleic acid. In certain embodiments, the method is for improving rAAV transduction of cells in the cornea of a subject. In such embodiments, the rAAV particle comprises: an rAAV capsid comprising a modified capsid protein, wherein the modified capsid protein comprises an amino acid substitution at one or more positions corresponding to amino acids 474, 564, and/or 573, wherein numbering of the positions is based on VP1 numbering of AAV5; and an rAAV vector comprising a heterologous nucleic acid.

In certain embodiments, provided is a method for improving expression of a heterologous nucleic acid in an ocular tissue of a subject, comprising administering an rAAV particle to the subject. In certain embodiments, the rAAV particle comprises: an rAAV capsid comprising a modified capsid protein, wherein the modified capsid protein comprises an amino acid substitution at one or more positions corresponding to amino acids 194, 474, 564, and/or 573, wherein numbering of the positions is based on VP1 numbering of AAV5; and an rAAV vector comprising a heterologous nucleic acid. In certain embodiments, the method is for improving expression of a heterologous nucleic acid in the retina of a subject. In such embodiments, the rAAV particle comprises: an rAAV capsid comprising a modified capsid protein, wherein the modified capsid protein comprises an amino acid substitution at a position corresponding to amino acid 194, wherein numbering of the positions is based on VP1 numbering of AAV5; and an rAAV vector comprising a heterologous nucleic acid. In certain embodiments, the method is for improving expression of a heterologous nucleic acid in the cornea of a subject. In such embodiments, the rAAV particle comprises: an rAAV capsid comprising a modified capsid protein, wherein the modified capsid protein comprises an amino acid substitution at one or more positions corresponding to amino acids 474, 564, and/or 573, wherein numbering of the positions is based on VP1 numbering of AAV5; and an rAAV vector comprising a heterologous nucleic acid.

Also provided herein is a method to treat a condition or a disorder of the eye in a subject comprising administering an effective amount of a composition comprising an rAAV particle to the subject, wherein the rAAV particle comprises an rAAV capsid comprising a modified capsid protein, wherein the modified capsid protein comprises an amino acid substitution at one or more positions corresponding to amino acids 194, 474, 564, and/or 573, wherein numbering of the positions is based on VP1 numbering of AAV5; and an rAAV vector comprising a heterologous nucleic acid.

In the various methods described herein, the heterologous nucleic acid is expressed at an increased level of expression, as compared to the level of expression of a heterologous nucleic acid of an rAAV particle comprising a wild-type rAAV capsid.

Methods of Administration

Methods of subretinal delivery are known in the art. For example, see WO 2009/105690, incorporated herein by reference. Briefly, the general method for delivering rAAV particles (e.g., modified rAAV particles as described herein) to the subretina of the macula and fovea may be illustrated by the following brief outline. This example is merely meant to illustrate certain features of the method, and is in no way meant to be limiting.

Generally, the rAAV vector can be delivered in the form of a composition injected intraocularly (subretinally) under direct observation using an operating microscope. In some embodiments the vector is encapsidated in a rAAV particle wherein the rAAV particle comprises a rAAV capsid as described herein, and the rAAV vector comprising a heterologous nucleic acid and at least one AAV inverted terminal repeat. This procedure may involve vitrectomy followed by injection of rAAV vector suspension using a fine cannula through one or more small retinotomies into the subretinal space.

Briefly, an infusion cannula can be sutured in place to maintain a normal globe volume by infusion (of e.g., saline) throughout the operation. A vitrectomy is performed using a cannula of appropriate bore size (for example 20 to 27 gauge), wherein the volume of vitreous gel that is removed is replaced by infusion of saline or other isotonic solution from the infusion cannula. The vitrectomy is advantageously performed because (1) the removal of its cortex (the posterior hyaloid membrane) facilitates penetration of the retina by the cannula; (2) its removal and replacement with fluid (e.g., saline) creates space to accommodate the intraocular injection of vector, and (3) its controlled removal reduces the possibility of retinal tears and unplanned retinal detachment.

In some embodiments, the rAAV composition is directly injected into the subretinal space outside the central retina, by utilizing a cannula of the appropriate bore size (e.g., 27-45 gauge), thus creating a bleb in the subretinal space. In other embodiments, the subretinal injection of rAAV composition is preceded by subretinal injection of a small volume (e.g., about 0.1 to about 0.5 ml) of an appropriate fluid (such as saline or Ringer's solution) into the subretinal space outside the central retina. This initial injection into the subretinal space establishes an initial fluid bleb within the subretinal space, causing localized retinal detachment at the location of the initial bleb. This initial fluid bleb can facilitate targeted delivery of rAAV composition to the subretinal space (by defining the plane of injection prior to rAAV delivery), and minimize possible rAAV administration into the choroid and the possibility of rAAV injection or reflux into the vitreous cavity. In some embodiments, this initial fluid bleb can be further injected with fluids comprising one or more rAAV compositions and/or one or more additional therapeutic agents by administration of these fluids directly to the initial fluid bleb with either the same or additional fine bore cannulas.

Intraocular administration of the rAAV compositions and/or the initial small volume of fluid can be performed using a fine bore cannula (e.g., 27-45 gauge) attached to a syringe. In some embodiments, the plunger of this syringe may be driven by a mechanized device, such as by depression of a foot pedal. The fine bore cannula is advanced through the sclerotomy, across the vitreous cavity and into the retina at a site pre-determined in each subject according to the area of retina to be targeted (but outside the central retina). Under direct visualization the vector suspension is injected mechanically under the neurosensory retina causing a localized retinal detachment with a self-sealing non-expanding retinotomy. As noted above, the rAAV composition can be either directly injected into the subretinal space creating a bleb outside the central retina or the vector can be injected into an initial bleb outside the central retina, causing it to expand (and expanding the area of retinal detachment). In some embodiments, the injection of rAAV composition is followed by injection of another fluid into the bleb.

Without wishing to be bound by theory, the rate and location of the subretinal injection(s) can result in localized shear forces that can damage the macula, fovea and/or underlying RPE cells. The subretinal injections may be performed at a rate that minimizes or avoids shear forces. One of ordinary skill in the art would recognize that the rate and time of injection of the bleb may be directed by, for example, the volume of the rAAV composition or size of the bleb necessary to create sufficient retinal detachment to access the cells of central retina, the size of the cannula used to deliver the rAAV composition, and the ability to safely maintain the position of the cannula.

In some embodiments, the methods comprise administration to the eye (e.g., by subretinal and/or intravitreal administration) an effective amount of recombinant viral particles comprising a vector encoding a heterologous nucleic acid. In certain embodiments, methods as described herein result in rAAV transduction of the retina. In certain embodiments, methods as described herein result in rAAV transduction of a retinal cell. In certain embodiments, methods as described herein result in rAAV transduction of the cornea. In certain embodiments, methods as described herein result in rAAV transduction of a corneal cell.

In order to safely and efficiently transduce areas of target retina (e.g., the central retina) outside the edge of the original location of the bleb, the bleb may be manipulated to reposition the bleb to the target area for transduction. Manipulation of the bleb can occur by the dependency of the bleb that is created by the volume of the bleb, repositioning of the eye containing the bleb, repositioning of the head of the human with an eye or eyes containing one or more blebs, and/or by means of a fluid-air exchange. This is particularly relevant to the central retina since this area typically resists detachment by subretinal injection. In some embodiments fluid-air exchange is utilized to reposition the bleb; fluid from the infusion cannula is temporarily replaced by air, e.g., from blowing air onto the surface of the retina. As the volume of the air displaces vitreous cavity fluid from the surface of the retina, the fluid in the vitreous cavity may flow out of a cannula. The temporary lack of pressure from the vitreous cavity fluid causes the bleb to move and gravitate to a dependent part of the eye. By positioning the eye globe appropriately, the bleb of subretinal rAAV composition is manipulated to involve adjacent areas (e.g., the macula and/or fovea). In some cases, the mass of the bleb is sufficient to cause it to gravitate, even without use of the fluid-air exchange. Movement of the bleb to the desired location may further be facilitated by altering the position of the subject's head, so as to allow the bleb to gravitate to the desired location in the eye. Once the desired configuration of the bleb is achieved, fluid is returned to the vitreous cavity. The fluid is an appropriate fluid, e.g., fresh saline. Generally, the subretinal rAAV composition may be left in situ without retinopexy to the retinotomy and without intraocular tamponade, and the retina will spontaneously reattach within about 48 hours.

By safely and effectively transducing ocular cells (e.g., RPE and/or photoreceptor cells of e.g., the macula and/or fovea) with a vector comprising a therapeutic polypeptide or RNA sequence, the methods described herein may be used to treat an individual; e.g., a human, having an ocular disorder, wherein the transduced cells produce the therapeutic polypeptide or RNA sequence in an amount sufficient to treat the ocular disorder. In some embodiments, transduction of ocular cells is improved by using rAAV particles (e.g., modified rAAV particles as described herein) comprising AAV capsid proteins described herein.

An effective amount of rAAV (in some embodiments in the form of particles) is administered, depending on the objectives of treatment. For example, where a low percentage of transduction can achieve the desired therapeutic effect, then the objective of treatment is generally to meet or exceed this level of transduction. In some instances, this level of transduction can be achieved by transduction of only about 1 to 5% of the target cells, in some embodiments at least about 20% of the cells of the desired tissue type, in some embodiments at least about 50%, in some embodiments at least about 80%, in some embodiments at least about 95%, in some embodiments at least about 99% of the cells of the desired tissue type. As discussed above, substitution of one or more amino acids of the rAAV capsid as described herein improves rAAV transduction. The rAAV composition may be administered by one or more subretinal or intravitreal injections, either during the same procedure or spaced apart by days, weeks, months, or years. In some embodiments, multiple vectors may be used to treat the human.

In some embodiments, the administration to the retina of an effective amount of rAAV viral particles comprising a rAAV capsid described herein transduces photoreceptor cells at or near the site of administration. In some embodiments, more than about any of 5%, 10%, 15%, 20%, 25%, 30%, 35%, 40%, 45%, 50%, 55%, 60%, 65%, 70%, 75% or 100% of photoreceptor cells are transduced. In some embodiments, about 5% to about 100%, about 10% to about 50%, about 10% to about 30%, about 25% to about 75%, about 25% to about 50%, or about 30% to about 50% of the photoreceptor cells are transduced. Methods to identify photoreceptor cells transduced by AAV viral particles comprising a rAAV capsid as described herein are known in the art; for example, immunohistochemistry or the use of a marker such as enhanced green fluorescent protein can be used to detect transduction of viral particles comprising a rAAV capsid as described herein.

In some embodiments, the methods comprise administration to the subretina (e.g., the subretinal space) of a mammal an effective amount of AAV viral particles viral particles comprising a rAAV capsid as described herein for treating an individual with an ocular disorder; e.g., a human with an ocular disorder. In some embodiments, the composition is injected to one or more locations in the subretina to allow expression of a heterologous nucleic acid in photoreceptor cells. In some embodiments, the composition is injected into any one of one, two, three, four, five, six, seven, eight, nine, ten or more than ten locations in the subretina.

In some embodiments the rAAV viral particles comprising a rAAV capsid as described herein are administered to more than one location simultaneously or sequentially. In some embodiment, multiple injections of rAAV viral particles are no more than one hour, two hours, three hours, four hours, five hours, six hours, nine hours, twelve hours or 24 hours apart.

The general method for intravitreal injection may be illustrated by the following brief outline. This example is merely meant to illustrate certain features of the method, and is in no way meant to be limiting. Procedures for intravitreal injection are known in the art (see, e.g., Peyman, G. A., et al. (2009) Retina 29(7): 875-912 and Fagan, X. J. and Al-Qureshi, S. (2013) Clin. Experiment. Ophthalmol. 41(5): 500-7).

Briefly, a subject for intravitreal injection may be prepared for the procedure by pupillary dilation, sterilization of the eye, and administration of anesthetic. Any suitable mydriatic agent known in the art may be used for pupillary dilation. Adequate pupillary dilation may be confirmed before treatment. Sterilization may be achieved by applying a sterilizing eye treatment, e.g., an iodide-containing solution such as Povidone-Iodine (BETADINE®). A similar solution may also be used to clean the eyelid, eyelashes, and any other nearby tissues (e.g., skin). Any suitable anesthetic may be used, such as lidocaine or proparacaine, at any suitable concentration. Anesthetic may be administered by any method known in the art, including without limitation topical drops, gels or jellies, and subconjuctival application of anesthetic.

Prior to injection, a sterilized eyelid speculum may be used to clear the eyelashes from the area. The site of the injection may be marked with a syringe. The site of the injection may be chosen based on the lens of the patient. For example, the injection site may be 3-3.5 mm from the limus in pseudophakic or aphakic patients, and 3.5-4 mm from the limbus in phakic patients. The patient may look in a direction opposite the injection site.

During injection, the needle may be inserted perpendicular to the sclera and pointed to the center of the eye. The needle may be inserted such that the tip ends in the vitreous, rather than the subretinal space. Any suitable volume known in the art for injection may be used. After injection, the eye may be treated with a sterilizing agent such as an antibiotic. The eye may also be rinsed to remove excess sterilizing agent.

The retina is known to contain multiple layers. Cell layers in the retina may include the inner limiting membrane, nerve fiber, ganglion cell, inner plexiform, inner nuclear, outer plexiform, outer nuclear, external limiting membrane, photoreceptor, and retinal pigment epithelium layers. The layer most proximal to the vitreous is the inner limiting membrane. This layer may contain Mueller cells (or Muller cells), a class of glia. The nerve fiber layer may contain axons from ganglion cells that form the optic nerve. The ganglion cell layer may include ganglion cells and amacrine cells. The inner plexiform layer may contain synapses between dendrites of the ganglion and amacrine cells and axons of the bipolar cells. The inner nuclear layer may contain cell nuclei of amacrine, bipolar, and horizontal cells. The outer plexiform layer may contain synapses between horizontal cell dendrites and photoreceptor cell projections. The outer nuclear layer may contain photoreceptor cell bodies. The external or outer limiting membrane may include cell connections, such as adherens junctions and desmosomes, among Mueller cell apical processes and between these processes and photoreceptor cell inner segments. The photoreceptor layer, also known as the layer of rod and cones and Jacob's membrane, may contain photoreceptor cells include rods and cones. The retinal layer most distal to the vitreous is the retinal pigment epithelium (RPE), which may include a layer of hexagonal epithelial cells containing pigment granules.

The retina is also known to contain many different cell types. Retinal neurons may include photoreceptor cells, bipolar cells, ganglion cells, amacrine cells, and horizontal cells. Photoreceptor cells are sensitive to light. They may sense light and respond by transmitting signals to the optic nerve through the bipolar cells and the ganglion cells. Photoreceptor cells may include rod cells, which generally sense light in low-light conditions, and cone cells, which generally sense color and brighter light perception. Bipolar cells may receive inputs from photoreceptor cells and synapse onto amacrine or ganglion cells. Ganglion cells may receive information from amacrine cells or horizontal cells, and their axons form the optic nerve. Horizontal cells may integrate inputs from multiple photoreceptors and aid in adjustment to light levels. Amacrine cells are interneurons that help regulate bipolar cells and provide inputs to ganglion cells. Glial cells of the retina may include Mueller cells, astroglia, and microglia.

The cornea is known to contain multiple layers. Cell layers in the cornea may include the corneal epithelium layer, the Bowman's layer, the corneal stroma layer, the Descemet's membrane layer, and the corneal endothelium layer. The corneal epithelium is a non-keratinized stratified squamous epithelium making up a thin multicellular epithelial tissue layer comprising rapidly and easily regenerated cells. The anterior limiting membrane, or Bowman's layer, is a layer composed of collagen (e.g., type I collagen fibrils), perlecan, nidogen, laminin, and other heparin sulfate proteoglycans that serve to protect the corneal stroma. Bowman's layer is known to be an acellular region of the apical stroma. The corneal stroma layer, or substantia propria, is a layer comprising regularly arranged collagen fibrils and interconnected keratocytes distributed throughout. Descemet's membrane, also known as the posterior limiting membrane, is composed mainly of collagen (e.g., collagen type IV fibrils). The corneal endothelium is a simple squamous or low cuboidal monolayer comprising mitochondria-rich corneal endothelium cells.

The effectiveness of rAAV delivery by subretinal or intravitreal injection can be monitored by several criteria as described herein. For example, after treatment in a subject using methods as described herein, the subject may be assessed for e.g., an improvement and/or stabilization and/or delay in the progression of one or more signs or symptoms of the disease state by one or more clinical parameters including those described herein. Examples of such tests are known in the art, and include objective as well as subjective (e.g., subject reported) measures. For example, to measure the effectiveness of a treatment on a subject's visual function, one or more of the following may be evaluated: the subject's subjective quality of vision or improved central vision function (e.g., an improvement in the subject's ability to read fluently and recognize faces), the subject's visual mobility (e.g., a decrease in time needed to navigate a maze), visual acuity (e.g., an improvement in the subject's Log MAR score), microperimetry (e.g., an improvement in the subject's dB score), dark-adapted perimetry (e.g., an improvement in the subject's dB score), fine matrix mapping (e.g., an improvement in the subject's dB score), Goldmann perimetry (e.g., a reduced size of scotomatous area (i.e. areas of blindness) and improvement of the ability to resolve smaller targets), flicker sensitivities (e.g., an improvement in Hertz), autofluorescence, and electrophysiology measurements (e.g., improvement in ERG). In some embodiments, the visual function is measured by the subject's visual mobility. In some embodiments, the visual function is measured by the subject's visual acuity. In some embodiments, the visual function is measured by microperimetry. In some embodiments, the visual function is measured by dark-adapted perimetry. In some embodiments, the visual function is measured by ERG. In some embodiments, the visual function is measured by the subject's subjective quality of vision.

In the case of diseases resulting in progressive degenerative visual function, treating the subject at an early age may not only result in a slowing or halting of the progression of the disease, it may also ameliorate or prevent visual function loss due to acquired amblyopia. Amblyopia may be of two types. In studies in nonhuman primates and kittens that are kept in total darkness from birth until even a few months of age, the animals even when subsequently exposed to light are functionally irreversibly blind despite having functional signals sent by the retina. This blindness occurs because the neural connections and "education" of the cortex is developmentally arrested from birth due to stimulus arrest. It is unknown if this function could ever be restored. In the case of diseases of retinal degeneration, normal visual cortex circuitry was initially "learned" or developmentally appropriate until the point at which the degeneration created significant dysfunction. The loss of visual stimulus in terms of signaling in the dysfunctional eye creates "acquired" or "learned" dysfunction ("acquired amblyopia"), resulting in the brain's inability to interpret signals, or to "use" that eye. It is unknown in these cases of "acquired amblyopia" whether with improved signaling from the retina as a result of gene therapy of the amblyopic eye could ever result in a gain of more normal function in addition to a slowing of the progression or a stabilization of the disease state. In some embodiments, the human treated is less than 30 years of age. In some embodiments, the human treated is less than 20 years of age. In some embodiments, the human treated is less than 18 years of age. In some embodiments, the human treated is less than 15 years of age. In some embodiments, the human treated is less than 14 years of age. In some embodiments, the human treated is less than 13 years of age. In some embodiments, the human treated is less than 12 years of age. In some embodiments, the human treated is less than 10 years of age. In some embodiments, the human treated is less than 8 years of age. In some embodiments, the human treated is less than 6 years of age.

In some ocular disorders, there is a "nurse cell" phenomenon, in which improving the function of one type of cell improves the function of another. For example, transduction of the RPE of the central retina by a rAAV as described herein may then improve the function of the rods, and in turn, improved rod function results in improved cone function. Accordingly, treatment of one type of cell may result in improved function in another.

The selection of a particular rAAV vector and composition depend on a number of different factors, including, but not limited to, the individual human's medical history and features of the condition and the individual being treated. The assessment of such features and the design of an appropriate therapeutic regimen is ultimately the responsibility of the prescribing physician. In some embodiments, the human to be treated has a genetic ocular disorder, but has not yet manifested clinical signs or symptoms. In some embodiments, the human to be treated has an ocular disorder. In some embodiments, the human to be treated has manifested one or more signs or symptoms of an ocular disorder.

Non-limiting examples of ocular disorders which may be treated by the systems and methods described herein include: autosomal recessive severe early-onset retinal degeneration (Leber's Congenital Amaurosis), congenital achromatopsia, Stargardt's disease, Best's disease, Doyne's disease, cone dystrophy, cone-rod dystrophy, retinitis pigmentosa, X-linked retinoschisis, Usher's syndrome, age related macular degeneration, macular dystrophy, atrophic age related macular degeneration, neovascular AMD, diabetic maculopathy, proliferative diabetic retinopathy (PDR), cystoid macular oedema, central serous retinopathy, retinal detachment, intra-ocular inflammation, glaucoma, posterior uveitis, choroideremia, Leber hereditary optic neuropathy, glaucoma (including open-angle glaucoma, angle-closure glaucoma, normal-tension glaucoma, and pigmentary glaucoma), and Fuch's Corneal Dystrophy (also known as Fuch's dystrophy).

EXAMPLES

Example 1—Materials and Methods

AAV Vector Production and Purification

AAV vectors were produced using the transient triple transfection method as previously described. See, Nass et al. (2017) Mol. Ther. Methods Clin. Dev., 9:33-46, the disclosure of which is herein incorporated by reference in its entirety. Briefly, HEK293 cells were transfected using polyethylenimine, PEI, and a 1:1:1 ratio of three plasmids (ITR vector, AAV rep/cap and Ad helper plasmid). The vector plasmid contained the vector genome CBA-EGFP and ITR sequences from AAV2. EGFP expression was driven by the CMV enhancer, chicken beta actin hybrid promoter (CBA) as described. See, Miyazaki et al (1989) Gene, 79(2):269-277, the disclosure of which is herein incorporated by reference in its entirety. The AAV rep/cap helpers contained rep sequences from AAV2 and serotype specific capsid sequences with the nomenclature, rep2/cap2, rep2/cap5, rep2/cap7 etc. The pAd helper used was pHelper (Stratagene/Agilent Technologies, Santa Clara, CA). AAV vectors were purified by affinity column chromatography (AVB Sepharose High Performance medium; GE Healthcare) as previously described (Nass et al. (2017) Mol. Ther. Methods Clin. Dev., 9:33-46).

Analyzing rAAV Vector Purity Using SYPRO™ Ruby Protein Gel Stain

Samples from purified vector were loaded onto a NuPage 4-12% Bis-Tris gel (Invitrogen). Typically, $1\text{-}5\times10^{10}$ vgs of purified vector was analyzed. The gel was stained with SYPRO™ Ruby Protein Gel Stain (Life Technologies).

LC/MS Intact Protein Analysis

As previously described, (Jin et al. (2017) Hum. Gene Ther. Methods, 28(5): 255-267, the disclosure of which is herein incorporated by reference in its entirety) AAV virions were first concentrated with an Amicon® ultra centrifugal filter (0.5 mL, 10 kDa MWCO) and then washed with 25 mM Tris pH 7.1 three times. The concentrated AAV virions were denatured with 10% acetic acid vortexed and further diluted with an equal volume of HPLC water. The final acetic acid concentration was 5%, 50 μL of AAV solution (~2-5 μg of proteins) was injected to Acquity™ UPLC coupled with a Xevo™ G2-XS QTOF MS instrument (Waters™, Milford, MA). The separations were performed on a BEH C8 column (2.1×100 mm) at a flow rate at 250 μL/min. Mobile phase A and mobile phase B were 0.1% formic acid in water and acetonitrile, respectively. The final gradient for the C8 column was as follows: from 10% B to 20% B over 6 min, from 20% B to 30% B over 10 min, then from 30% to 38% B over 40 min. The capillary voltage and sampling cone voltage of the mass spectrometer were set at 3.5 kV and 45 V, respectively. The mass spectra were acquired in positive sensitivity mode over m/z 500-4000. MaxEnt1 in MassLynx software version 4.1 was used for protein deconvolution.

Enzymatic Digestions of AAV1 and AAV2 VPs

AAV2-EGFP generated from triple transfection as well as producer cell line process (~10 μg capsid protein) was first concentrated using Amicon® Ultra centrifugal filters (10 kDa MWCO), denatured with 6 M Guanidine-HCl, 50 mM Tris at pH 8.5. The proteins were reduced with 5 mM DTT at 60° C. for 30 minutes in darkness and then alkylated with 15 mM iodoacetamide at room temperature for 30 minutes. The samples were buffer exchanged into 25 mM Tris pH 7.1 for digestion using a Bio-Spin® 30 Tris column. After buffer exchange, the samples were split into two aliquots. Each aliquot was digested with trypsin at 1:25 or Asp-N at 1:50 enzyme:protein ratio (wt/wt) for 2 hours at 37° C., respectively.

UPLC/MS/MS Peptide Mapping

The protein digests were analyzed by UPLC/MS/$MS^E$ using an Acquity™ UPLC-Xevo™ G2-XS qTOF mass spectrometer system (Waters™, Milford, MA). The separation was achieved using a BEH300 C18 column (2.1×150 mm) with a linear gradient from 2% to 40% B (0.1% formic acid in acetonitrile) over 68 min at a flow rate of 250 μL/min. For MS, the capillary voltage and sampling cone voltage were set 3.0 kV and 30 V, respectively. The mass spectra were acquired in the positive sensitivity $MS^E$ mode in the m/z range of 500-2000.

Determination of Deamidation Levels in AAV VPs

The extracted ion chromatograms (XIC) of peptides and their corresponding deamidated species were used for calculation of deamidation levels.

Generation of AAV Capsid Variants

Deamidation variants N57D and G58D were based on pim45BD-cap2, an AAV helper plasmid that contained both rep and cap sequences from AAV2. Fragments containing the designated mutations were synthesized (Genscript™) and subcloned into pim45BD-cap2. Mutations were verified by DNA sequencing (Genewiz™). Acetylation variants were constructed as above, using pHLP19-cap5.2, a helper plasmid that contained rep from AAV2 and cap from AAV5, as the parental plasmid. AAV2-HBKO and AAV5 arginine mutant capsid plasmids were generated by site-directed mutagenesis using the QuikChange™ Lightning Site-Directed Mutagenesis kit (Agilent Technologies, Santa Clara, CA), according to the manufacturer's protocol. The pIM45BD plasmid was used to generate AAV2-HBKO using a PCR mutagenesis primer designed to alter the codons encoding arginine 585 and 588 on VP3 to alanine. The sequence of the mutagenic primer used to generate the R585A and R588A mutations was: TATCTACCAACCTCCAGGCAGGCAACGCACAAGCAGCTACCGCAG (SEQ ID NO:11). The AAV5-G474R, AAV5-N564R and AAV5-N573R mutants were generated using the AAV5 rep/cap plasmid (pHLPcap5.2) as a template and PCR mutagenic primers designed to change the respective arginines to alanines. The sequence of the mutagenesis primer used to introduce the G474R mutation was CCAGGTTCCAGCGCTGGGTTCGGCC (SEQ ID NO:12). The sequence of the mutagenesis primer used to introduce the N564R mutation was CCGCGTGGCGTACCGCGTCGGCGGGCAG (SEQ ID NO:13). The sequence of the mutagenesis primer used to introduce the N573R mutation was CAGTGGTGGAGCTCTGTCTGTTGGTGGCCATCTG (SEQ ID NO:14). All mutations were confirmed by DNA sequencing.

NHP Studies

Four adult male cynomolgus monkeys (*Macaca fascicularis*) were screened for neutralizing antibodies against AAV5 and AAV2 prior to surgery as previously described. Animals considered seronegative (serum titers≤1:4) were included in the study. Cynomolgus monkeys were assigned to two groups and were administered either AAV2-HBKOEGFP or AAV5GFP. Animals were dosed via subretinal injection to both eyes once on Day 1 of the dosing phase at a volume of 120 μL/eye. The diluent was Alcon® BSS® with 0.014% polysorbate 20. Dosing syringes (1.0 mL Luer Lok™ Becton Dickinson Product 309628 or equivalent) were filled and affixed to a DORC 23-gauge needle with an extendible 41-gauge subretinal injection needle on the day of dosing using aseptic procedures under a laminar flow hood. Injections were administered within 30 minutes of filling the DORC injector. Dosing was performed in both eyes (OU) of each animal. Animals were anesthetized with intramuscular injections of atropine (0.01 mg/kg), ketamine (2 to 10 mg/kg), and dexmedetomidine (0.25 mg/kg). Following the procedure, the anesthesia was reversed with atipamezole (0.25 mg/kg). The anesthesia regimen was adjusted based on the responsiveness of animals and according to Covance veterinary staff. Eyes were cleaned with an approximate 1% povidone iodine solution (prepared with sterile saline and 5% povidone iodine) and rinsed with sterile saline. An approximate 2.5% povidone iodine solution was used at the dose site prior to injection. The injection was performed following a study-specific procedure, briefly described as follows. Pupils were dilated with a topical mydriatic agent. The DORC Disposable Dual bore injection needle (23-gauge) was introduced directly through the sclera in the superior temporal quadrant of the globe approximately 3 mm posterior to the corneal limbus and moved through the vitreous under visual control using a surgical microscope viewing through a dilated pupil, with a modified fundus viewing lens placed on the cornea. The 41-gauge cannula tip was advanced from the 23-gauge needle and gently touched the retinal surface. The dose was injected through the neural retina into the subretinal space, resulting in a subretinal bleb. The 41-gauge cannula tip was retracted, and the 23-gauge needle was withdrawn. A topical antibiotic and steroid ointment (Neo-poly-dex) was instilled in each eye following all other post-dose ocular procedures. The injection occurred in a small portion of the retina in the mid-arcade region.

Fundus Autofluorescence Imaging

The Fundus Autofluorescence Imaging was done once during the pre-dose phase and during Weeks 2, 4, and 6 of the dosing phase. Animals were anesthetized (remained under anesthesia used for dosing) for fundus autofluorescence imaging. Eyes were dilated with a mydriatic agent (1% tropicamide). Fundus autofluorescence images were taken of each eye to include the subretinal dose sites and the fovea. Images were taken with a Heidelberg SPECTRALIS® instrument.

Tissue Processing of NHP Retina

On Day 43 of the dosing phase, all animals, having been fasted overnight, were anesthetized with sodium pentobarbital, exsanguinated, and necropsied. The eyes from each animal were injected with and submerged in chilled 4% paraformaldehyde and stored in a refrigerator, set to maintain 2 to 8° C., for 48 to 72 hours. The eyes were then embedded in paraffin, sectioned, and slides were prepared for IHC analysis. From the temporal calotte, 20 serial sections were taken from the fovea. In addition, 20 serial sections were taken every 250 μm for a total of eight steps from the remaining temporal calotte. One slide from the fovea and one slide from each of the eight steps of the temporal calotte were stained with hematoxylin and eosin.

Immunohistochemistry Analysis

A single slide through the fovea of each eye was examined by bright field microscopy. The presence or absence of GFP expressing photoreceptors was noted at the time of observation. The antibody that identified GFP was tagged with a chromogen that produced a brown precipitate. The antibodies that identified rhodopsin were tagged with a chromogen that produced a red precipitate. The presence or absence of rod photoreceptors that expressed GFP was noted. Selected representative images were recorded. In order to assess the GFP expression, immunohistochemistry was performed. Briefly, sections were washed with xylene three times for 5 min each. Sections were rehydrated by washing in graded series of alcohol, rehydrated in distilled water. Following antigen retrieval, endogenous peroxidase activity was blacked with hydrogen peroxide and nonspecific protein binding with normal goat serum. Sections were incubated with GFP and Rhodopsin antibodies. After washing, sections were incubated with ChromoPlex™ 1 Dual Detection for bond (Leica, Wetzlar, Germany) were used for the visualization of dual histochemical staining, according to the manufacturer's instructions. Sections were counterstained with hematoxylin, and then dehydrated with ethanol before mounting. Paraffin embedded sections were deparaffinized and rehydrated in a graded ethanol. Antigen retrieval was performed, and sections were blocked with protein block serum free reagent (Dako). Sections were then incubated with mouse anti GFP and were incubated over night at 4° C. and then washed incubated with anti-mouse Alexa Fluor 488 secondary antibody. The sections were washed in PBS, and cover slipped using mounting solution and imaged using a microscope.

Immunofluorescence

The remaining slide was labeled for GFP and DAPI (immunofluorescence). The slides were stained for the immunofluorescence detection of GFP and co-stained with DAPI to visualize the nuclei.

Photoreceptor Cell Counting and Quantification of Transduction

The step sectioned slide set from each eye was reviewed and the slide that contained the fovea was selected for analysis. The photoreceptor layer was imaged from one border of the subretinal bleb to the other. Morphometric analysis was performed using NIH ImageJ (version 1.49t) to determine the percentage of photoreceptors expressing the GFP transgene within the borders of the subretinal bleb.

Subretinal and Intravitreal Injections

At postnatal day P45, mice were placed under general anesthesia with intraperitoneal injection of ketamine (90 mg/kg)/xylazine (9 mg/kg). Pupils were dilated with topical application of 1% tropicamide (Akorn Pharmaceuticals, Lake Forest, IL). To perform Subretinal Injections, aliquots of AAV were thawed on ice, Fluorescein (AK-FLUOR, 10%—Akorn Pharmaceuticals, Lake Forest, IL) was added to the viral preparation to aid in visibility of AAV delivery. Under visualization with an operating surgical microscope (PSMT5N, World Precision Instruments, Sarasota, FL, USA), an incision was made through the sclera immediately posterior to the nasal limbus using a beveled 30-gauge needle. Through this incision, a 35-gauge blunt needle (NF35BL, World Precision Instruments, Sarasota, FL, USA) which is mounted in to the SilFlex tubing connected to NanoFil syringe was introduced into the subretinal space. Viral suspension was injected over 20 seconds into the subretinal space using a programmable micro syringe pump with foot pedal control (UMP3, UltraMicroPump, World Precision Instruments, Sarasota, FL, USA). The needle was held in place for at least 20 sec after completion of the injection. Fundus and OCT examination was performed following injection to visualize the location of injection and thus ensure that AAV vectors were injected into the subretinal space. A 3.5% Akten (Lidocaine hydrochloride ophthalmic gel, Akron Pharmaceuticals, Lake Forest, IL) Ophthalmic gel was applied to the cornea as a topical anesthetic. A small amount of neomycin/polymyxin B/dexamethasone ophthalmic ointment (Alcon Laboratories Inc., Fort Worth, TX, USA) was spread over the eye before placing the animal in a 37° C. incubator to recover from anesthesia. For intravitreal injections, mice were anesthetized and eyes were dilated same as described above. 1 ul of AAV suspension was injected in to the vitreous through sclera which is 1 mm from the limbus using 35G beveled-tip needle attached to a 10-μL Nanofil syringe through Sil.Flex™ tubing (World Precision Instruments, Sarasota, FL, USA). OCT was performed immediately to check for any retinal damage following injections. A small amount of Akten and triple antibiotic ophthalmic ointment was applied on the eye before placing at 37° C.

Quantification of rAAV Transduction in Mouse Retinal Lysates

Following euthanasia, eyes were collected, frozen immediately on dry ice and stored at −80° C. for future dissection. All dissection steps were performed under a dissecting microscope using cold instruments, while maintaining the eye in a frozen state during dissection. The anterior segment was removed using a razor, excess tissue was removed from the back of the eye if needed, and the lens was then removed. Retinal lysates were generated by placing the frozen vitreous humor, retina, and eye cup in 200 μl of cell lysis buffer from the EGFP ELISA Kit and homogenized for at 4° C. (Fisher Bead Mill). EGFP protein was quantified using an EGFP ELISA kit (Abcam catalog #ab171581). Total protein levels were quantified using the BCA Protein Assay Kit (Pierce). The levels of eGFP were normalized to total protein. Genome titers were determined by qRT-PCR (7500 Real-Time PCR System; Applied Biosystems) using TaqMan™ Universal Master Mix (Thermo Fisher) with primers specific for the polyadenylation signal. Vector levels were expressed as genomes per μg protein.

NHP Retinal Explants

All animal procedures were conducted in compliance with the Animal Welfare Act, the Guide for the Care and Use of Laboratory Animals, the Office of Laboratory Animal Welfare and in accordance with the ARVO Statement for the Use of Animals in Ophthalmic and Vision Research. Fresh monkey eyes without known ocular diseases were obtained from Biomere (Biomere, Worcester, MA) where they were enucleated 15 min after animals were sacrificed. The eyes were placed in Neurobasal medium and transported immediately on ice. Under aseptic conditions, all extra-ocular connective tissues were removed, and the eyes were disinfected with 70% ethanol followed by washing with PBS. Before starting the experiment, six-well transwell culture plates were pre-incubated with 2 ml of complete Neurobasal™ medium (Neurobasal Medium (Thermo Fisher Scientific, Waltham, MA; cat. no. 21103049), supplemented with 1% N-2 Supplement (Thermo Fisher Scientific; cat. no. 17502048), 2% B-27 Supplement (Thermo Fisher Scientific; cat. no. 17504044), 1% GlutaMAX Supplement (Thermo Fisher Scientific; cat. no. 35050-061), 0.2 μg/mL of recombinant human beta-NGF (R&D Systems, Minneapolis, MN; cat. no. 256-GF-100), and 0.4 μg/mL recombinant human EGF (R&D Systems; cat. no. 236-EG-200)) beneath the transwell insert and 0.5 ml in the transwell insert in humidified cell culture incubators at 37° C. and in 5% $CO_2$. An incision was made with an 18G needle around 5 mm below the limbus. By using this incision as an entry point for the scissors, the anterior part of the eye, cornea, lens and vitreous, were removed from each eye leaving posterior eyecups consisting of intact neural retina, choroid, and sclera. Next, 3 flaps were made to open the eye cup by making three cuts towards optic nerve head. While the whole eye cup is submerged in the complete Neurobasal complete medium, an 8 mm biopsy punch was used to cut equatorial, full-thickness posterior segment explants. The retina was subsequently peeled off by gently applying a piece of dry sterile filter paper onto the ganglion cell layer, lifting off the neural retina, and placing the filter paper with attached retina onto the culture insert, photoreceptors facing down and filter paper was gently removed with fine forceps. After 24 hours, media was replaced with fresh complete Neurobasal media and half of the AAV was injected directly beneath each retinal explant, creating a bleb similar to that formed in vivo when performing therapeutic sub-retinal injections. An additional half of virus was added to the culture medium that was placed beneath the transwell insert. Finally, the explants are incubated at 37° C. and 5% $CO_2$. AAV vectors at a dose of 1.8×1011 total genome copies was used for each explant. Media was changed every other day and cultures were maintained for 6 days post transduction. After 7 days of culture, retinal explants were rinsed in 1× phosphate-buffered saline (PBS) and fixed for 3 h in 4% paraformaldehyde (PFA). Explants were washed 3 times with PBS to remove the residual PFA and cryoprotected in graded sucrose 10-30%, after which they were frozen in optimum cutting temperature compound at −80° C. 13 μm thick sections were cut using a cryostat (CryoStar™ NX70 cryostat, Thermo Fisher Scientific, Waltham, MA) and mounted with vector shield DAPI (Vector Lab, Peterborough, UK). The native EGFP expression was observed and images were captured using an inverted fluorescence microscope (Axio Observer Z1; Carl Zeiss, Inc., Oberkochen, Germany) using appropriate excitation and detection settings.

Example 2—Translational Fidelity of AAV2HBKO in the NHP Retina

The transduction activity of a novel AAV2 capsid variant in the mouse retina, was previously reported (Sullivan et al., 2018). The AAV2 variant had amino acids R585A and R588A mutated which are required for binding to its receptor, heparin sulfate proteoglycans, to generate a variant referred to as AAV2-HBKO. Compared to parental AAV2, the AAV2-HBKO vector displayed low-transduction activity following intravitreal delivery to the mouse eye; however, following its subretinal delivery, AAV2-HBKO resulted in significantly greater photoreceptor transduction. Without being bound to any theory, the AAV transduction profile in mouse is not always predictive of transduction potential in the NHP, thus the performance of AAV2HBKO in the NHP retina was evaluated to determine if this novel variant demonstrated a similar improvement in retinal transduction in this species. The objective of the study was to compare enhanced green fluorescent protein (eGFP) expression in photoreceptors from an AAV5 and an AAV2HBKO vector, when administered as a single dose via subretinal injection to male cynomolgus monkeys. Male cynomolgus monkeys (*Macaca fascicularis*) were assigned to two groups, and AAV5-eGFP or AAV2-HBKO-eGFP were administered at a dose of $1\times10^{12}$ vg/eye as described in Table 2. The vector preparations were analyzed using a series of optimized assays to confirm quality.

TABLE 2

List of NHPs and AAV doses injected

| Group | No. of Males | Eye | Treatment | Dose Level (vg/eye)[a] | Dose Concentration (vg/mL)[b] |
|---|---|---|---|---|---|
| 1 | 2 | OU | AAV5-eGFP | $1.2 \times 10^{11}$ | $1.0 \times 10^{12}$ |
| 2 | 2 | OU | AAV2 HBKO-eGFP | $1.2 \times 10^{11}$ | $1.0 \times 10^{12}$ |

In Table 2, OU represents injection into both eyes; [a]Both eyes of each animal were dosed. Animals were dosed at a volume of 120 μL/eye; [b]Dose concentrations were based on the test article as supplied.

Figure 1B:
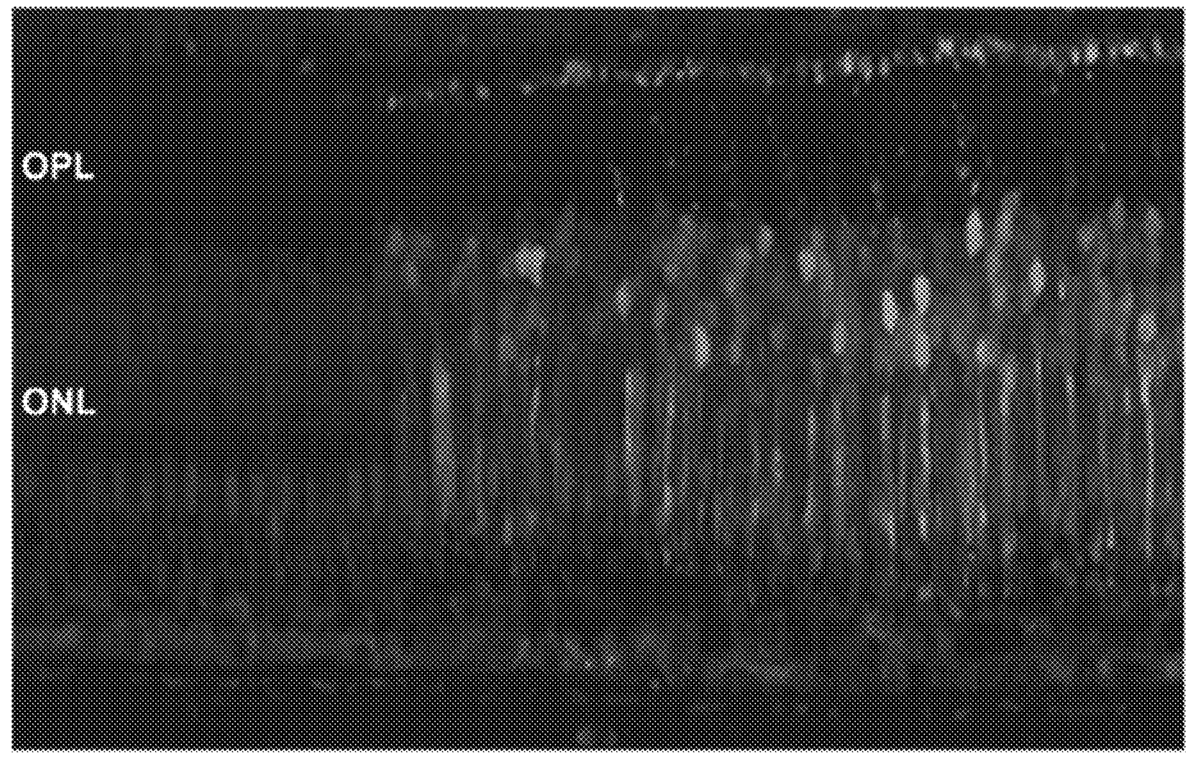

Six weeks post-vector administration, the animals were euthanized and the eyes were processed for histological sectioning. The section that passed through the fovea was selected for analysis (FIG. 1A). The assessment of eGFP expression in photoreceptors was evaluated by FA (fundus auto fluorescence) and IHC following administration of AAV5-eGFP or AAV2-HBKO-eGFP. Both vectors harbored a human rhodopsin promoter driving expression of eGFP. The animals were euthanized approximately 6 weeks following vector administration and the eyes processed for paraffin embedding and histological sectioning. The slides were stained for the immunofluorescence detection of eGFP, (FIG. 1B) and images were sequentially collected from one edge of the subretinal bleb to the other. Expression of the eGFP transgene appeared to be uniform across the subretinal bleb. Without being bound to any theory, in areas where there were fewer rod photoreceptors (adjacent to and within the fovea) the transgene expression was diminished, confirming the fidelity of the human rhodopsin promoter in restricting expression to the rod photoreceptors. Previously, AAV5 was shown to transduce cone photoreceptors when transgene expression was under the control of a ubiquitous promoter. Quantification of the percentage of photoreceptor transduction under the bleb revealed that AAV5 and AAV2-HBKO demonstrate equal photoreceptor transduction activity in the NHP retina, (an average of 61% of the photoreceptors were transduced by both AAV5 and AAV2-HBKO), Table 3.

TABLE 3

Percentage of transduced photoreceptors within the area of the subretinal bleb

| Group | Treatment (vg/eye) | Animal ID | GFP positive PR (% transduced PR under bleb) OD | GFP positive PR (% transduced PR under bleb) OS |
|---|---|---|---|---|
| 1 | AAV5: | P0001 | 41.7 | 50.1 |
|  | $1.2 \times 10^{11}$ | P0002 | 77.1 | 76.1 |
| 2 | AAV2 HBKO: | P0101 | 59.8 | 59.1 |
|  | $1.2 \times 10^{11}$ | P0102 | 50.9 | 75.9 |

In Table 3, PR represents photoreceptors; OD represents right eye; OS represents left eye.

Figure 2A:
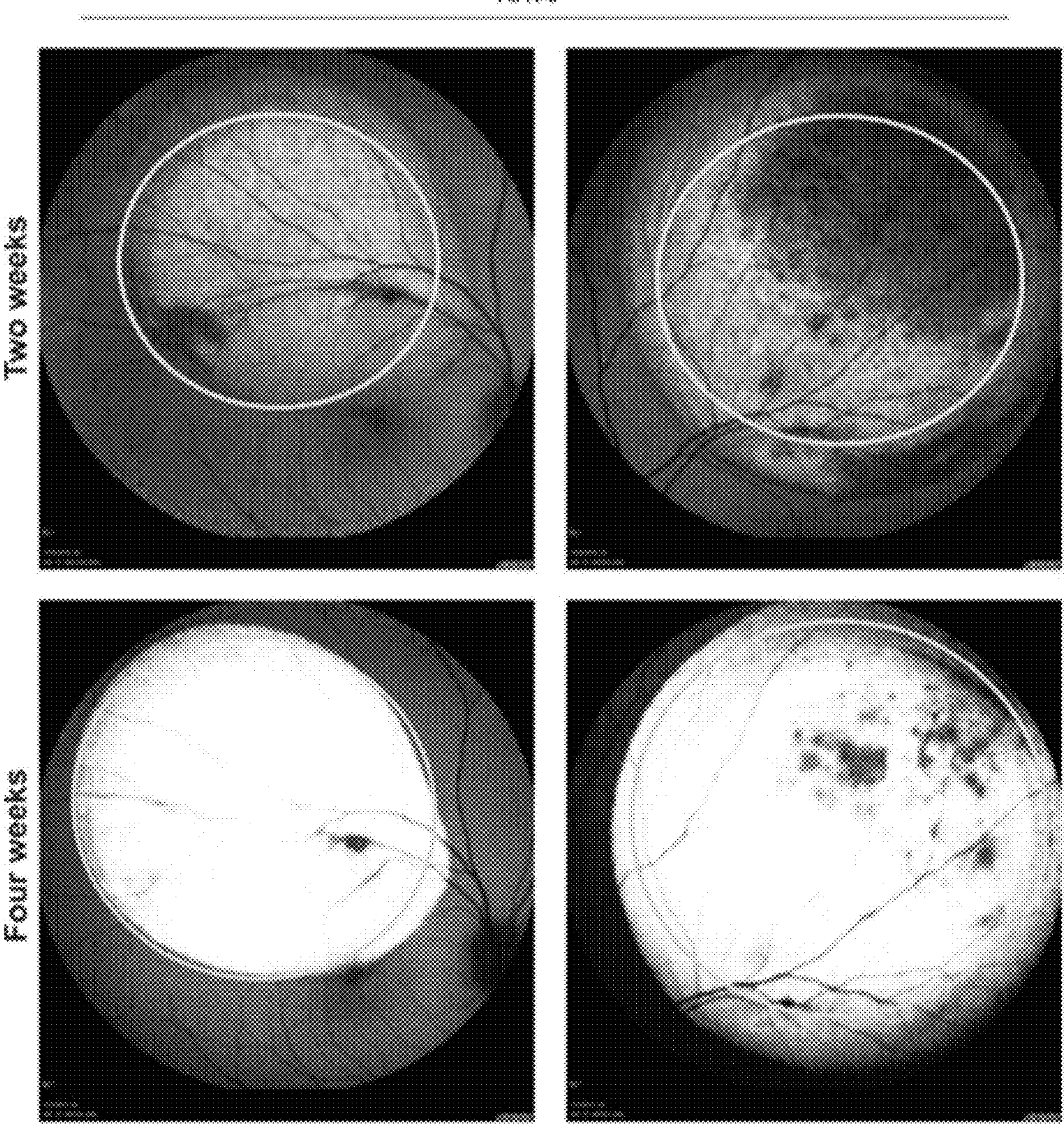
Figure 2B:
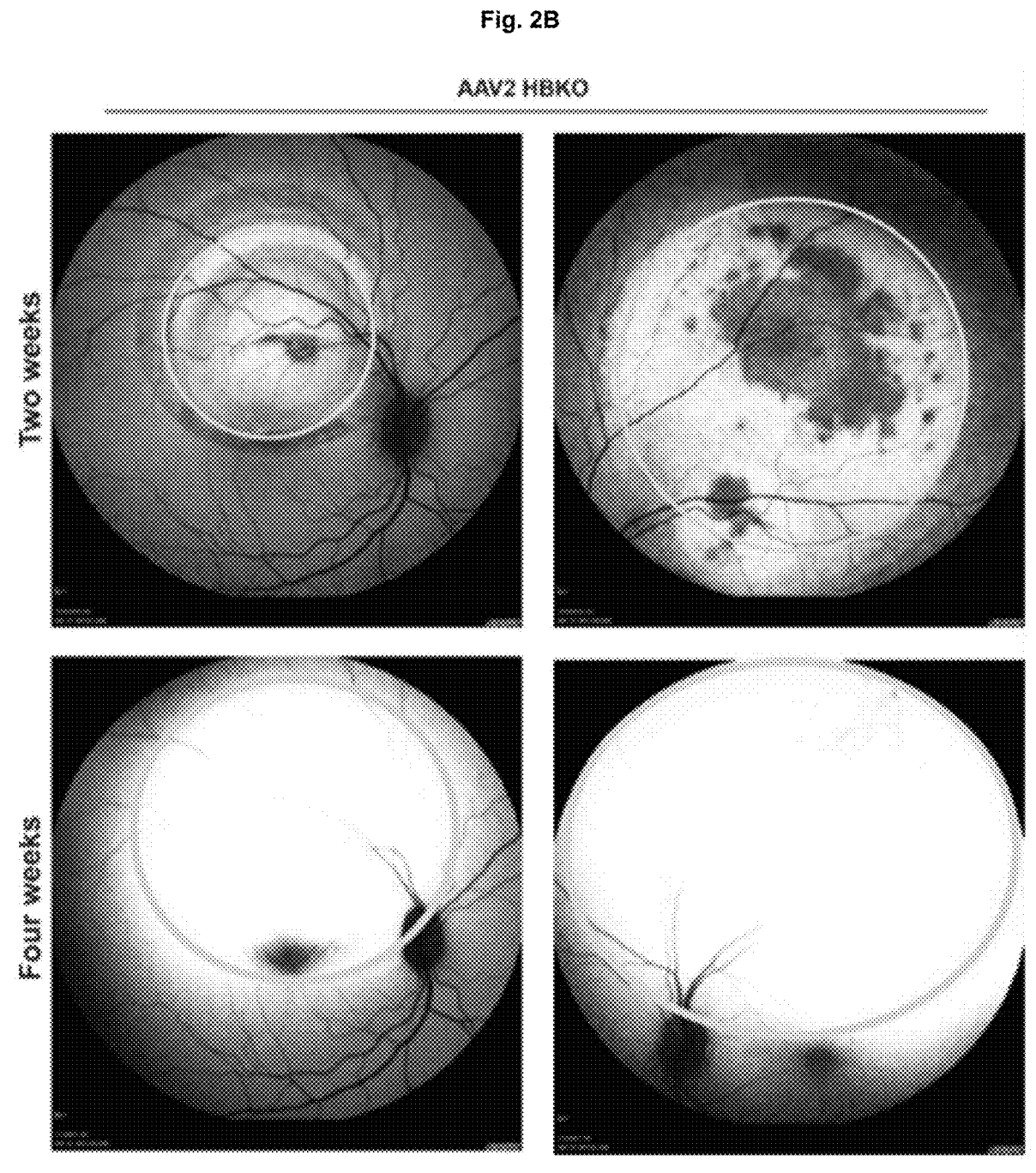
Figures 3A, 3B:
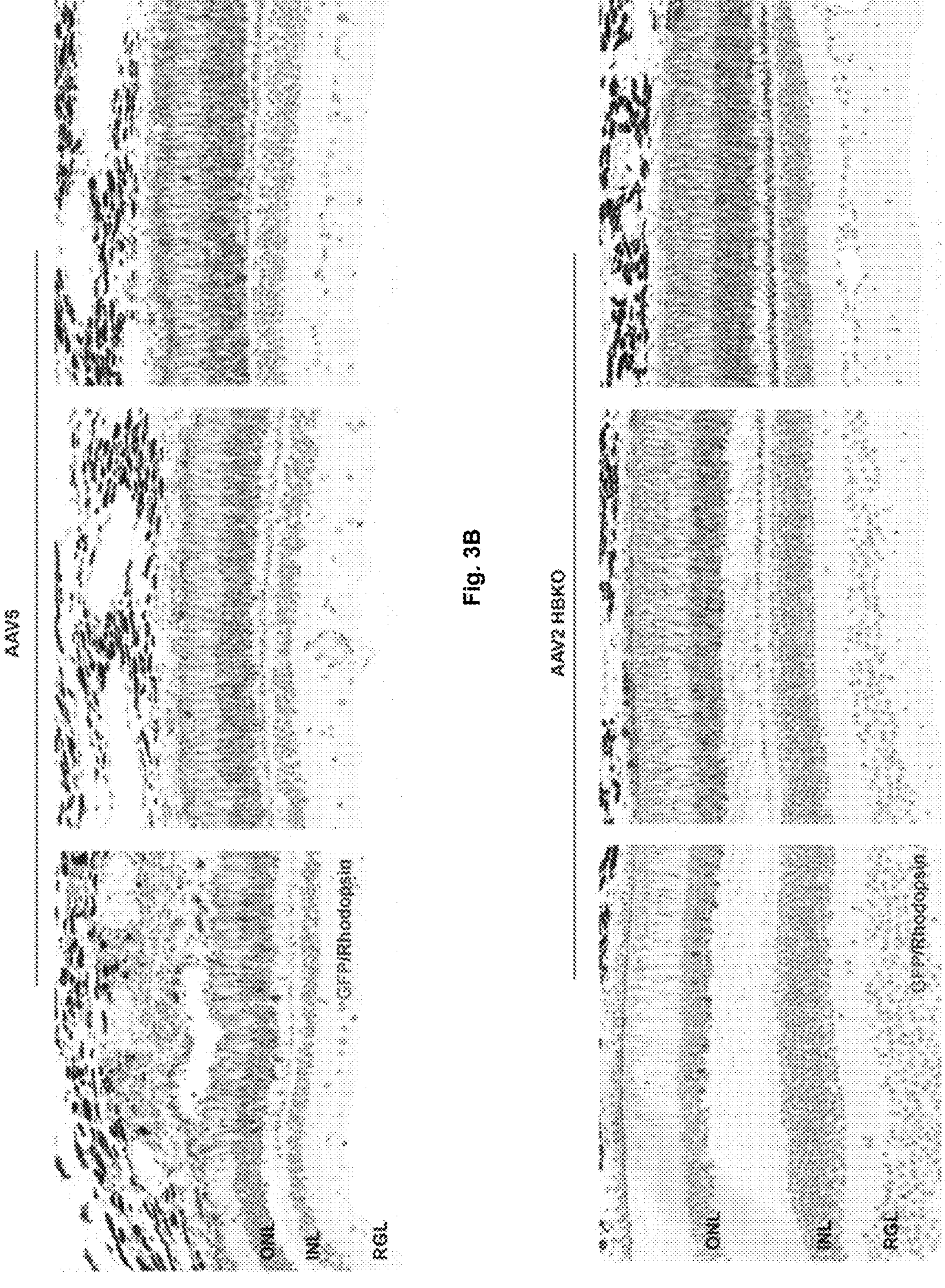
FIG. 3A-FIG. 3B depict subretinal injections in NHP showing superior transduction ability of AAV2-HBKO over the AAV5 in retina. Relative transduction efficiencies of AAV5 and AAV2-HBKO in rod photoreceptors were compared following subretinal injection. Paraffin embedded retinal sections were immunolabelled with anti-GFP antibody and anti-rhodopsin antibody for the detection of eGFP (brown) as well as rhodopsin (red). Immunohistochemistry analysis around the bleb region showed that the transduction of the AAV5 vector does not appear to spread from the margin of the subretinal bleb, the transition at the margin is abrupt (FIG. 3A). AAV2HBKO-eGFP was highly efficient at transducing photoreceptors and displayed ability to spread from the bleb and tapers off in areas not lifted by the injection process (FIG. 3B). The AAV transduction was restricted to rod photoreceptors. ONL-outer nuclear layer, INL-inner nuclear layer RGL-retinal ganglion cell layer.

Additionally, the expression of eGFP was monitored using sdOCT with autofluorescence imaging capabilities. eGFP was observed two- and four-weeks following vector administration. The intensity of eGFP signal increased with time and was confined to the retina, within the margin of the subretinal bleb in the eyes treated with AAV5eGFP, (FIG. 2A). Expression of eGFP from the eyes treated with AAV2-HBKOeGFP extended well past the margin of the subretinal bleb, (FIG. 2B). Separate slides were co-stained with an anti-eGFP antibody and anti-rhodopsin antibody for the immunohistochemical detection of eGFP as well as rhodopsin, to confirm that only rod photoreceptors were transduced. FIG. 3 shows a histologic survey of the subretinal bleb. Without being bound by any theory, immunohisotochemistry for rhodopsin (red) and eGFP (brown), in paraffin embedded tissue, revealed that the transduction of the AAV5 vector did not appear to spread from the margin of the subretinal bleb; the transition at the margin is abrupt (FIG. 3A). Transduction spread from the AAV2HBKO-eGFP bleb and tapered off in areas not lifted by the injection process (FIG. 3B). Colocalization of eGFP and rhodopsin indicated that the transduced cells were rod photoreceptors. The overall architecture of the retina was preserved although there were changes to the RPE including hypertrophy, displacement of pigment, and displacement of cells.

Figures 4A, 4B:
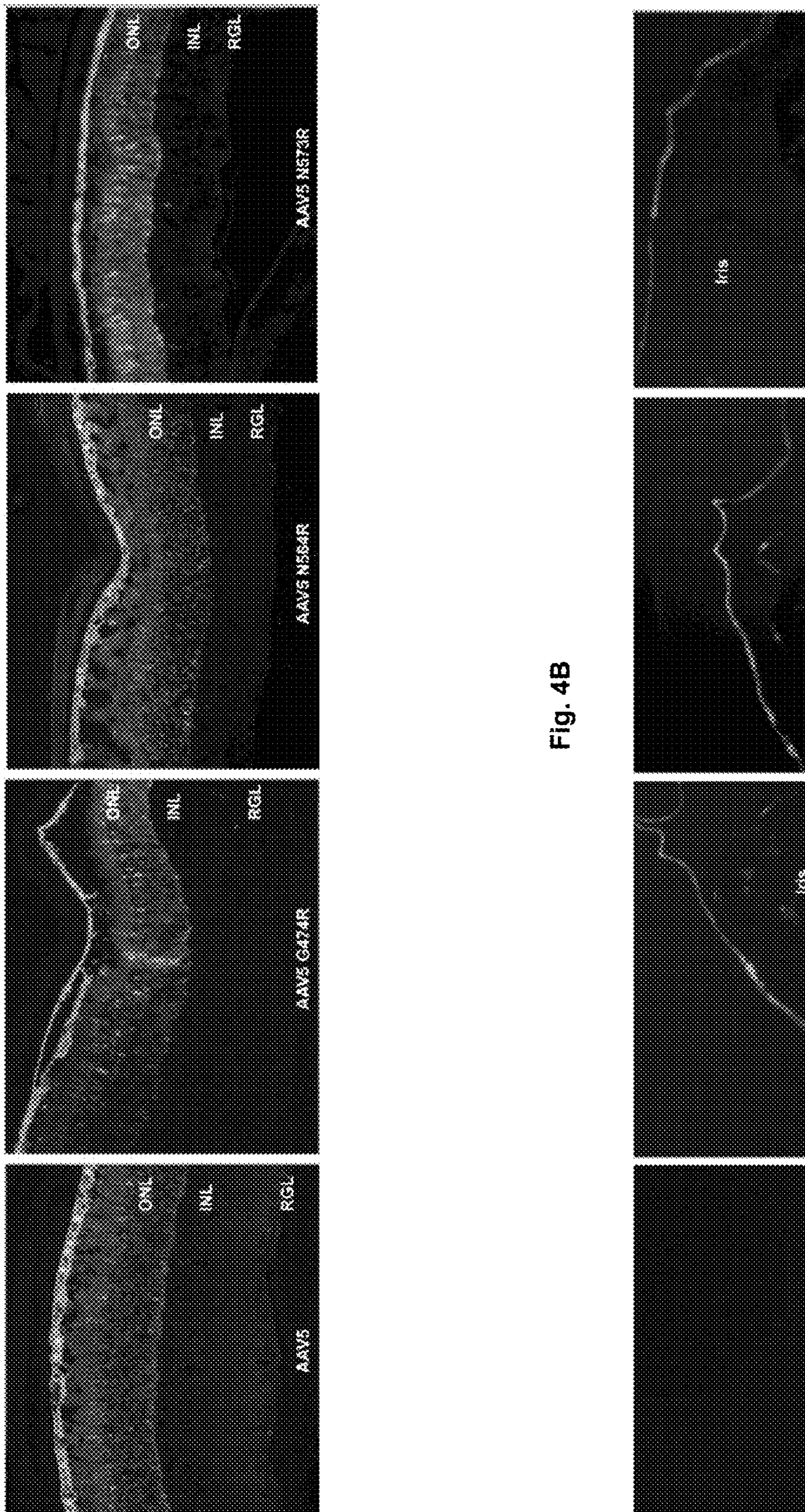
FIG. 4A-FIG. 4B depict comparison of retinal and corneal transduction efficiency between AAV5 and AAV5 arginine variants.

Example 3—Evaluation of the Transduction Potential of AAV5 Arginine Variants in the Retina The AAV2HBKO variant revealed the importance of arginines, and by extension surface charge, on transduction activity in the retina. The effect of adding surface arginines was further explored with another capsid, AAV5, a serotype that has a high affinity for photoreceptors when delivered subretinally. AAV5 variants AAV5G474R, AAV5N564R and AAV5N573R were generated and their tropism in the mouse retina following intravitreal and subretinal delivery was evaluated. The surface map of AAV2 was compared to that of AAV5, and this helped guide the choice of amino acids to mutate in the AAV5 capsid, for the generation of arginine rich AAV5 variants. The AAV5 variants were produced at yields that were 2-3 fold less than yields achieved with parental AAV5, but variants retained the same capsid protein ratio as parental AAV5. First, subretinal delivery of the AAV5 arginine variants was evaluated in the wild type mouse retina and their transduction activity compared to that of the parental AAV5 capsid. FIG. 4A shows the performance of AAV5, AAV5G474R, AAV5N564R and AAV5N573R following subretinal delivery of $1\times10^{9}$ vgs of each vector harboring the identical CBA-eGFP expression cassette. There was no significant difference in the ability of the AAV5 arginine variants to transduce the retina when compared to parental AAV5 Analysis of native eGFP fluorescence revealed that the AAV5G474R, AAV5N564R and AAV5N573R variants transduced the ONL and RPE cells, to the same level as parental AAV5-eGFP, FIG. 4A. Additionally, the AAV5 arginine variants were further evaluated following intravitreal delivery to the mouse retina, at the same vector dose of $1\times10^9$ vgs per eye. EGFP fluorescence analysis of the transduced retinae, FIG. 4B, confirmed that all of the AAV5 arginine variants, AAV5G474R, AAV5N564R and AAV5N573R, had acquired a novel tropism for corneal endothelium cells. Parental AAV5 showed no transduction activity with intravitreal delivery, (FIG. 4B). The AAV5 variants demonstrated no transduction in the outer retina, including photoreceptors and RPE, following intravitreal delivery, with very low levels of eGFP expression observed in the INL and Mueller cells.

Example 4—Probing the Role of Acetylation on AAV Transduction

The AAV2HBKO and AAV5 arginine variants were generated using a rational design approach, using knowledge of receptor binding and surface charge respectively. Additional variants were generated using knowledge gained from LC/MS analysis of the AAV capsid, which identified novel post translational modifications, PTMs, (Jin et al., 2017). N-terminal acetylation on VP1 and VP3 capsid proteins was previously reported, (Jin et al., 2017). To further explore this attribute a series of AAV5 acetylation variants were generated to elucidate the role PTMs on AAV5 biology in the retina. The mutations that were introduced into the AAV5 capsid sequence are described in Table 4; this included changing the amino acid after the initiating methionine from one that has a high frequency of acetylation, (alanine or serine), to an amino acid with a low frequency of acetylation, (glycine or proline). These changes were performed separately on the AAV5 VP1 and VP3 capsid proteins. In addition, combined changes were made in both AAV capsid proteins. The AAV capsid protein VP2, showed no evidence of acetylation in previous studies, (Jin et al 2017), so the VP2 sequence remained unchanged from the parental sequence. AAV5 deacetylation variants were analyzed by LC/MS to confirm acetylation status and the results are shown in Table 4.

TABLE 4

LC/MS of AAV5 deacetylation variants

| Lane | AAV5 mutant | Yield (vg/mL) | Theoretical | Experimental | Δ mass (VP1) | Theoretical | Experimental | Δ mass (VP2) | Theoretical | Experimental | Δ mass (VP3) | Note |
|---|---|---|---|---|---|---|---|---|---|---|---|---|
| 1 | S2G | 1.40E+13 | 80234 | nd | | 65283 | 65293 | 10 | 59463 | 59472 | 9 | VP1 not detectable |
| 2 | S2P | 1.10E+13 | 80314 | 80313 | 1 | 65283 | 65291 | 8 | 59463 | 59470 | 7 | confirmed |
| 3 | S194G | 1.00E+13 | 80234 | nd | | 65253 | 65261 | 8 | 59391 | 59398 | 7 | confirmed |
| 4 | S194P | 1.90E+13 | 80336 | 80346 | 10 | 65293 | 65292 | 1 | 59431 | 59430 | 1 | confirmed |
| 5 | S2G/ S194G | 6.00E+12 | 80234 | 80243 | 9 | 65253 | 65261 | 8 | 59391 | 59398 | 7 | confirmed |
| 6 | S2P/ S194P | 1.00E+13 | 80314 | 80324 | 10 | 65293 | 65300 | 7 | 59431 | 59438 | 7 | confirmed |

Figure 5:
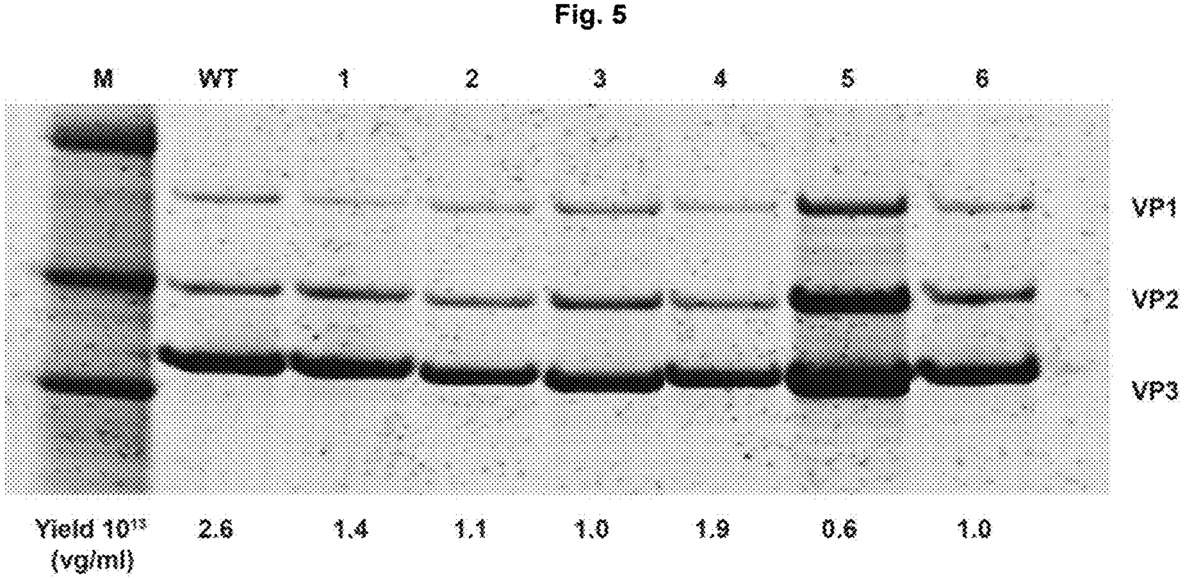
FIG. 5 depict AAV5 acetylation mutants maintaining wild type levels of capsid protein expression and vector yields.

Table 4 shows LC/MS analysis to confirm the masses of VP1, VP2 and VP3 in AAV5 acetylation mutants (VP1 of AAV5S2G and AAV5S194G was not detected by mass spectrometer due to incomplete chromatographic separation of the capsid proteins); nd refers to not detectable. Lanes correspond to those as indicated in FIG. 5.

Irrespective of the amino acid change, i.e. glycine or proline, all AAV5 deacetylation mutants were confirmed to have reduced acetylation. LC/MS analysis confirmed the correct molecular weights for each AAV5 capsid protein mutants. No acetylation was observed in the S to P mutants while 10% acetylation was observed in S to G mutants. The acetylation mutants showed equivalent packaging efficiencies, compared to wild type AAV5, suggesting that the novel amino acid changes had not adversely affected AAV vector production, or capsid protein ratios, FIG. 5.

Figure 6A:
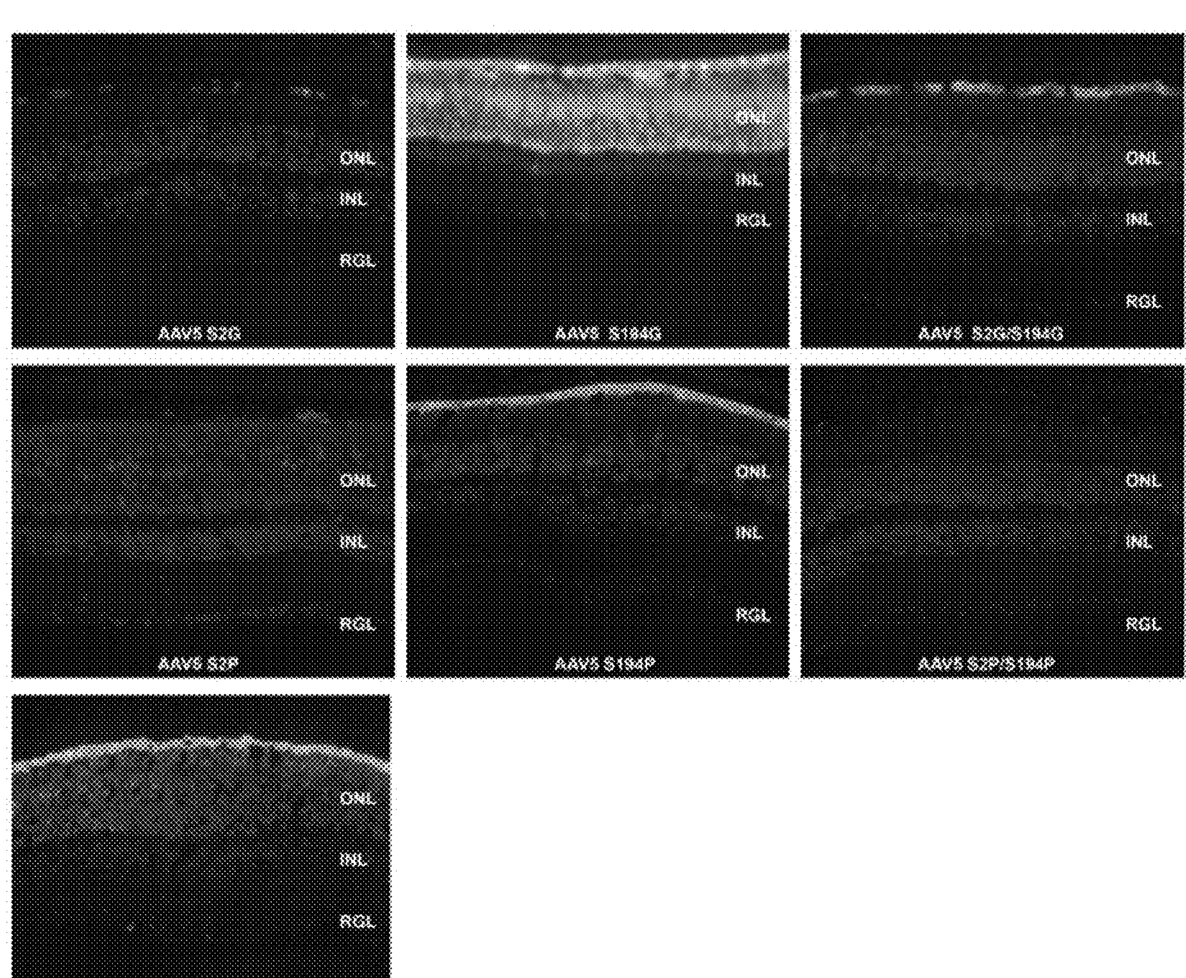
FIG. 6A-FIG. 6C depict effect of AAV5 deacetylation on photoreceptor transduction.
Figure 6B:
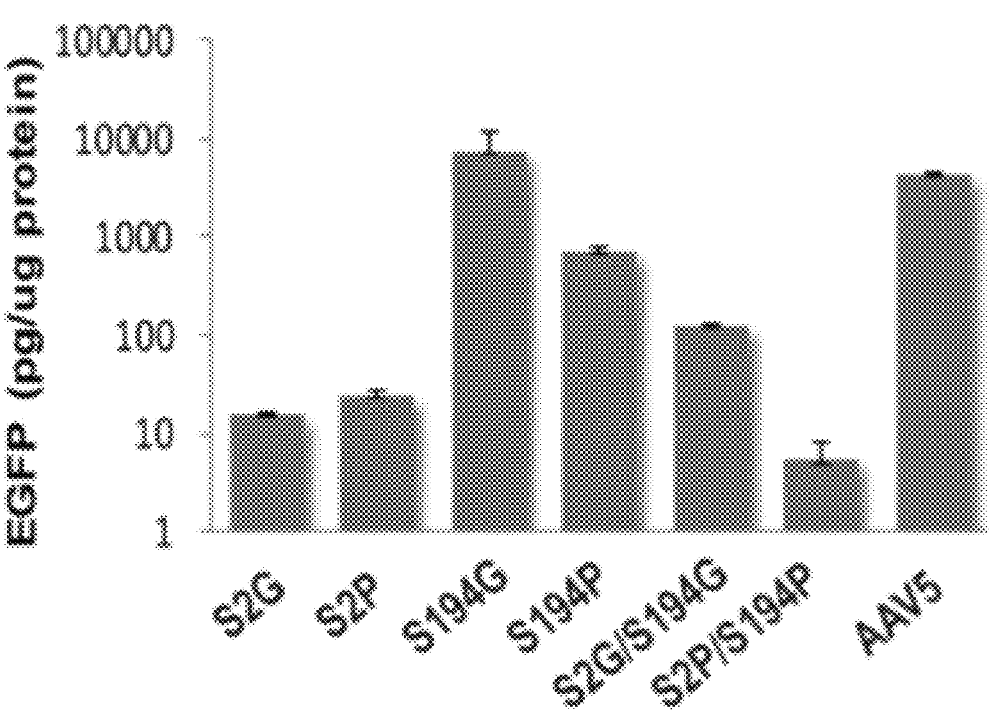
Figure 6C:
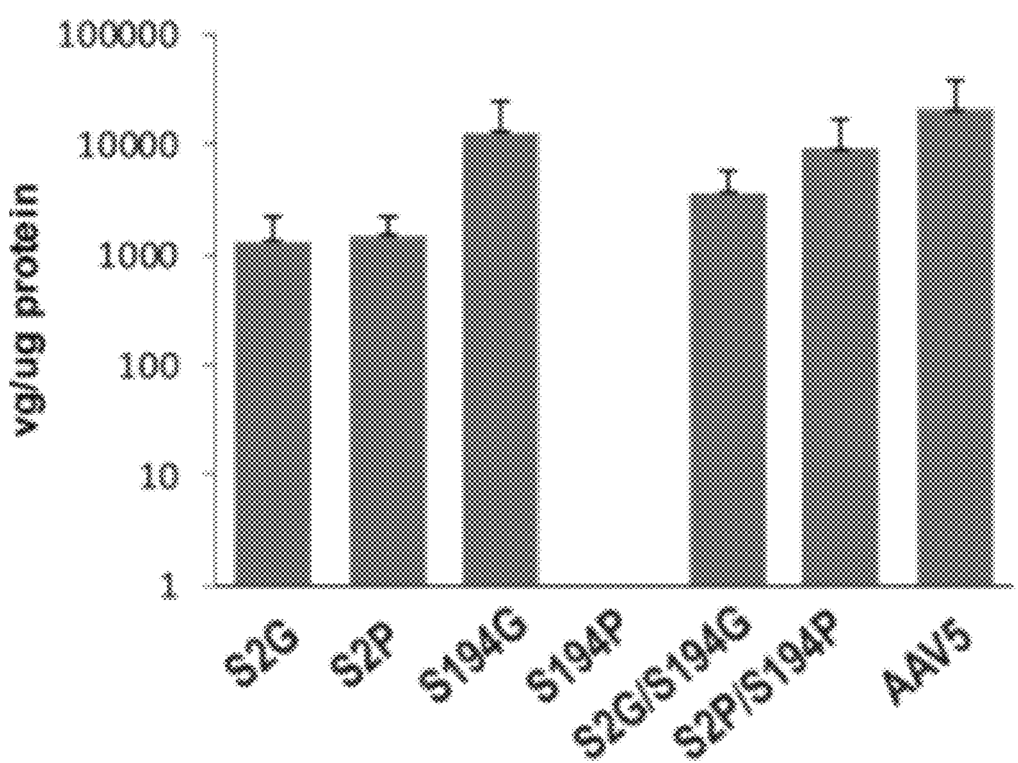

The transduction efficiencies of the AAV5 acetylation variants were compared to wild type AAV5, in vivo, following sub retinal injection to the mouse. Wild type mice were injected with $1\times10^9$ vgs AAV5-CBA eGFP or one of each of the AAV5 acetylation mutants, harboring the same CBA-eGFP expression cassette. As previously shown, (FIG. 4A), subretinal injection of AAV5-eGFP resulted in robust eGFP expression in the outer retina, (FIG. 6A). The acetylation mutants AAV5S2G, AAV5S2P, AAV5S194P, AAV5S2G/S194G and AAV5S2P/S194P showed reduced levels of eGFP expression in the retina as evidenced by eGFP fluorescence of injected retinas (FIG. 6A) and EGFP protein levels, (ELISA) (FIG. 6B). The acetylation mutant AAV5S194G-eGFP, showed a significant increase in eGFP expression in photoreceptor cells compared to parental AAV5-eGFP, (FIG. 6A and FIG. 6B). This was demonstrated at the protein level by eGFP ELISA and eGFP fluorescence of transduced retina. Analysis of the vector genome copy number per ug retinal protein revealed that the increase in retinal transduction was not a function of increased uptake of the AAV5S194G-eGFP vector into retinal cells, the vector genome copy number/ug retinal protein for the acetylation variants all trended lower than parental AAV5 eGFP vector in treated retinas (FIG. 6C).

Figure 7A:
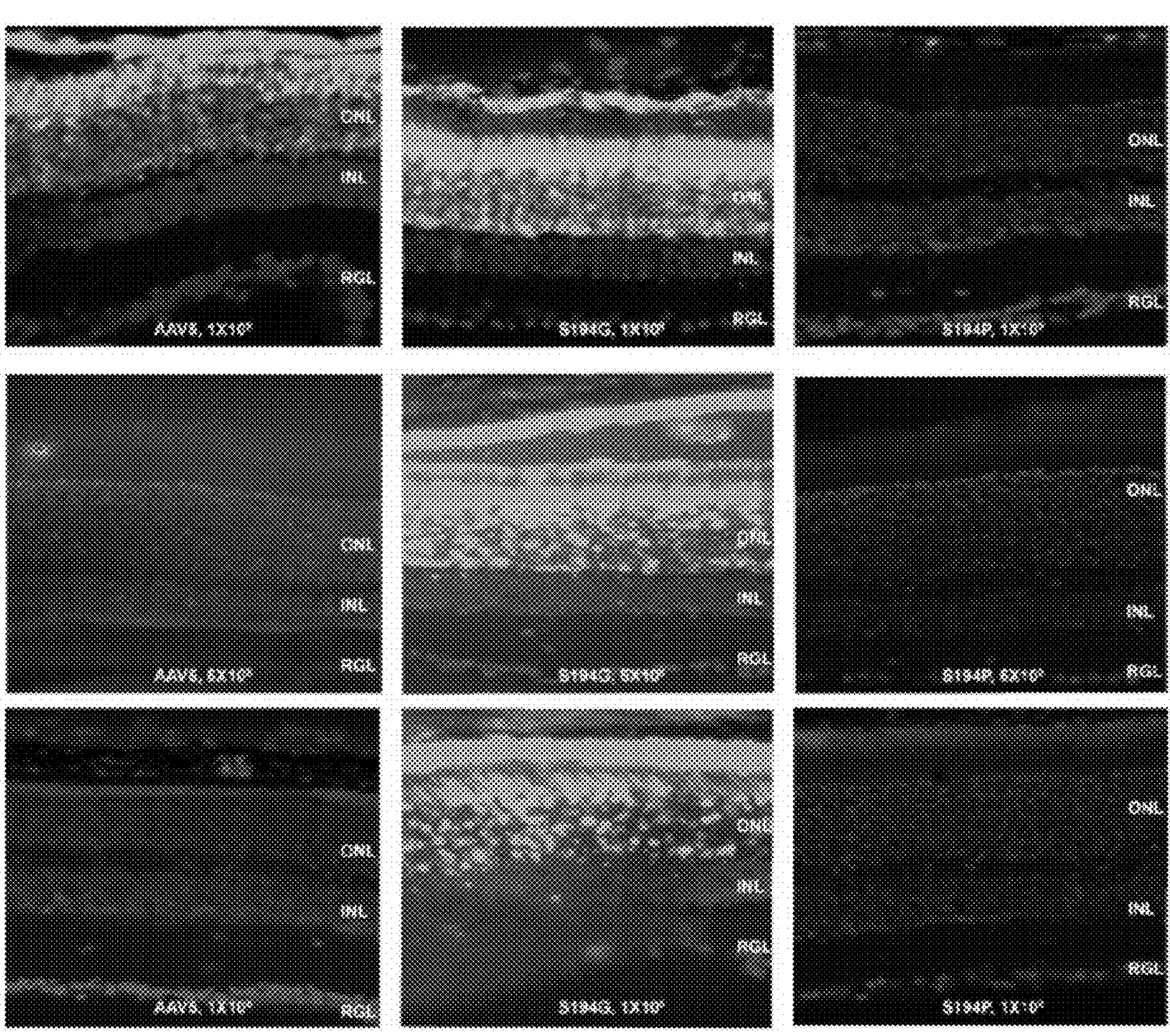
FIG. 7A-FIG. 7C depict comparison of GFP expression after subretinal delivery of AAV5 deacetylation variants in a dose dependent manner.
Figure 7B:
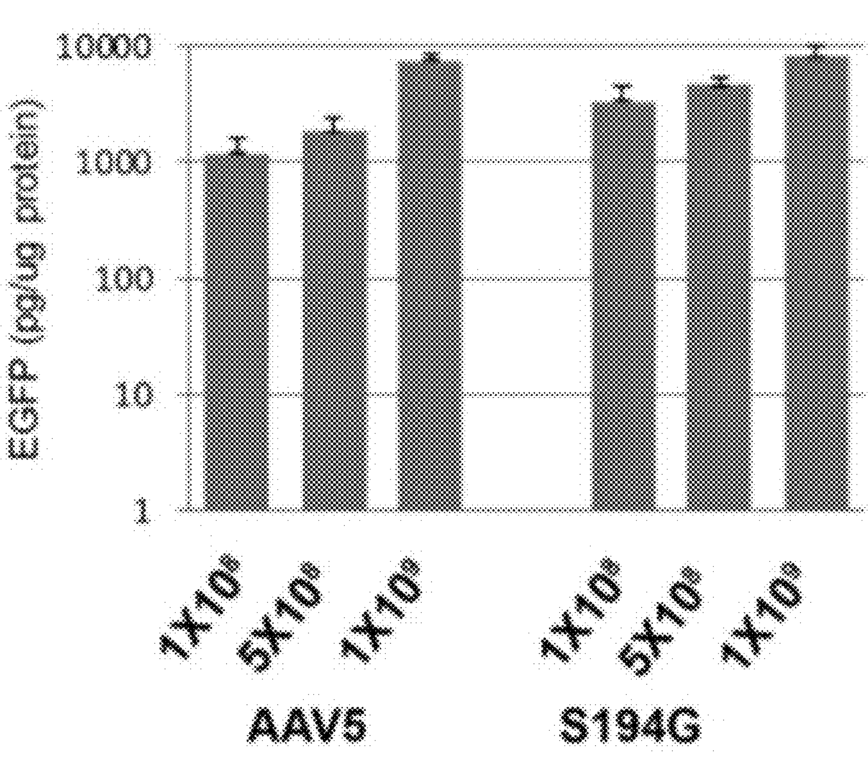
Figure 7C:
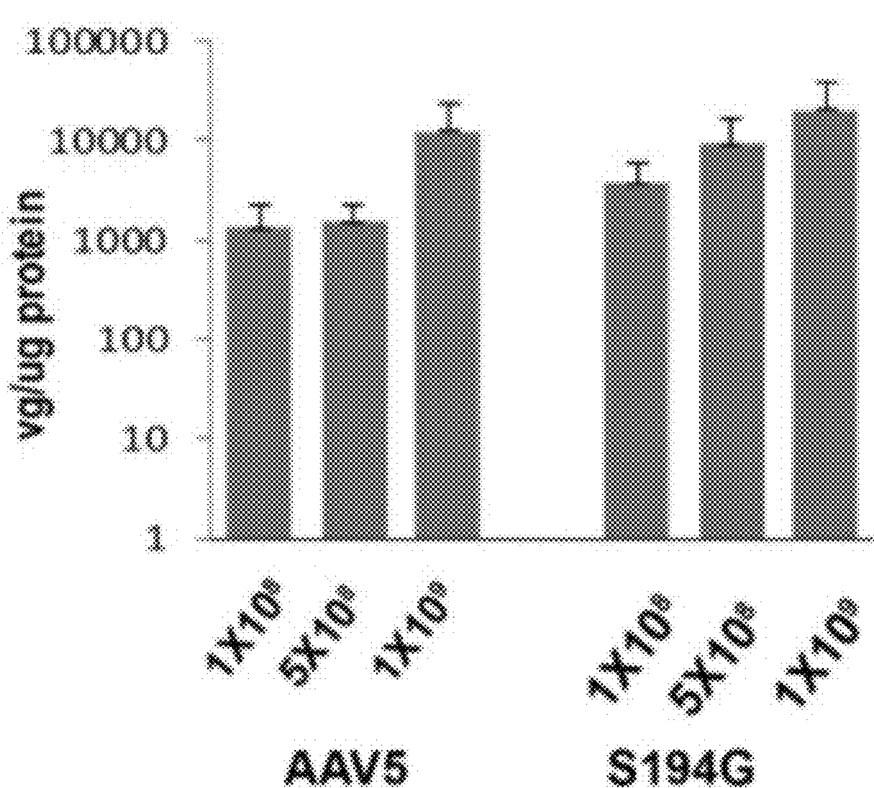

The transduction properties of the acetylation mutants AAV5-S194G-eGFP and AAV5-S194P-eGFP were further evaluated in a dose response study and their performance compared to AAV5-eGFP. Increasing doses, $1\times10^8$-$1\times10^9$ vgs of AAV5-S194G-eGFP, AAV5-S194P-eGFP or AAV5-eGFP were administered subretinally to a wild type mouse. At a dose level of $1\times10^9$ vgs, the AAV5 vector showed robust transduction of photoreceptor cells. The acetylated mutant AAV5S194P, as seen in the previous result, showed a significantly reduced expression compared to AAV5, while the AAV5-S194G variant, demonstrated a significant increase in photoreceptor cell transduction, FIG. 7A. At lower doses of vector, $5\times10^8$ and $1\times10^8$ vgs, there was a marked decrease in eGFP expression in the retinas that had received the AAV5-eGFP vector, while the retinas transduced with AAV5-S194G-eGFP had robust eGFP expression in photoreceptors; even at doses as low as $1\times10^8$ vgs. AAV5S194P-eGFP showed little transduction of photoreceptors at all doses evaluated, (FIG. 7A). EGFP protein levels were confirmed to be higher in retinas treated with the AAV5S194G-eGFP compared to AAV5-eGFP at all doses evaluated, with the difference being more significant at the lower doses. Without being bound by any theory, this may be because of saturation of eGFP expression at the higher vector doses, (FIG. 7B). Analysis of vector genome copy number per ug retinal tissue revealed a dose response for all vectors evaluated; retinas transduced with the AAV5-eGFP vector had similar vector genome copies/ug retinal protein, as those retinas treated with either the AAV5S194G-eGFP or AAV5S194P-eGFP acetylation variants, (FIG. 7C). Without being bound by any theory, when VP1 N terminal acetylation was preserved and VP3 N-terminal acetylation reduced, there was a significant improvement in retinal transduction compared to parental AAV5.

Figure 8A:
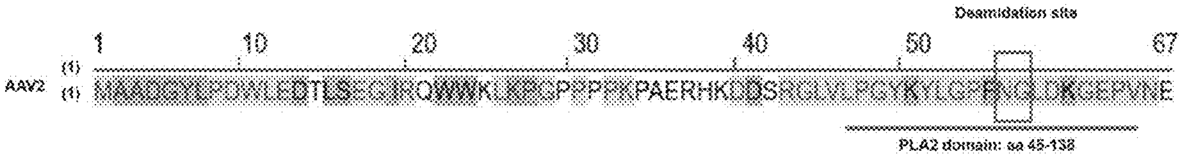
FIG. 8A-FIG. 8C depict altering deamidation levels within the PLA2 domain of AAV2 VP1 not impacting capsid protein expression or vector yields but potentially impacting potency.
Figure 8B:
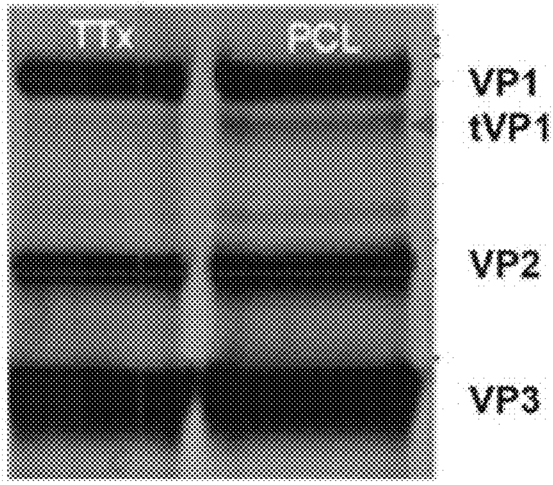

Example 5—Evaluating the Role of Deamidation on AAV2 Transduction in the Retina Analysis of quality attributes of AAV vectors generated using the producer cell line production platform, including post translational modifications on the AAV capsid proteins, revealed several observations. Specifically, the producer cell line process, in the context of AAV2 vectors, resulted in AAV vector preparations that consistently had a protein running below VP1, as compared to a similar AAV2 vector produced via the triple transfection production platform, (FIG. 8B). LC/MS analysis revealed the protein to be a truncated form of VP1 protein, (tVP1), lacking the first 34 amino acids, with acetylated A35 confirmed to be the N terminal amino acid. Without being bound by any theory, it may be that tVP1 was a result of deamidation at a neighboring asparagine, N57, resulting in the proteolytic cleavage of VP1 at acetylated A35 to generate tVP1, (FIG. 8A). LC/MS analysis confirmed that the deamidation status of N57, in the context of the AAV2 PCL derived vector, was higher at 18.4%, compared to 6.7%, for a comparable AAV2 vector generated by triple transfection, Table 5.

TABLE 5

Percentages of deamidation in AAV2 determined by LC-MS

| AAV2 | Production Platforms | In vitro potency | % of deamidation at 3 different N (G) sites | | |
|---|---|---|---|---|---|
| | | | N57 | N511 | N717 |
| | TTx | 146 | 6.7 | 39.6 | 27.4 |
| | PCL | 340 | 18.4 | 42.3 | 28 |

In Table 5, TTx represents the triple transfection production platform; PCL represents the producer cell line production platform.

Figure 8C:
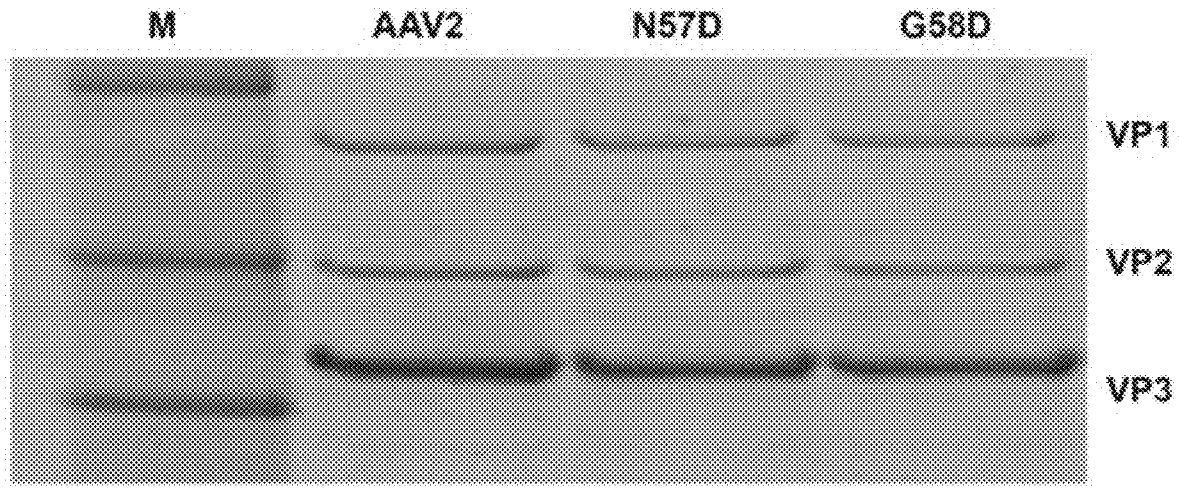

There was no measured difference in deamidation at other potential NG deamidation sites in the AAV2 capsid sequence, including N511 or N717. The infectivity of the AAV2 PCL vector trended lower in an analytical in vitro assay, (Table 5), thus deamidation mutants were generated to further explore the role of deamidation on AAV2 infectivity in the retina. To this end, the N57 deamidation site was mutated to aspartic acid, N57D, to generate a capsid that would be totally deamidated. Additionally, variant G58D was generated to control for the effects of introducing an aspartic acid in this region of the AAV2 capsid sequence. AAV2N57D-eGFP and AAV2G58D-eGFP variants were generated and produced using the triple transfection production method, with variants having similar packaging efficiencies and capsid protein profile (FIG. 8C and Table 6), as the parental AAV2 capsid. LC/MS analysis of the deamidation variants confirmed that, at N57 site, AAV2G58D-eGFP was 1.1% deamidated (to become aspartic acid), wild type AAV2-eGFP was 5.7% deamidated, while the AAV2N57D-eGFP was 100% mutated to aspartic acid, Table 6.

TABLE 6

Quantification of vector yields by qPCR

| | AAV2 | N57D | G58D |
|---|---|---|---|
| % Deamidation | 5.7 | 100 | 1.1 |
| Yield (vg/mL) | $8.7\times10^{12}$ | $5.46\times10^{12}$ | $3.6\times10^{12}$ |

Figure 9A:
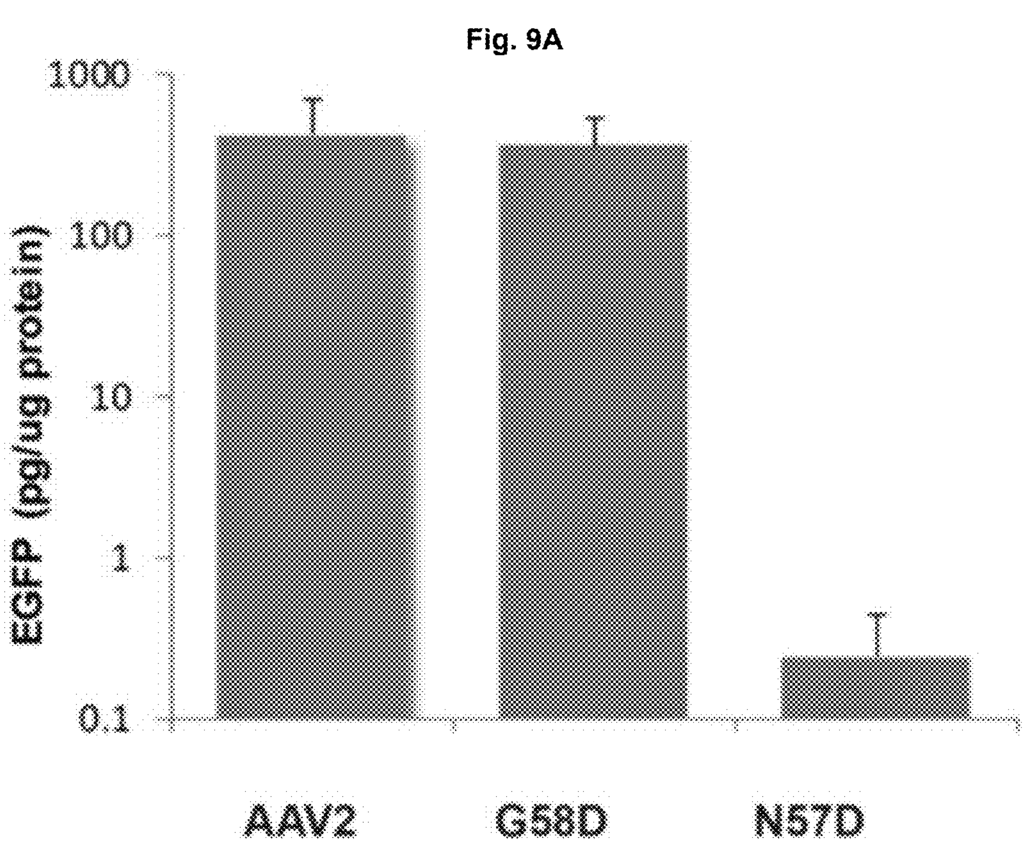
FIG. 9A-9C depict effect of AAV2 capsid deamidation on retinal transduction.
Figure 9B:
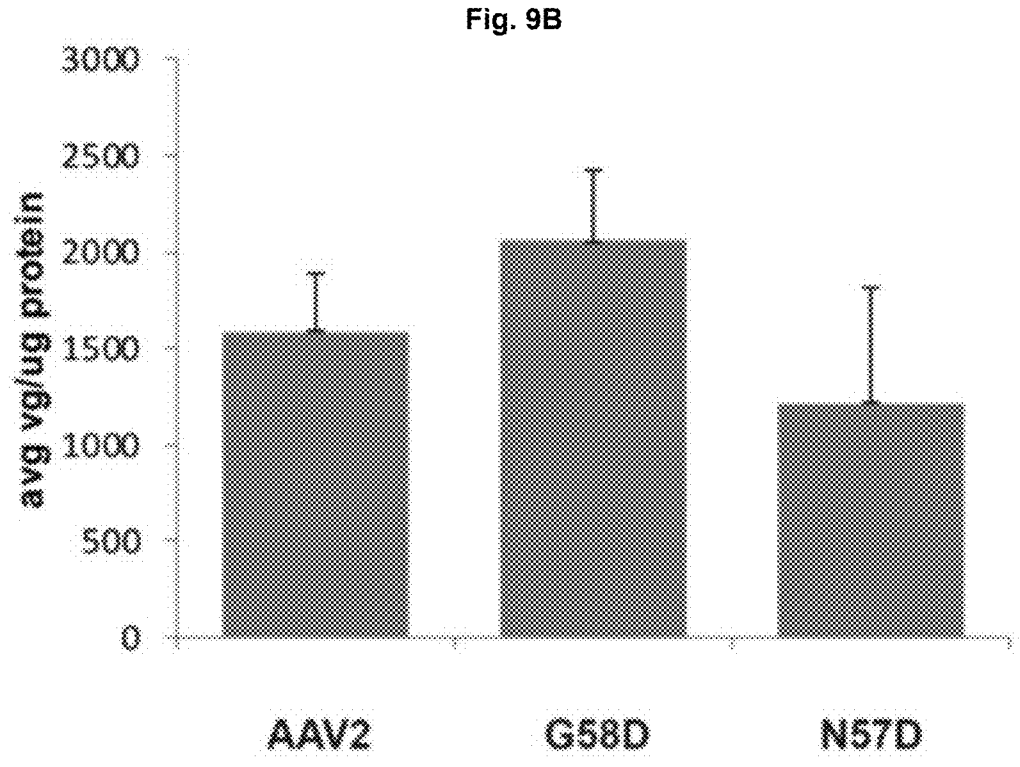
Figure 9C:
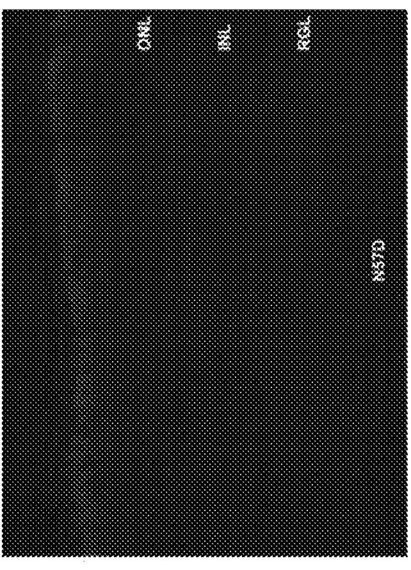
Figure 9C:
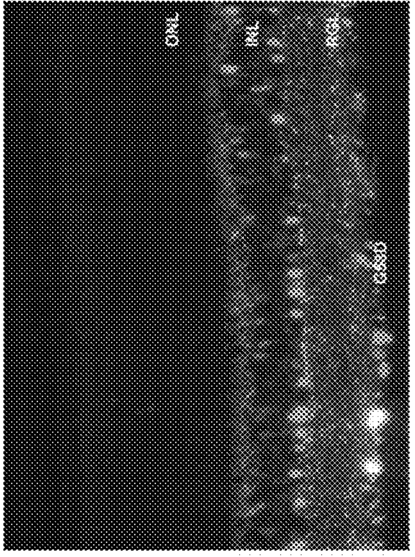
Figure 9C:
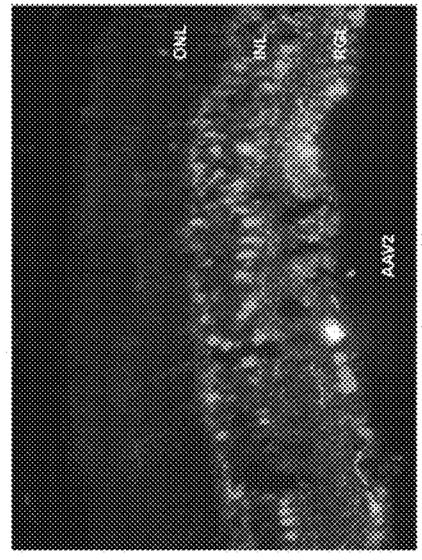

The deamidation variants were next evaluated in vivo to assess the role of this post translational modification on AAV2 transduction activity. Intravitreal delivery of AAV2 eGFP vector to wild type mice, resulted in significant transduction of retinal ganglion cells. A similar result was observed with the AAV2G58D-eGFP variant. Intravitreal delivery of AAV2N57D-eGFP resulted in poor retinal transduction as measured by EGFP fluorescence (FIG. 9C) or ELISA (FIG. 9A). The reduced transgene expression measured with the AAV2N57D-eGFP variant, correlated with reduced cell entry; the vector genome copies per ug of retinal tissue transduced with the AAV2N57D-eGFP variant, trended lower than the levels measured with unmodified AAV2eGFP or AAV2G58DeGFP, FIG. 9B.

Figure 10B:
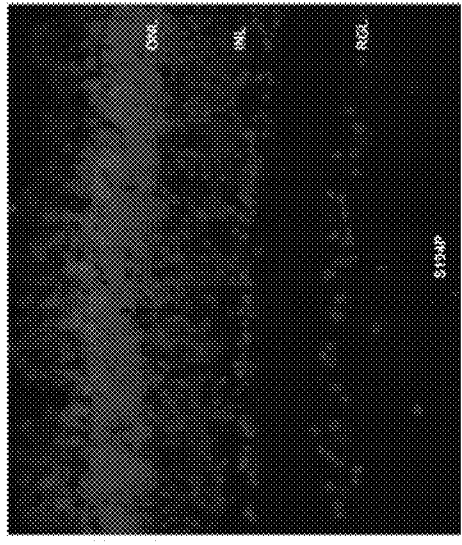
Figure 10B:
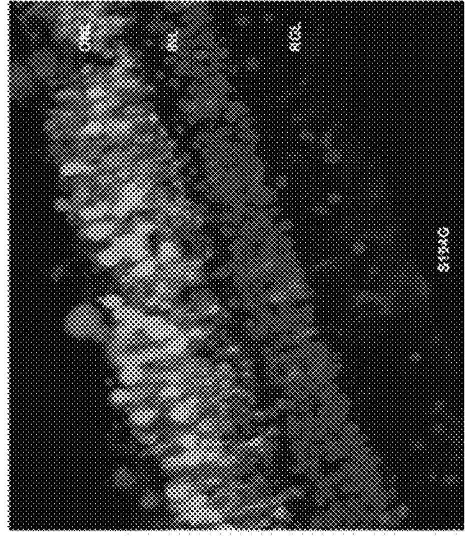
Figure 10B:
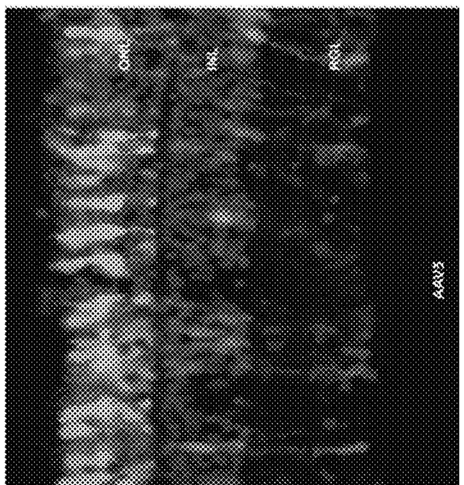

Example 6—Evaluation of AAV2 and AAV5 Capsid Variants in NHP Retinal Explants The use of an ex vivo NHP organotypic explant system was evaluated to test the transduction efficiency and the tropism of the novel variants and to assess translational fidelity of AAV variants between species. Retinal explants from NHPs were established and the transduction efficiency of the deacetylation variants AAV5S194G and AAV5S194P were evaluated. Seven days after plating, the cultured retina retained normal architecture, including intact rod and cone photoreceptor inner and outer segments, a full ONL, and outer to inner retinal connectivity (FIG. 10A). The transduction efficiency of the AAV5 and AAV5 deacetylation variants in the retinal explants mimicked the transduction efficiency observed in the mouse retina, (FIG. 6A) and for unmodified AAV5, mimicked the transduction activity also seen in the NHP retina, FIG. 3A. Confirming what was observed in the mouse retina, (FIG. 7), the AAV5S194G variant showed superior transduction efficiency in the ONL compared to AAV5 parental vector, FIG. 10A and FIG. 10B. Compared to parental AAV5, the AAV5S194P variant revealed decreased transduction efficiency in the NHP retinal explant, similar to its performance in the mouse studies, FIG. 7 and FIG. 8. The authenticity of the organotypic culture was confirmed by the performance of the AAV5-eGFP parental vector, which demonstrated robust transduction of the ONL, FIG. 10A and FIG. 10B, similar to the transduction performance seen with sub retinal delivery of AAV5-eGFP vector to the NHP retina, (FIG. 3A). Evaluation of the deacetylation mutants in the NHP retinal explant model revealed an additional benefit to the AAV5S194G variant over unmodified AAV5: this capsid variant selectively transduces photoreceptor cells, with little transduction observed in the retinal ganglion cell layer, (FIG. 10A and FIG. 10B).

What is claimed is:

1. A modified adeno-associated virus 5 (AAV5) capsid protein comprising the amino acid sequence set forth in SEQ ID NOs: 3, 5, 7, or 9.

2. The modified AAV5 capsid protein of claim 1, comprising or consisting of the amino acid sequence set forth in SEQ ID NO: 3.

3. The modified AAV5 capsid protein of claim 1, comprising or consisting of the amino acid sequence set forth in SEQ ID NO: 5.

4. The modified AAV5 capsid protein of claim 1, comprising or consisting of the amino acid sequence set forth in SEQ ID NO: 7.

5. The modified AAV5 capsid protein of claim 1, comprising or consisting of the amino acid sequence set forth in SEQ ID NO: 9.

6. An isolated nucleic acid encoding the capsid protein of claim 1.

7. The isolated nucleic acid of claim 6, comprising the nucleotide sequence set forth in SEQ ID NOs: 4, 6, 8, or 10.

8. A vector comprising the nucleic acid of claim 6, wherein the vector is selected from the group consisting of a plasmid, a helper viral vector, or an expression vector.

9. A recombinant cell comprising the nucleic acid of claim 6.

10. A method of producing an AAV capsid protein, the method comprising culturing the recombinant cell of claim 9 under conditions whereby the nucleic acid is expressed and the capsid protein is produced.

11. A recombinant adeno-associated viral (rAAV) particle comprising:

(a) an rAAV capsid comprising the modified capsid protein of claim 1; and (b) an rAAV vector comprising a heterologous nucleic acid.

12. The rAAV particle of claim 11, wherein the rAAV vector further comprises inverted terminal repeats (ITRs).

13. A pharmaceutical composition comprising a rAAV particle of claim 11.

14. A modified AAV5 capsid protein comprising:

a G at the position corresponding to amino acid 194;

an R at the position corresponding to amino acid 564; or an R at the position corresponding to amino acid 573;

wherein the modified AAV5 capsid protein is modified from a wild-type AAV5 capsid protein; and wherein numbering of the position is based on the amino acid sequence of the wild-type AAV5 VP1 as set forth in SEQ ID NO:1.

15. The modified AAV5 capsid protein of claim 14, wherein the modified AAV5 capsid protein comprises a G at the amino acid in the modified AAV5 capsid protein corresponding to amino acid 194.

16. The modified AAV5 capsid protein of claim 14, wherein the modified AAV5 capsid protein comprises an amino acid sequence having at least 98% or at least 99% sequence identity with the amino acid sequence set forth in SEQ ID NO:3, wherein the amino acid in the modified AAV5 capsid protein corresponding to amino acid 194 of SEQ ID NO:3 is G.

17. The modified AAV5 capsid protein of claim 14, wherein the modified AAV5 capsid protein comprises an R at the amino acid in the modified AAV5 capsid protein corresponding to amino acid 564.

18. The modified AAV5 capsid protein of claim 14, wherein the modified AAV5 capsid protein comprises an amino acid sequence having at least 98% or at least 99% sequence identity with the amino acid sequence set forth in SEQ ID NO:7, wherein the amino acid in the modified AAV5 capsid protein corresponding to amino acid 564 of SEQ ID NO:7 is R.

19. The modified AAV5 capsid protein of claim 14, wherein the modified AAV5 capsid protein comprises an R at the amino acid in the modified AAV5 capsid protein corresponding to amino acid 573.

20. The modified AAV5 capsid protein of claim 14, wherein the modified AAV5 capsid protein comprises an amino acid sequence having at least 98% or at least 99% sequence identity with the amino acid sequence set forth in SEQ ID NO:9, wherein the amino acid in the modified AAV5 capsid protein corresponding to amino acid 573 of SEQ ID NO:9 is R.

21. The modified AAV5 capsid protein of claim 14 formulated for ocular delivery.

22. The modified AAV5 capsid protein of claim 14, wherein the modified AAV5 capsid protein transduces ocular cells.

23. An rAAV particle comprising:

(a) an rAAV capsid comprising the modified AAV5 capsid protein of claim 14; and (b) an rAAV vector comprising a heterologous nucleic acid.

24. The rAAV particle of claim 23 wherein the heterologous nucleic acid encodes a therapeutic polypeptide or therapeutic nucleic acid;

and is operably linked to a promoter suitable for expression of the therapeutic polypeptide or therapeutic nucleic acid in an ocular tissue.

25. An isolated nucleic acid encoding the capsid protein of claim 14.

26. A vector comprising the nucleic acid of claim 25, wherein the vector is selected from the group consisting of a plasmid, a helper viral vector, or an expression vector.

27. A recombinant cell comprising the nucleic acid of claim 25.

28. A method of producing a modified AAV5 capsid protein, the method comprising culturing the recombinant cell of claim 27 under conditions whereby the nucleic acid is expressed and the modified AAV5 capsid protein is produced.

* * * * *

```
                         SEQUENCE LISTING

<160> NUMBER OF SEQ ID NOS: 14

<210> SEQ ID NO 1
<211> LENGTH: 724
<212> TYPE: PRT
<213> ORGANISM: Artificial Sequence
<220> FEATURE:
<223> OTHER INFORMATION: Adeno-associated virus 5

<400> SEQUENCE: 1

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
```

-continued

```
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu
```

<210> SEQ ID NO 2
<211> LENGTH: 2172
<212> TYPE: DNA
<213> ORGANISM: Artificial Sequence
<220> FEATURE:
<223> OTHER INFORMATION: Adeno-associated virus 5

<400> SEQUENCE: 2
atgtcttttg ttgatcaccc tccagattgg ttggaagaag ttggtgaagg tcttcgcgag 60
tttttgggcc ttgaagcggg cccaccgaaa ccaaaaccca atcagcagca tcaagatcaa 120
gcccgtggtc ttgtgctgcc tggttataac tatctcggac ccggaaacgg tctcgatcga 180
ggagagcctg tcaacagggc agacgaggtc gcgcgagagc acgacatctc gtacaacgag 240
cagcttgagg cgggagacaa cccctacctc aagtacaacc acgcggacgc cgagtttcag 300
gagaagctcg ccgacgacac atccttcggg ggaaacctcg gaaaggcagt ctttcaggcc 360
aagaaaaggg ttctcgaacc ttttggcctg gttgaagagg gtgctaagac ggcccctacc 420
ggaaagcgga tagacgacca ctttccaaaa agaaagaagg ctcggaccga agaggactcc 480
aagccttcca cctcgtcaga cgccgaagct ggacccagcg gatcccagca gctgcaaatc 540
ccagcccaac cagcctcaag tttgggagct gatacaatgt ctgcgggagg tggcggccca 600
ttgggcgaca ataaccaagg tgccgatgga gtgggcaatg cctcgggaga ttggcattgc 660
gattccacgt ggatggggga cagagtcgtc accaagtcca cccgaacctg ggtgctgccc 720
agctacaaca accaccagta ccgagagatc aaaagcggct ccgtcgacgg aagcaacgcc 780
aacgcctact ttggatacag caccccctgg gggtactttg actttaaccg cttccacagc 840
cactggagcc cccgagactg gcaaagactc atcaacaact actggggctt cagaccccgg 900
tccctcagag tcaaaatctt caacattcaa gtcaaagagg tcacggtgca ggactccacc 960
accaccatcg ccaacaacct cacctccacc gtccaagtgt ttacggacga cgactaccag 1020
ctgccctacg tcgtcggcaa cgggaccgag ggatgcctgc cggccttccc tccgcaggtc 1080
tttacgctgc cgcagtacgg ttacgcgacg ctgaaccgcg acaacacaga aaatcccacc 1140
gagaggagca gcttcttctg cctagagtac tttcccagca agatgctgag aacgggcaac 1200
aactttgagt ttacctacaa ctttgaggag gtgcccttcc actccagctt cgctcccagt 1260
cagaacctgt tcaagctggc caacccgctg gtggaccagt acttgtaccg cttcgtgagc 1320
acaaataaca ctggcggagt ccagttcaac aagaacctgg ccgggagata cgccaacacc 1380
tacaaaaact ggttcccggg gcccatgggc cgaacccagg gctggaacct gggctccggg 1440
gtcaaccgcg ccagtgtcag cgccttcgcc acgaccaata ggatggagct cgagggcgcg 1500
agttaccagg tgcccccgca gccgaacggc atgaccaaca acctccaggg cagcaacacc 1560
tatgccctgg agaacactat gatcttcaac agccagccgg cgaacccggg caccaccgcc 1620
acgtacctcg agggcaacat gctcatcacc agcgagagcg agacgcagcc ggtgaaccgc 1680
gtggcgtaca acgtcggcgg gcagatggcc accaacaacc agagctccac cactgccccc 1740
gcgaccggca cgtacaacct ccaggaaatc gtgcccggca gcgtgtggat ggagagggac 1800
gtgtacctcc aaggacccat ctgggccaag atcccagaga cgggggcgca ctttcacccc 1860
tctccggcca tgggcggatt cggactcaaa cacccaccgc ccatgatgct catcaagaac 1920
acgcctgtgc ccggaaatat caccagcttc tcggacgtgc ccgtcagcag cttcatcacc 1980
cagtacagca ccgggcaggt caccgtggag atggagtggg agctcaagaa ggaaaactcc 2040
aagaggtgga acccagagat ccagtacaca aacaactaca acgaccccca gtttgtggac 2100
tttgccccgg acagcaccgg ggaatacaga accaccagac ctatcggaac ccgatacctt 2160
acccgacccc tt 2172

<210> SEQ ID NO 3
<211> LENGTH: 724
<212> TYPE: PRT
<213> ORGANISM: Artificial Sequence
<220> FEATURE:
<223> OTHER INFORMATION: Synthetic polypeptide

<400> SEQUENCE: 3

Met Ser Phe Val Asp His Pro Pro Asp Trp Leu Glu Glu Val Gly Glu
1 5 10 15

Gly Leu Arg Glu Phe Leu Gly Leu Glu Ala Gly Pro Pro Lys Pro Lys
20 25 30

Pro Asn Gln Gln His Gln Asp Gln Ala Arg Gly Leu Val Leu Pro Gly
35 40 45

Tyr Asn Tyr Leu Gly Pro Gly Asn Gly Leu Asp Arg Gly Glu Pro Val
50 55 60

Asn Arg Ala Asp Glu Val Ala Arg Glu His Asp Ile Ser Tyr Asn Glu
65 70 75 80

Gln Leu Glu Ala Gly Asp Asn Pro Tyr Leu Lys Tyr Asn His Ala Asp
85 90 95

Ala Glu Phe Gln Glu Lys Leu Ala Asp Asp Thr Ser Phe Gly Gly Asn
100 105 110

Leu Gly Lys Ala Val Phe Gln Ala Lys Lys Arg Val Leu Glu Pro Phe
115 120 125

Gly Leu Val Glu Glu Gly Ala Lys Thr Ala Pro Thr Gly Lys Arg Ile
130 135 140

Asp Asp His Phe Pro Lys Arg Lys Lys Ala Arg Thr Glu Glu Asp Ser
145 150 155 160

Lys Pro Ser Thr Ser Ser Asp Ala Glu Ala Gly Pro Ser Gly Ser Gln
165 170 175

Gln Leu Gln Ile Pro Ala Gln Pro Ala Ser Ser Leu Gly Ala Asp Thr
180 185 190

Met Gly Ala Gly Gly Gly Gly Pro Leu Gly Asp Asn Asn Gln Gly Ala
195 200 205

Asp Gly Val Gly Asn Ala Ser Gly Asp Trp His Cys Asp Ser Thr Trp
210 215 220

Met Gly Asp Arg Val Val Thr Lys Ser Thr Arg Thr Trp Val Leu Pro
225 230 235 240

Ser Tyr Asn Asn His Gln Tyr Arg Glu Ile Lys Ser Gly Ser Val Asp
245 250 255

Gly Ser Asn Ala Asn Ala Tyr Phe Gly Tyr Ser Thr Pro Trp Gly Tyr
260 265 270

Phe Asp Phe Asn Arg Phe His Ser His Trp Ser Pro Arg Asp Trp Gln
275 280 285

Arg Leu Ile Asn Asn Tyr Trp Gly Phe Arg Pro Arg Ser Leu Arg Val
290 295 300

Lys Ile Phe Asn Ile Gln Val Lys Glu Val Thr Val Gln Asp Ser Thr
305 310 315 320

Thr Thr Ile Ala Asn Asn Leu Thr Ser Thr Val Gln Val Phe Thr Asp
325 330 335

Asp Asp Tyr Gln Leu Pro Tyr Val Val Gly Asn Gly Thr Glu Gly Cys

```
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu


<210> SEQ ID NO 4
<211> LENGTH: 2172
<212> TYPE: DNA
<213> ORGANISM: Artificial Sequence
<220> FEATURE:
```

<223> OTHER INFORMATION: Synthetic polynucleotide

<400> SEQUENCE: 4

```
atgtcttttg ttgatcaccc tccagattgg ttggaagaag ttggtgaagg tcttcgcgag     60
tttttgggcc ttgaagcggg cccaccgaaa ccaaaaccca atcagcagca tcaagatcaa    120
gcccgtggtc ttgtgctgcc tggttataac tatctcggac ccggaaacgg tctcgatcga    180
ggagagcctg tcaacagggc agacgaggtc gcgcgagagc acgacatctc gtacaacgag    240
cagcttgagg cgggagacaa cccctacctc aagtacaacc acgcggacgc cgagtttcag    300
gagaagctcg ccgacgacac atccttcggg ggaaacctcg gaaaggcagt ctttcaggcc    360
aagaaaaggg ttctcgaacc ttttggcctg gttgaagagg gtgctaagac ggcccctacc    420
ggaaagcgga tagacgacca ctttccaaaa agaaagaagg ctcggaccga agaggactcc    480
aagccttcca cctcgtcaga cgccgaagct ggacccagcg gatcccagca gctgcaaatc    540
ccagcccaac cagcctcaag tttgggagct gatacaatgg gtgcgggagg tggcggccca    600
ttgggcgaca ataaccaagg tgccgatgga gtgggcaatg cctcgggaga ttggcattgc    660
gattccacgt ggatggggga cagagtcgtc accaagtcca cccgaacctg ggtgctgccc    720
agctacaaca accaccagta ccgagagatc aaaagcggct ccgtcgacgg aagcaacgcc    780
aacgcctact ttggatacag cacccccctgg gggtactttg actttaaccg cttccacagc    840
cactggagcc cccgagactg gcaaagactc atcaacaact actggggctt cagaccccgg    900
tccctcagag tcaaaatctt caacattcaa gtcaaagagg tcacggtgca ggactccacc    960
accaccatcg ccaacaacct cacctccacc gtccaagtgt ttacggacga cgactaccag   1020
ctgccctacg tcgtcggcaa cgggaccgag ggatgcctgc cggccttccc tccgcaggtc   1080
tttacgctgc cgcagtacgg ttacgcgacg ctgaaccgcg acaacacaga aaatcccacc   1140
gagaggagca gcttcttctg cctagagtac tttcccagca agatgctgag aacgggcaac   1200
aactttgagt ttacctacaa ctttgaggag gtgcccttcc actccagctt cgctcccagt   1260
cagaacctgt tcaagctggc caacccgctg gtggaccagt acttgtaccg cttcgtgagc   1320
acaaataaca ctggcggagt ccagttcaac aagaacctgg ccgggagata cgccaacacc   1380
tacaaaaact ggttcccggg gcccatgggc cgaacccagg gctggaacct gggctccggg   1440
gtcaaccgcg ccagtgtcag cgccttcgcc acgaccaata ggatggagct cgagggcgcg   1500
agttaccagg tgcccccgca gccgaacggc atgaccaaca acctccaggg cagcaacacc   1560
tatgccctgg agaacactat gatcttcaac agccagccgg cgaacccggg caccaccgcc   1620
acgtacctcg agggcaacat gctcatcacc agcgagagcg agacgcagcc ggtgaaccgc   1680
gtggcgtaca acgtcggcgg gcagatggcc accaacaacc agagctccac cactgccccc   1740
gcgaccggca cgtacaacct ccaggaaatc gtgcccggca gcgtgtggat ggagagggac   1800
gtgtacctcc aaggacccat ctgggccaag atcccagaga cgggggcgca ctttcacccc   1860
tctccggcca tgggcggatt cggactcaaa cacccaccgc ccatgatgct catcaagaac   1920
acgcctgtgc ccggaaatat caccagcttc tcggacgtgc ccgtcagcag cttcatcacc   1980
cagtacagca ccgggcaggt caccgtggag atggagtggg agctcaagaa ggaaaactcc   2040
aagaggtgga acccagagat ccagtacaca aacaactaca acgacccccca gtttgtggac   2100
tttgccccgg acagcaccgg ggaatacaga accaccagac ctatcggaac ccgatacctt   2160
acccgacccc tt                                                       2172
```

```
<210> SEQ ID NO 5
<211> LENGTH: 724
<212> TYPE: PRT
<213> ORGANISM: Artificial Sequence
<220> FEATURE:
<223> OTHER INFORMATION: Synthetic polypeptide

<400> SEQUENCE: 5

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
```

```
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Arg Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu


<210> SEQ ID NO 6
<211> LENGTH: 2172
<212> TYPE: DNA
<213> ORGANISM: Artificial Sequence
<220> FEATURE:
<223> OTHER INFORMATION: Synthetic polynucleotide

<400> SEQUENCE: 6

atgtcttttg ttgatcaccc tccagattgg ttggaagaag ttggtgaagg tcttcgcgag      60
```

-continued

```
tttttgggcc ttgaagcggg cccaccgaaa ccaaaaccca atcagcagca tcaagatcaa    120

gcccgtggtc ttgtgctgcc tggttataac tatctcggac ccggaaacgg tctcgatcga    180

ggagagcctg tcaacagggc agacgaggtc gcgcgagagc acgacatctc gtacaacgag    240

cagcttgagg cgggagacaa cccctacctc aagtacaacc acgcggacgc cgagtttcag    300

gagaagctcg ccgacgacac atccttcggg ggaaacctcg gaaaggcagt ctttcaggcc    360

aagaaaaggg ttctcgaacc ttttggcctg gttgaagagg gtgctaagac ggcccctacc    420

ggaaagcgga tagacgacca ctttccaaaa agaaagaagg ctcggaccga agaggactcc    480

aagccttcca cctcgtcaga cgccgaagct ggacccagcg gatcccagca gctgcaaatc    540

ccagcccaac cagcctcaag tttgggagct gatacaatgt ctgcgggagg tggcggccca    600

ttgggcgaca ataaccaagg tgccgatgga gtgggcaatg cctcgggaga ttggcattgc    660

gattccacgt ggatggggga cagagtcgtc accaagtcca cccgaacctg ggtgctgccc    720

agctacaaca accaccagta ccgagagatc aaaagcggct ccgtcgacgg aagcaacgcc    780

aacgcctact ttggatacag caccccctgg gggtactttg actttaaccg cttccacagc    840

cactggagcc cccgagactg gcaaagactc atcaacaact actggggctt cagaccccgg    900

tccctcagag tcaaaatctt caacattcaa gtcaaagagg tcacggtgca ggactccacc    960

accaccatcg ccaacaacct cacctccacc gtccaagtgt ttacggacga cgactaccag   1020

ctgccctacg tcgtcggcaa cgggaccgag ggatgcctgc cggccttccc tccgcaggtc   1080

tttacgctgc cgcagtacgg ttacgcgacg ctgaaccgcg acaacacaga aaatcccacc   1140

gagaggagca gcttcttctg cctagagtac tttcccagca agatgctgag aacgggcaac   1200

aactttgagt ttacctacaa ctttgaggag gtgcccttcc actccagctt cgctcccagt   1260

cagaacctgt tcaagctggc caacccgctg gtggaccagt acttgtaccg cttcgtgagc   1320

acaaataaca ctggcggagt ccagttcaac aagaacctgg ccgggagata cgccaacacc   1380

tacaaaaact ggttcccggg gcccatgggc cgaacccagc gctggaacct gggctccggg   1440

gtcaaccgcg ccagtgtcag cgccttcgcc acgaccaata ggatggagct cgagggcgcg   1500

agttaccagg tgcccccgca gccgaacggc atgaccaaca acctccaggg cagcaacacc   1560

tatgccctgg agaacactat gatcttcaac agccagccgg cgaacccggg caccaccgcc   1620

acgtacctcg agggcaacat gctcatcacc agcgagagcg agacgcagcc ggtgaaccgc   1680

gtggcgtaca acgtcggcgg gcagatggcc accaacaacc agagctccac cactgccccc   1740

gcgaccggca cgtacaacct ccaggaaatc gtgcccggca gcgtgtggat ggagagggac   1800

gtgtacctcc aaggacccat ctgggccaag atcccagaga cgggggcgca ctttcacccc   1860

tctccggcca tgggcggatt cggactcaaa cacccaccgc ccatgatgct catcaagaac   1920

acgcctgtgc ccggaaatat caccagcttc tcggacgtgc ccgtcagcag cttcatcacc   1980

cagtacagca ccgggcaggt caccgtggag atggagtggg agctcaagaa ggaaaactcc   2040

aagaggtgga acccagagat ccagtacaca aacaactaca acgaccccca gtttgtggac   2100

tttgccccgg acagcaccgg ggaatacaga accaccagac ctatcggaac ccgatacctt   2160

acccgacccc tt                                                       2172
```

<210> SEQ ID NO 7
<211> LENGTH: 724
<212> TYPE: PRT
<213> ORGANISM: Artificial Sequence
<220> FEATURE:
<223> OTHER INFORMATION: Synthetic polypeptide

<400> SEQUENCE: 7

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
```

```
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Arg Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu


<210> SEQ ID NO 8
<211> LENGTH: 2172
<212> TYPE: DNA
<213> ORGANISM: Artificial Sequence
<220> FEATURE:
<223> OTHER INFORMATION: Synthetic polynucleotide

<400> SEQUENCE: 8

atgtcttttg ttgatcaccc tccagattgg ttggaagaag ttggtgaagg tcttcgcgag      60

tttttgggcc ttgaagcggg cccaccgaaa ccaaaaccca atcagcagca tcaagatcaa     120

gcccgtggtc ttgtgctgcc tggttataac tatctcggac ccggaaacgg tctcgatcga     180

ggagagcctg tcaacagggc agacgaggtc gcgcgagagc acgacatctc gtacaacgag     240
```

```
cagcttgagg cgggagacaa cccctacctc aagtacaacc acgcggacgc cgagtttcag    300

gagaagctcg ccgacgacac atccttcggg ggaaacctcg gaaaggcagt ctttcaggcc    360

aagaaaaggg ttctcgaacc ttttggcctg gttgaagagg gtgctaagac ggcccctacc    420

ggaaagcgga tagacgacca ctttccaaaa agaaagaagg ctcggaccga agaggactcc    480

aagccttcca cctcgtcaga cgccgaagct ggacccagcg gatcccagca gctgcaaatc    540

ccagcccaac cagcctcaag tttgggagct gatacaatgt ctgcgggagg tggcggccca    600

ttgggcgaca ataaccaagg tgccgatgga gtgggcaatg cctcgggaga ttggcattgc    660

gattccacgt ggatggggga cagagtcgtc accaagtcca cccgaacctg ggtgctgccc    720

agctacaaca accaccagta ccgagagatc aaaagcggct ccgtcgacgg aagcaacgcc    780

aacgcctact ttggatacag caccccctgg gggtactttg actttaaccg cttccacagc    840

cactggagcc cccgagactg gcaaagactc atcaacaact actggggctt cagaccccgg    900

tccctcagag tcaaaatctt caacattcaa gtcaaagagg tcacggtgca ggactccacc    960

accaccatcg ccaacaacct cacctccacc gtccaagtgt ttacggacga cgactaccag   1020

ctgccctacg tcgtcggcaa cgggaccgag ggatgcctgc cggccttccc tccgcaggtc   1080

tttacgctgc cgcagtacgg ttacgcgacg ctgaaccgcg acaacacaga aaatcccacc   1140

gagaggagca gcttcttctg cctagagtac tttcccagca agatgctgag aacgggcaac   1200

aactttgagt ttacctacaa ctttgaggag gtgcccttcc actccagctt cgctcccagt   1260

cagaacctgt tcaagctggc caacccgctg gtggaccagt acttgtaccg cttcgtgagc   1320

acaaataaca ctggcggagt ccagttcaac aagaacctgg ccgggagata cgccaacacc   1380

tacaaaaact ggttcccggg gcccatgggc cgaacccagg gctggaacct gggctccggg   1440

gtcaaccgcg ccagtgtcag cgccttcgcc acgaccaata ggatggagct cgagggcgcg   1500

agttaccagg tgcccccgca gccgaacggc atgaccaaca acctccaggg cagcaacacc   1560

tatgccctgg agaacactat gatcttcaac agccagccgg cgaacccggg caccaccgcc   1620

acgtacctcg agggcaacat gctcatcacc agcgagagcg agacgcagcc ggtgaaccgc   1680

gtggcgtacc gcgtcggcgg gcagatggcc accaacaacc agagctccac cactgccccc   1740

gcgaccggca cgtacaacct ccaggaaatc gtgcccggca gcgtgtggat ggagagggac   1800

gtgtacctcc aaggacccat ctgggccaag atcccagaga cgggggcgca ctttcacccc   1860

tctccggcca tgggcggatt cggactcaaa cacccaccgc ccatgatgct catcaagaac   1920

acgcctgtgc ccggaaatat caccagcttc tcggacgtgc ccgtcagcag cttcatcacc   1980

cagtacagca ccgggcaggt caccgtggag atggagtggg agctcaagaa ggaaaactcc   2040

aagaggtgga acccagagat ccagtacaca aacaactaca acgaccccca gtttgtggac   2100

tttgccccgg acagcaccgg ggaatacaga accaccagac ctatcggaac ccgatacctt   2160

acccgacccc tt                                                       2172
```

<210> SEQ ID NO 9
<211> LENGTH: 724
<212> TYPE: PRT
<213> ORGANISM: Artificial Sequence
<220> FEATURE:
<223> OTHER INFORMATION: Synthetic polypeptide

<400> SEQUENCE: 9

```
Met Ser Phe Val Asp His Pro Pro Asp Trp Leu Glu Glu Val Gly Glu
1               5                   10                  15
```

-continued

```
Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
```

```
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Arg Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu


<210> SEQ ID NO 10
<211> LENGTH: 2172
<212> TYPE: DNA
<213> ORGANISM: Artificial Sequence
<220> FEATURE:
<223> OTHER INFORMATION: Synthetic polynucleotide

<400> SEQUENCE: 10

atgtcttttg ttgatcaccc tccagattgg ttggaagaag ttggtgaagg tcttcgcgag      60

tttttgggcc ttgaagcggg cccaccgaaa ccaaaaccca atcagcagca tcaagatcaa     120

gcccgtggtc ttgtgctgcc tggttataac tatctcggac ccggaaacgg tctcgatcga     180

ggagagcctg tcaacagggc agacgaggtc gcgcgagagc acgacatctc gtacaacgag     240

cagcttgagg cgggagacaa cccctacctc aagtacaacc acgcggacgc cgagtttcag     300

gagaagctcg ccgacgacac atccttcggg ggaaacctcg gaaaggcagt ctttcaggcc     360

aagaaaaggg ttctcgaacc ttttggcctg gttgaagagg gtgctaagac ggcccctacc     420
```

```
ggaaagcgga tagacgacca ctttccaaaa agaaagaagg ctcggaccga agaggactcc    480

aagccttcca cctcgtcaga cgccgaagct ggacccagcg gatcccagca gctgcaaatc    540

ccagcccaac cagcctcaag tttgggagct gatacaatgt ctgcgggagg tggcggccca    600

ttgggcgaca ataaccaagg tgccgatgga gtgggcaatg cctcgggaga ttggcattgc    660

gattccacgt ggatggggga cagagtcgtc accaagtcca cccgaacctg ggtgctgccc    720

agctacaaca accaccagta ccgagagatc aaaagcggct ccgtcgacgg aagcaacgcc    780

aacgcctact ttggatacag cacccccctgg gggtactttg actttaaccg cttccacagc    840

cactggagcc cccgagactg gcaaagactc atcaacaact actggggctt cagaccccgg    900

tccctcagag tcaaaatctt caacattcaa gtcaaagagg tcacggtgca ggactccacc    960

accaccatcg ccaacaacct cacctccacc gtccaagtgt ttacggacga cgactaccag   1020

ctgccctacg tcgtcggcaa cgggaccgag ggatgcctgc cggccttccc tccgcaggtc   1080

tttacgctgc cgcagtacgg ttacgcgacg ctgaaccgcg acaacacaga aaatcccacc   1140

gagaggagca gcttcttctg cctagagtac tttcccagca agatgctgag aacgggcaac   1200

aactttgagt ttacctacaa ctttgaggag gtgcccttcc actccagctt cgctcccagt   1260

cagaacctgt tcaagctggc caacccgctg gtggaccagt acttgtaccg cttcgtgagc   1320

acaaataaca ctggcggagt ccagttcaac aagaacctgg ccgggagata cgccaacacc   1380

tacaaaaact ggttcccggg gcccatgggc cgaacccagg gctggaacct gggctccggg   1440

gtcaaccgcg ccagtgtcag cgccttcgcc acgaccaata ggatggagct cgagggcgcg   1500

agttaccagg tgcccccgca gccgaacggc atgaccaaca acctccaggg cagcaacacc   1560

tatgccctgg agaacactat gatcttcaac agccagccgg cgaacccggg caccaccgcc   1620

acgtacctcg agggcaacat gctcatcacc agcgagagcg agacgcagcc ggtgaaccgc   1680

gtggcgtaca acgtcggcgg gcagatggcc accaacagac agagctccac cactgccccc   1740

gcgaccggca cgtacaacct ccaggaaatc gtgcccggca gcgtgtggat ggagagggac   1800

gtgtacctcc aaggacccat ctgggccaag atcccagaga cgggggcgca ctttcacccc   1860

tctccggcca tgggcggatt cggactcaaa cacccaccgc ccatgatgct catcaagaac   1920

acgcctgtgc ccggaaatat caccagcttc tcggacgtgc ccgtcagcag cttcatcacc   1980

cagtacagca ccgggcaggt caccgtggag atggagtggg agctcaagaa ggaaaactcc   2040

aagaggtgga acccagagat ccagtacaca aacaactaca acgaccccca gtttgtggac   2100

tttgccccgg acagcaccgg ggaatacaga accaccagac ctatcggaac ccgatacctt   2160

acccgacccc tt                                                       2172
```

<210> SEQ ID NO 11
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 11

```
tatctaccaa cctccaggca ggcaacgcac aagcagctac cgcag                     45
```

<210> SEQ ID NO 12
<211> LENGTH: 25
<212> TYPE: DNA
<213> ORGANISM: Artificial Sequence
<220> FEATURE:
<223> OTHER INFORMATION: Synthetic polynucleotide -continued

```
<400> SEQUENCE: 12

ccaggttcca gcgctgggtt cggcc                                         25


<210> SEQ ID NO 13
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 13

ccgcgtggcg taccgcgtcg gcgggcag                                      28


<210> SEQ ID NO 14
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 14

cagtggtgga gctctgtctg ttggtggcca tctg                               34
```